(12) United States Patent
Lin et al.

(10) Patent No.: US 10,876,971 B2
(45) Date of Patent: Dec. 29, 2020

(54) NUCLEIC ACID NANOSTRUCTURE BARCODE PROBES

(71) Applicants: President and Fellows of Harvard College, Cambridge, MA (US); Dana-Farber Cancer Institute, Inc., Boston, MA (US)

(72) Inventors: Chenxiang Lin, Cambridge, MA (US); Chao Li, Boston, MA (US); William M. Shih, Cambridge, MA (US); Peng Yin, Brookline, MA (US); Ralf Jungmann, Munich (DE)

(73) Assignees: President and Fellows of Harvard College, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 217 days.

(21) Appl. No.: 16/008,719

(22) Filed: Jun. 14, 2018

(65) Prior Publication Data
US 2019/0003973 A1  Jan. 3, 2019

Related U.S. Application Data

(62) Division of application No. 13/882,223, filed as application No. PCT/US2011/058458 on Oct. 28, 2011, now Pat. No. 10,024,796.
(Continued)

(51) Int. Cl.
| G01N 21/64 | (2006.01) |
| C12Q 1/6825 | (2018.01) |
| B82Y 15/00 | (2011.01) |

(52) U.S. Cl.
CPC ....... *G01N 21/6486* (2013.01); *C12Q 1/6825* (2013.01); *B82Y 15/00* (2013.01)

(58) Field of Classification Search
None
See application file for complete search history.

(56) References Cited

U.S. PATENT DOCUMENTS

| 5,866,336 A | 2/1999 | Nazarenko et al. |
| 6,083,486 A | 7/2000 | Weissleder et al. |

(Continued)

FOREIGN PATENT DOCUMENTS

| CN | 1836050 A | 9/2006 |
| CN | 101048505 A | 10/2007 |

(Continued)

OTHER PUBLICATIONS

Jungmann et al. (Single-Molecule Kinetics and Super-Resolution Microscopy by Fluorescence Imaging of Transient Binding on DNA Origami, Nano Lett., 2010, 10 (11), pp. 4756-4761, Publication Date (Web): Oct. 19, 2010).*
(Continued)

*Primary Examiner* — Aaron A Priest
(74) *Attorney, Agent, or Firm* — Wolf, Greenfield & Sacks, P.C.

(57) ABSTRACT

Provided herein are, inter alia, barcode probes comprised of transiently or stably fluorescently labeled nucleic acid nanostructures that are fully addressable and able to be read using standard fluorescent microscope and methods of use thereof including methods of use as detectable labels for probes.

20 Claims, 15 Drawing Sheets
Specification includes a Sequence Listing.

Related U.S. Application Data

(60) Provisional application No. 61/408,358, filed on Oct. 29, 2010.

(56) References Cited

U.S. PATENT DOCUMENTS

| | | | |
|---|---|---|---|
| 6,150,173 | A | 11/2000 | Schubert |
| 6,534,041 | B1 | 3/2003 | Licha et al. |
| 6,833,246 | B2 | 12/2004 | Balasubramanian |
| 6,924,115 | B2 | 8/2005 | Schubert |
| 6,942,968 | B1 | 9/2005 | Dickinson et al. |
| 7,371,520 | B2 | 5/2008 | Zhao et al. |
| 7,838,302 | B2 | 11/2010 | Zhuang et al. |
| 8,481,714 | B2 | 7/2013 | Fujimoto et al. |
| 9,944,972 | B2 | 4/2018 | Yin et al. |
| 10,024,796 | B2 | 7/2018 | Lin et al. |
| 2002/0015679 | A1 | 2/2002 | Kotov |
| 2002/0064772 | A1 | 5/2002 | Gildea et al. |
| 2002/0106648 | A1 | 8/2002 | Lizardi et al. |
| 2002/0173053 | A1 | 11/2002 | Damaj et al. |
| 2002/0177149 | A1 | 11/2002 | Rimm et al. |
| 2003/0044353 | A1 | 3/2003 | Weissleder et al. |
| 2003/0064398 | A1 | 4/2003 | Barnes |
| 2003/0073149 | A1 | 4/2003 | Archer et al. |
| 2004/0121385 | A1 | 6/2004 | Andersson et al. |
| 2004/0248325 | A1 | 12/2004 | Bukusoglu |
| 2005/0074781 | A1 | 4/2005 | Von Schroeder et al. |
| 2005/0169843 | A1 | 8/2005 | Weissleder et al. |
| 2005/0171434 | A1 | 8/2005 | Madden et al. |
| 2005/0287578 | A1 | 12/2005 | Davis |
| 2006/0063196 | A1 | 3/2006 | Akeson et al. |
| 2006/0188902 | A1 | 8/2006 | Narayanan et al. |
| 2006/0199216 | A1 | 9/2006 | Su et al. |
| 2006/0252079 | A1 | 11/2006 | Oldham et al. |
| 2006/0292616 | A1 | 12/2006 | Neely et al. |
| 2007/0048759 | A1 | 3/2007 | Luo et al. |
| 2007/0117109 | A1* | 5/2007 | Rothemund ............ C12P 19/34 435/6.12 |
| 2008/0118934 | A1 | 5/2008 | Gerdes et al. |
| 2008/0182336 | A1 | 7/2008 | Zhuang et al. |
| 2008/0287668 | A1 | 11/2008 | Toth-Fejel et al. |
| 2009/0011956 | A1 | 1/2009 | Yin et al. |
| 2010/0015607 | A1 | 1/2010 | Geiss et al. |
| 2010/0069621 | A1 | 3/2010 | Maune et al. |
| 2010/0081134 | A1 | 4/2010 | Mirkin et al. |
| 2010/0216978 | A1* | 8/2010 | Shih ..................... A61K 47/26 536/22.1 |
| 2012/0004132 | A1 | 1/2012 | Zhang et al. |
| 2012/0022243 | A1 | 1/2012 | Yin |
| 2012/0022244 | A1* | 1/2012 | Yin ..................... B82Y 40/00 536/23.1 |
| 2012/0107798 | A1 | 5/2012 | Santangelo |
| 2012/0178081 | A1 | 7/2012 | Nguyen et al. |
| 2012/0252685 | A1 | 10/2012 | Treynor et al. |
| 2013/0027518 | A1 | 1/2013 | Mackay et al. |
| 2013/0072390 | A1 | 3/2013 | Wang et al. |
| 2013/0261019 | A1 | 10/2013 | Lin et al. |
| 2014/0038201 | A1 | 2/2014 | Zhuang et al. |
| 2014/0349288 | A1 | 11/2014 | Church et al. |
| 2016/0319328 | A1 | 11/2016 | Yin et al. |
| 2017/0137864 | A1 | 5/2017 | Yin et al. |
| 2017/0327888 | A1 | 11/2017 | Ong et al. |
| 2018/0010174 | A1 | 1/2018 | Schaus et al. |
| 2018/0216159 | A1 | 8/2018 | Yin et al. |
| 2018/0363045 | A1 | 12/2018 | Zhang et al. |
| 2019/0106733 | A1 | 4/2019 | Kishi et al. |

FOREIGN PATENT DOCUMENTS

| | | |
|---|---|---|
| CN | 101541975 A | 9/2009 |
| CN | 102317471 A | 1/2012 |
| CN | 102782158 A | 11/2012 |
| CN | 103014168 A | 4/2013 |
| DE | 4421891 A1 | 1/1996 |
| JP | 2003-259869 A | 9/2003 |
| WO | WO 98/18961 A1 | 5/1998 |
| WO | WO 00/03034 A2 | 1/2000 |
| WO | WO 00/20641 A1 | 4/2000 |
| WO | WO 00/58507 A1 | 10/2000 |
| WO | WO 02/079771 A1 | 10/2002 |
| WO | WO 2005/017485 A2 | 2/2005 |
| WO | WO 2007/076128 A2 | 7/2007 |
| WO | WO 2011/156434 A2 | 12/2011 |
| WO | WO 2012/058638 A2 | 5/2012 |
| WO | WO 2012/071428 A2 | 5/2012 |
| WO | WO 2013/010023 A2 | 1/2013 |
| WO | WO 2013/012434 A1 | 1/2013 |
| WO | WO 2014/028538 A2 | 2/2014 |
| WO | WO 2014/135838 A1 | 9/2014 |
| WO | WO 2015/089506 A2 | 6/2015 |
| WO | WO 2015/138653 A1 | 9/2015 |
| WO | WO 2019/147945 A1 | 8/2019 |

OTHER PUBLICATIONS

Steinhauer et al. (DNA origami as a nanoscopic ruler for super-resolution microscopy, Angew Chem Int Ed Engl. 2009; 48(47): 8870-3).*

Lin et al. (Designer DNA Nanoarchitectures, Biochemistry. Mar. 3, 2009; 48(8): 1663-1674).*

Yin et al. (Programming DNA Tube Circumferences, Science Aug. 8, 2008:vol. 321, Issue 5890, pp. 824-826).*

Douglas et al. (Self-assembly of DNA into nanoscale three-dimensional shapes, Nature. May 21, 2009;459(7245):414-8).*

Mathieu et al. (Six-Helix Bundles Designed from DNA, Nano Lett. Apr. 2005; 5(4): 661-665).*

Li et al. (Multiplexed detection of pathogen DNA with DNA-based fluorescence nanobarcodes, Nature Biotechnology 23, 885-889 (2005), Published online: Jun. 12, 2005).*

Rothemund (Folding DNA to create nanoscale shapes and patterns, Nature 440, 297-302 (Mar. 16, 2006)).*

Kuzuya et al. (Six-helix and eight-helix DNA nanotubes assembled from half-tubes, Nano Lett. Jun. 2007;7(6):1757-63. Epub May 15, 2007).*

Baccouche et al., Dynamic DNA-toolbox reaction circuits: a walkthrough. Methods. May 15, 2014;67(2):234-49. doi: 10.1016/j.ymeth.2014.01.015. Epub Feb. 2, 2014.

Fiandaca et al., Self-reporting PNA/DNA primers for PCR analysis. Genome Res. Apr. 2011;11(4):609-13. doi: 10.1101/gr.170401.

Forster et al., A human gut bacterial genome and culture collection for improved metagenomic analyses. Nat Biotechnol. 2019;37(2):186-192. doi:10.1038/s41587-018-0009-7.

Montagne et al., Programming an in vitro DNA oscillator using a molecular networking strategy. Mol Syst Biol. Feb. 1, 2011;7:466. doi: 10.1038/msb.2010.120. Erratum in: Mol Syst Biol. Mar. 8, 2011;7:476. Mol Syst Biol. 2011;7. doi:10.1038/msb.2011.12.

Nazarenko et al., Multiplex quantitative PCR using self-quenched primers labeled with a single fluorophore. Nucleic Acids Res. May 1, 2002;30(9):e37(1-7). doi: 10.1093/nar/30.9.e37.

Zhu et al., Toehold-mediated strand displacement reaction triggered isothermal DNA amplification for highly sensitive and selective fluorescent detection of single-base mutation. Biosens Bioelectron. Sep. 15, 2014;59:276-81. doi: 10.1016/j.bios.2014.03.051. Epub Apr. 1, 2014.

[No Author Listed] DLP® 0.95 1080p 2 x LVDS Type A DMD. Retrieved (Mar. 13, 2015) from: <www.ti.com/lit/ds/dlps025b/dlps025b.pdf>.

[No Author Listed] Scientists watch a chemical bond break using molecule's electrons. University of Ottawa. ScienceDaily. www.sciencedaily.com/releases/2010/07/100728131709.htm (accessed Mar. 19, 2015).

[No Author Listed] DNA origami scaffolds for cryo-EM visualization of membrane associated complexes. University of Michigan. Project ID: 377. Last accessed from http://mcubed.umich.edu/projects/dna-origami-scaffolds-cryo-em-visualization-membrane-associated-complexes on Nov. 12, 2015.

(56) References Cited

OTHER PUBLICATIONS

Abulrob et al., Nanoscale imaging of epidermal growth factor receptor clustering: effects of inhibitors. J Biol Chem. Jan. 29, 2010;285(5):3145-56. doi: 10.1074/jbc.M109.073338. Epub Dec. 3, 2009.

Agasti et al., Dual imaging and photoactivated nanoprobe for controlled cell tracking. Small. Jan. 28, 2013;9(2):222-7. doi: 10.1002/smll.201201007. Epub Sep. 21, 2012.

Agasti et al., Photocleavable DNA barcode-antibody conjugates allow sensitive and multiplexed protein analysis in single cells. J Am Chem Soc. Nov. 14, 2012;134(45):18499-502. doi:10.1021/ja307689w. Epub Nov. 2, 2012.

Agasti et al., Photoregulated release of caged anticancer drugs from gold nanoparticles. J Am Chem Soc. Apr. 29, 2009;131(16):5728-9. doi: 10.1021/ja900591t.

Agasti et al., DNA-barcoded labeling probes for highly multiplexed Exchange-PAINT imaging. Chem Sci. Apr. 1, 2017;8(4):3080-3091. doi: 10.1039/c6sc05420j. Epub Jan. 30, 2017.

Aitken et al., An oxygen scavenging system for improvement of dye stability in single-molecule fluorescence experiments. Biophys J. Mar. 1, 2008;94(5):1826-35. Epub Oct. 5, 2007.

Amouyal et al., On the Photoionization Energy Threshold of Tryptophan in Aqueous Solutions. Photochem Photobiol. 1979;29(6):1071-7.

Anderson et al., Improved fluoroimmunoassays using the dye Alexa Fluor 647 with the RAPTOR, a fiber optic biosensor. J Immunol Methods. Dec. 20, 2002;271(1-2):17-24.

Anshelevich et al., Slow relaxational processes in the melting of linear biopolymers: a theory and its application to nucleic acids. Biopolymers. Jan. 1984;23(1):39-58.

Asanuma et al., Enantioselective Incorporation of Azobenzenes into Oligodeoxyribonucleotide for Effective Photoregulation of Duplex Formation This work was partially supported by a Grant-in-Aid for Scientific Research from the Ministry of Education, Culture, Sports, Science and Technology, Japan (Molecular Synchronization for Design of New Materials System). The support by the Grant from "Research for the Future" Program of the Japan Society for the Promotion of Science JSPS-RFTF97I00301) is also acknowledged. . Angew Chem Int Ed Engl. Jul. 16, 2001;40(14):2671-2673.

Averbuch et al., Two Linear Unmixing Algorithms to Recognize Targets Using Supervised Classification and Orthogonal Rotation in Airborne Hyperspectral Images. Remote Sens. 2012;4(2):532-60.

Azcona et al., Development and clinical evaluation of automatic fiducial detection for tumor tracking in cine megavoltage images during volumetric modulated arc therapy. Med Phys. Mar. 2013;40(3):031708. doi:10.1118/1.4791646.

Backlund et al., Simultaneous, accurate measurement of the 3D position and orientation of single molecules. Proc Natl Acad Sci U S A. Nov. 20, 2012;109(47):19087-92. doi:10.1073/pnas.1216687109. Epub Nov. 5, 2012.

Badieirostami et al., Three-dimensional localization precision of the double-helix point spread function versus astigmatism and biplane. Appl Phys Lett. Oct. 18, 2010;97(16):161103.

Bai et al., Cryo-EM structure of a 3D DNA-origami object. Proc Natl Acad Sci U S A. Dec. 4, 2012;109(49):20012-7. doi:10.1073/pnas.1215713109. Epub Nov. 19, 2012.

Bates et al., Multicolor super-resolution imaging with photo-switchable fluorescent probes. Science. Sep. 21, 2007;317(5845):1749-53. Epub Aug. 16, 2007.

Bates et al., Short-range spectroscopic ruler based on a single-molecule optical switch. Phys Rev Lett. Mar. 18, 2005;94(10):108101. Epub Mar. 15, 2005.

Beliveau et al., Versatile design and synthesis platform for visualizing genomes with Oligopaint FISH probes. Proc Natl Acad Sci U S A. Dec. 26, 2012;109(52):21301-6. doi:10.1073/pnas.1213818110. Epub Dec. 11, 2012.

Belyy et al., Processive cytoskeletal motors studied with single-molecule fluorescence techniques. FEBS Lett. Oct. 1, 2014;588(19):3520-5. doi:10.1016/j.febslet.2014.05.040. Epub May 29, 2014.

Ben-Shem et al., The structure of the eukaryotic ribosome at 3.0 Å resolution. Science. Dec. 16, 2011;334(6062):1524-9. doi: 10.1126/science.1212642. Epub Nov. 17, 2011.

Bernard et al., Acquired dendritic channelopathy in temporal lobe epilepsy. Science. Jul. 23, 2004;305(5683):532-5.

Bernstein et al., Optogenetic tools for analyzing the neural circuits of behavior. Trends Cogn Sci. Dec. 2011;15(12):592-600. doi:10.1016/j.tics.2011.10.003. Epub Nov. 4, 2011.

Betzig et al., Imaging intracellular fluorescent proteins at nanometer resolution. Science. Sep. 15, 2006;313(5793):1642-5. Epub Aug. 10, 2006.

Bisby et al., Nanoscale hydroxyl radical generation from multiphoton ionization of tryptophan. Photochem Photobiol. Jan.-Feb. 2009;85(1):353-7. doi:10.1111/j.1751-1097.2008.00447.x.

Borisenko et al., Simultaneous optical and electrical recording of single gramicidin channels. Biophys J. Jan. 2003;84(1):612-22.

Braeckmans et al., Encoding microcarriers by spatial selective photobleaching. Nat Mater. Mar. 2003;2(3):169-73.

Brohawn et al., Mechanosensitivity is mediated directly by the lipid membrane in TRAAK and TREK1 K+ channels. Proc Natl Acad Sci U S A. Mar. 4, 2014;111(9):3614-9. doi:10.1073/pnas.1320768111. Epub Feb. 18, 2014.

Bullock, Messengers, motors and mysteries: sorting of eukaryotic mRNAs by cytoskeletal transport. Biochem Soc Trans. Oct. 2011;39(5):1161-5. doi:10.1042/BST0391161.

Cadilhe et al., Random sequential adsorption: from continuum to lattice and pre-patterned substrates. J Phys Condens Matt. 2007;19:065124.

Cao et al., Presynaptic Ca2+ channels compete for channel type-preferring slots in altered neurotransmission arising from Ca2+ channelopathy. Neuron. Aug. 5, 2004;43(3):387-400.

Chapman et al., Femtosecond X-ray protein nanocrystallography. Nature. Feb. 3, 2011;470(7332):73-7. doi: 10.1038/nature09750.

Chen et al., A Quantitative Theory Model of a Photobleaching Mechanism. Chinese Phys Lett. 1940;20(11):1940-3.

Chen et al., High-order photobleaching of green fluorescent protein inside live cells in two-photon excitation microscopy. Biochem Biophys Res Commun. Mar. 15, 2002;291(5):1272-5.

Cheng et al., A primer to single-particle cryo-electron microscopy. Cell. Apr. 23, 2015;161(3):438-49. doi:10.1016/j.cell.2015.03.050.

Chhabra et al., DNA self-assembly for nanomedicine. Adv Drug Deliv Rev. Apr. 30, 2010;62(6):617-25. doi:10.1016/j.addr.2010.03.005. Epub Mar. 15, 2010.

Choi et al., Next-generation in situ hybridization chain reaction: higher gain, lower cost, greater durability. ACS Nano. May 27, 2014;8(5):4284-94. doi: 10.1021/nn405717p. Epub Apr. 8, 2014.

Citri et al., EGF-ERBB signalling: towards the systems level. Nat Rev Mol Cell Biol. Jul. 2006;7(7):505-16.

Conley et al., Cy3-Cy5 covalent heterodimers for single-molecule photoswitching. J Phys Chem B. Sep. 25, 2008;112(38):11878-80. doi:10.1021/jp806698p. Epub Aug. 28, 2008.

De La Cruz et al., Navigating the cell: how motors function in vivo. J Cell Sci. Jul. 15, 2014;127(Pt 14):2997-8. doi: 10.1242/jcs.156414.

Dejneka et al., Rare earth-doped glass microbarcodes. Proc Natl Acad Sci U S A. Jan. 21, 2003;100(2):389-93. Epub Jan. 6, 2003.

Dempsey et al., Evaluation of fluorophores for optimal performance in localization-based super-resolution imaging. Nat Methods. Nov. 6, 2011;8(12):1027-36. doi: 10.1038/nmeth.1768.

Dempsey et al., Photoswitching mechanism of cyanine dyes. J Am Chem Soc. Dec. 30, 2009;131(51):18192-3. doi:10.1021/ja904588g.

Deng et al., CASFISH: CRISPR/Cas9-mediated in situ labeling of genomic loci in fixed cells. Proc Natl Acad Sci U S A. Sep. 22, 2015;112(38):11870-5. doi: 10.1073/pnas.1515692112. Epub Aug. 31, 2015.

Derr et al., Tug-of-war in motor protein ensembles revealed with a programmable DNA origami scaffold. Science. Nov. 2, 2012;338(6107):662-5. doi: 10.1126/science.1226734. Epub Oct. 11, 2012.

Dirks et al., Triggered amplification by hybridization chain reaction. Proc Natl Acad Sci U S A. Oct. 26, 2004;101(43):15275-8. Epub Oct. 18, 2004.

(56) References Cited

OTHER PUBLICATIONS

Dittrich et al., Photobleaching and stabilization of. fluorophores used for single-molecule analysis. with one- and two-photon excitation. Applied Physics B. 2001;73(8):829-37.

Donnert et al., Macromolecular-scale resolution in biological fluorescence microscopy. Proc Natl Acad Sci U S A. Aug. 1, 2006;103(31):11440-5. Epub Jul. 24, 2006.

Donnert et al., Major signal increase in fluorescence microscopy through dark-state relaxation. Nat Methods. Jan. 2007;4(1):81-6. Epub Dec. 10, 2006.

Dorval et al., Channel noise is essential for perithreshold oscillations in entorhinal stellate neurons. J Neurosci. Oct. 26, 2005;25(43):10025-8.

Douglas et al., DNA-nanotube-induced alignment of membrane proteins for NMR structure determination. Proc Natl Acad Sci U S A. Apr. 17, 2007;104(16):6644-8. Epub Apr. 2, 2007.

Douglas et al., Self-assembly of DNA into nanoscale three-dimensional shapes. Nature. May 21, 2009;459(7245):414-8. doi: 10.1038/nature08016.

Eggeling et al., Molecular photobleaching kinetics of Rhodamine 6G by one- and two-photon induced confocal fluorescence microscopy. Chemphyschem. May 2005;6(5):791-804.

Eggeling et al., Photobleaching of Fluorescent Dyes under Conditions Used for Single-Molecule Detection: Evidence of Two-Step Photolysis. Anal Chem. Jul. 1, 1998;70(13):2651-9. doi: 10.1021/ac980027p.

Ellis-Davies, Caged compounds: photorelease technology for control of cellular chemistry and physiology. Nat Methods. Aug. 2007;4(8):619-28.

Elshal et al., Multiplex bead array assays: performance evaluation and comparison of sensitivity to ELISA. Methods. Apr. 2006;38(4):317-23.

Epifanovsky et al., The effect of oxidation on the electronic structure of the green fluorescent protein chromophore. J Chem Phys. Mar. 21, 2010;132(11):115104. doi: 10.1063/1.3336425.

Feng et al., Cinnamate-based DNA photolithography. Nat Mater. Aug. 2013;12(8):747-53. doi:10.1038/nmat3645. Epub May 19, 2013.

Fontoura et al., A conserved biogenesis pathway for nucleoporins: proteolytic processing of a 186-kilodalton precursor generates Nup98 and the novel nucleoporin, Nup96. J Cell Biol. Mar. 22, 1999;144(6):1097-112.

Fournier-Bidoz et al., Facile and rapid one-step mass preparation of quantum-dot barcodes. Angew Chem Int Ed Engl. 2008;47(30):5577-81. doi: 10.1002/anie.200800409.

Fujimo et al., Quick, Selective and Reversible Photocrosslinking Reaction between 5-Methylcytosine and 3-Cyanovinylcarbazole in DNA Double Strand. Int J Mol Sci. Mar. 12, 2013;14(3):5765-74. doi:10.3390/ijms14035765.

Fujimoto et al., Site-specific photochemical RNA editing. Chem Commun (Camb). Oct. 28, 2010;46(40):7545-7. doi:10.1039/c0cc03151h. Epub Sep. 17, 2010.

Fukusaki et al., SELEX for tubulin affords specific T-rich DNA aptamers. Systematic evolution of ligands by exponeential enrichment. Bioorg Med Chem Lett. Nov. 19, 2001;11(22):2927-30.

Geiss et al., Direct multiplexed measurement of gene expression with color-coded probe pairs. Nat Biotechnol. Mar. 2008;26(3):317-25. doi: 10.1038/nbt1385. Epub Feb. 17, 2008.

Gerdes et al., Highly multiplexed single-cell analysis of formalin-fixed, paraffin-embedded cancer tissue. Proc Natl Acad Sci U S A. Jul. 16, 2013;110(29):11982-7. doi:10.1073/pnas.1300136110. Epub Jul. 1, 2013.

Ghauharali et al., Fluorescence photobleaching-based image standardization for fluorescence microscopy. J Microscopy. May 2000;198(2):88-100.

Giannone et al., Dynamic superresolution imaging of endogenous proteins on living cells at ultra-high density. Biophys J. Aug. 9, 2010;99(4):1303-10. doi: 10.1016/j.bpj.2010.06.005.

Giepmans et al., The fluorescent toolbox for assessing protein location and function. Science. Apr. 14, 2006;312(5771):217-24.

Gietl et al., DNA origami as biocompatible surface to match single-molecule and ensemble experiments. Nucleic Acids Res. Aug. 2012;40(14):e110. doi: 10.1093/nar/gks326. Epub Apr. 20, 2012.

Gonçalves, Fluorescent labeling of biomolecules with organic probes. Chem Rev. Jan. 2009;109(1):190-212. doi:10.1021/cr0783840.

González et al., Cell-based assays and instrumentation for screening ion-channel targets. Drug Discov Today. Sep. 1994;4(9):431-439.

Görner, Direct and sensitized photoprocesses of bis-benzimidazole dyes and the effects of surfactants and DNA. Photochem Photobiol. Apr. 2001;73(4):339-48.

Grotjohann et al., Diffraction-unlimited all-optical imaging and writing with a photochromic GFP. Nature. Sep. 11, 2011;478(7368):204-8. doi:10.1038/nature10497.

Gudiksen et al., Growth of nanowire superlattice structures for nanoscale photonics and electronics. Nature. Feb. 7, 2002;415(6872):617-20.

Guo et al., Four-color DNA sequencing with 3'-O-modified nucleotide reversible terminators and chemically cleavable fluorescent dideoxynucleotides. Proc Natl Acad Sci U S A. Jul. 8, 2008;105(27):9145-50. doi: 10.1073/pnas.0804023105. Epub Jun. 30, 2008.

Gustafsson et al., Three-dimensional resolution doubling in wide-field fluorescence microscopy by structured illumination. Biophys J. Jun. 2008;94(12):4957-70. doi:10.1529/biophysj.107.120345. Epub Mar. 7, 2008.

Ha et al., Photophysics of fluorescent probes for single-molecule biophysics and super-resolution imaging. Annu Rev Phys Chem. 2012;63:595-617. doi: 10.1146/annurev-physchem-032210-103340. Epub Jan. 30, 2012.

Han et al., Quantum-dot-tagged microbeads for multiplexed optical coding of biomolecules. Nat Biotechnol. Jul. 2001;19(7):631-5.

Heilemann et al., Carbocyanine dyes as efficient reversible single-molecule optical switch. J Am Chem Soc. Mar. 23, 2005;127(11):3801-6.

Hein et al., Stimulated emission depletion (STED) nanoscopy of a fluorescent protein-labeled organelle inside a living cell. Proc Natl Acad Sci U S A. Sep. 23, 2008;105(38):14271-6. doi:10.1073/pnas.0807705105. Epub Sep. 16, 2008.

Heisterkamp et al., Fs-laser scissors for photobleaching, ablation in fixed samples and living cells, and studies of cell mechanics. Methods Cell Biol. 2007;82:293-307.

Hell et al., Breaking the diffraction resolution limit by stimulated emission: stimulated-emission-depletion fluorescence microscopy. Opt Lett. Jun. 1, 2014;19(11):780-2.

Hell, Far-field optical nanoscopy. Science. May 25, 2007;316(5828):1153-8.

Hell, Microscopy and its focal switch. Nat Methods. Jan. 2009;6(1):24-32. doi:10.1038/nmeth.1291.

Henry et al., Real-time measurements of DNA hybridization on microparticles with fluorescence resonance energy transfer. Anal Biochem. Dec. 15, 1999;276(2):204-14.

Hinrichsen et al., The Geometry of Random Sequential Adsorption. J. Stat. Phys. 1986;44(516):793-827.

Hirokawa et al., Kinesin superfamily motor proteins and intracellular transport. Nat Rev Mol Cell Biol. Oct. 2009;10(10):682-96. doi:10.1038/nrm2774.

Holt et al., Subcellular mRNA localization in animal cells and why it matters. Science. Nov. 27, 2009;326(5957):1212-6. doi: 10.1126/science.1176488.

Huang et al., Breaking the diffraction barrier: super-resolution imaging of cells. Cell. Dec. 23, 2010;143(7):1047-58. doi:10.1016/j.cell.2010.12.002.

Huang et al., Three-dimensional super-resolution imaging by stochastic optical reconstruction microscopy. Science. Feb. 8, 2008;319(5864):810-3. doi: 10.1126/science.1153529. Epub Jan. 3, 2008.

Huang et al., Selective photothermal therapy for mixed cancer cells using aptamer-conjugated nanorods. Langmuir. Oct. 21, 2008;24(20):11860-5. doi: 10.1021/la801969c. Epub Sep. 26, 2008.

(56) References Cited

OTHER PUBLICATIONS

Hung et al., Proteomic mapping of the human mitochondrial intermembrane space in live cells via ratiometric APEX tagging. Mol Cell. Jul. 17, 2014;55(2):332-41. doi:10.1016/j.molcel.2014.06.003. Epub Jul. 4, 2014.

Ianoul et al., Near-field scanning fluorescence microscopy study of ion channel clusters in cardiac myocyte membranes. Biophys J. Nov. 2004;87(5):3525-35. Epub Aug. 31, 2004.

Iinuma et al., Polyhedra self-assembled from DNA tripods and characterized with 3D DNA-PAINT. Science. Apr. 4, 2014;344(6179):65-9. doi:10.1126/science.1250944. Epub Mar. 13, 2014.

Ishii et al., Single molecule nanomanipulation of biomolecules. Trends Biotechnol. Jun. 2001;19(6):211-6.

Jenner et al., Crystal structure of the 80S yeast ribosome. Curr Opin Struct Biol. Dec. 2012;22(6):759-67. doi:10.1016/j.sbi.2012.07.013. Epub Aug. 8, 2012. Review.

Johnson-Buck et al., Super-resolution fingerprinting detects chemical reactions and idiosyncrasies of single DNA pegboards. Nano Lett. Feb. 13, 2013;13(2):728-33. doi:10.1021/nl304415b. Epub Jan. 31, 2013.

Jones et al., Fast, three-dimensional super-resolution imaging of live cells. Nat Methods. Jun. 2011;8(6):499-508. doi:10.1038/nmeth.1605. Epub May 8, 2011.

Jones et al., Nanomaterials. Programmable materials and the nature of the DNA bond. Science. Feb. 20, 2015;347(6224):1260901. doi:10.1126/science.1260901.

Joo et al., Advances in single-molecule fluorescence methods for molecular biology. Annu Rev Biochem. 2008;77:51-76. doi:10.1146/annurev.biochem.77.070606.101543.

Ju et al., Four-color DNA sequencing by synthesis using cleavable fluorescent nucleotide reversible terminators. Proc Natl Acad Sci U S A. Dec. 26, 2006;103(52):19635-40. Epub Dec. 14, 2006.

Juette et al., Three-dimensional sub-100 nm resolution fluorescence microscopy of thick samples. Nat Methods. Jun. 2008;5(6):527-9. doi: 10.1038/nmeth.1211. Epub May 11, 2008.

Jungmann et al., Multiplexed 3D cellular super-resolution imaging with DNA-PAINT and Exchange-PAINT. Nat Methods. Mar. 2014;11(3):313-8. doi: 10.1038/nmeth.2835. Epub Feb. 2, 2014.

Jungmann et al., Multiplexed 3D cellular super-resolution imaging with DNA-PAINT and Exchange-PAINT. Nat Methods. Mar. 2014;11(3):313-8. doi: 10.1038/nmeth.2835. Epub Feb. 2, 2014. Supplementary Text and Figures. XP-002775144. 38 pages.

Jungmann et al., Nanoscale imaging in DNA nanotechnology. Wiley Interdiscip Rev Nanomed Nanobiotechnol. Jan.-Feb. 2012;4(1):66-81. doi:10.1002/wnan.173. Epub Nov. 23, 2011.

Jungmann et al., Single-molecule kinetics and super-resolution microscopy by fluorescence imaging of transient binding on DNA origami. Nano Lett. Nov. 10, 2010;10(11):4756-61.

Kalies et al., Mechanisms of high-order photobleaching and its relationship to intracellular ablation. Biomed Opt Express. Mar. 4, 2011;2(4):805-16. doi:10.1364/BOE.2.000816.

Kao et al., Tracking of single fluorescent particles in three dimensions: use of cylindrical optics to encode particle position. Biophys J. Sep. 1994;67(3):1291-300.

Kato et al., High-resolution structural analysis of a DNA nanostructure by cryoEM. Nano Lett. Jul. 2009;9(7):2747-50. doi: 10.1021/nl901265n.

Ke et al., DNA brick crystals with prescribed depths. Nat Chem. Nov. 2014;6(11):994-1002. doi: 10.1038/nchem.2083. Epub Oct. 19, 2014.

Ke et al., Self-Assembled Water-Soluble Nucleic Acid Probe Tiles for Label-Free RNA Hybridization Assays. Science. Jan. 11, 2008;319(5860):180-3.

Ke et al., Three-dimensional structures self-assembled from DNA bricks. Science. Nov. 30, 2012;338(6111):1177-83. doi: 10.1126/science.1227268.

Kole et al., Action potential generation requires a high sodium channel density in the axon initial segment. Nat Neurosci. Feb. 2008;11(2):178-86. doi: 10.1038/nn2040. Epub Jan. 20, 2008.

Kuetemeyer et al., Influence of laser parameters and staining on femtosecond laser-based intracellular nanosurgery. Biomed Opt Express. Aug. 10, 2010;1(2):587-597.

Lee et al., The double-helix microscope super-resolves extended biological structures by localizing single blinking molecules in three dimensions with nanoscale precision. Appl Phys Lett. Apr. 9, 2012;100(15):153701-1537013.

Lehr et al., Real-time detection of nucleic acid interactions by total internal reflection fluorescence. Anal Chem. May 15, 2003;75(10):2414-20.

Levskaya et al., Spatiotemporal control of cell signalling using a light-switchable protein interaction. Nature. Oct. 15, 2009;461(7266):997-1001. doi: 10.1038/nature08446. Epub Sep. 13, 2009.

Levsky et al., Fluorescence in situ hybridization: past, present and future. J Cell Sci. Jul. 15, 2003;116(Pt 14):2833-8.

Levsky et al., Single-cell gene expression profiling. Science. Aug. 2, 2002;297(5582):836-40.

Lew et al., Three-dimensional superresolution colocalization of intracellular protein superstructures and the cell surface in live Caulobacter crescentus. Proc Natl Acad Sci U S A. Nov. 15, 2011;108(46):E1102-10. doi: 10.1073/pnas.1114444108. Epub Oct. 26, 2011.

Li et al., Controlled fabrication of fluorescent barcode nanorods. ACS Nano. Aug. 24, 2010;4(8):4350-60. doi: 10.1021/nn9017137.

Li et al., Multiplexed detection of pathogen DNA with DNA-based fluorescence nanobarcodes. Nat Biotechnol. Jul. 2005;23(7):885-9. Epub Jun. 12, 2005.

Lichtman et al., Fluorescence microscopy. Nat Methods. Dec. 2005;2(12):910-9.

Lin et al., Designer DNA nanoarchitectures. Biochemistry. Mar. 3, 2009;48(8):1663-74. doi: 10.1021/bi802324w.

Lin et al., Functional DNA nanotube arrays: bottom-up meets top-down. Angewandte Chemie. 2007;119(32):6201-4.

Lin et al., Self-assembled combinatorial encoding nanoarrays for multiplexed biosensing. Nano Lett. Feb. 2007;7(2):507-12.

Lin et al., Submicrometre geometrically encoded fluorescent barcodes self-assembled from DNA. Nat Chem. Oct. 2012;4(10):832-9.

Liu et al., Aptamer-directed self-assembly of protein arrays on a DNA nanostructure. Angew Chem Int Ed Engl. Jul. 11, 2005;44(28):4333-8.

Livet et al., Transgenic strategies for combinatorial expression of fluorescent proteins in the nervous system. Nature. Nov. 1, 2007;450(7166):56-62.

Lubeck et al., Single-cell in situ RNA profiling by sequential hybridization. Nat Methods. Apr. 2014;11(4):360-1. doi:10.1038/nmeth.2892.

Lubeck et al., Single-cell systems biology by super-resolution imaging and combinatorial labeling. Nat Methods. Jun. 3, 2012;9(7):743-8. doi:10.1038/nmeth.2069.

Lusic et al., Improved synthesis of the two-photon caging group 3-nitro-2-ethyldibenzofuran and its application to a caged thymidine phosphoramidite. Org Lett. Mar. 5, 2010;12(5):916-9. doi:10.1021/ol902807q.

Mag et al., Synthesis and selective cleavage of an oligodeoxynucleotide containing a bridged internucleotide 5'-phosphorothioate linkage. Nucleic Acids Res. Apr. 11, 1991;19(7):1437-41.

Manfrinato et al., Determining the resolution limits of electron-beam lithography: direct measurement of the point-spread function. Nano Lett. Aug. 13, 2014;14(8):4406-12. doi:10.1021/nl5013773. Epub Jun. 30, 2014.

Manning, The molecular theory of polyelectrolyte solutions with applications to the electrostatic properties of polynucleotides. Q Rev Biophys. May 1978;11(2):179-246.

Marcon et al., 'On-the-fly' optical encoding of combinatorial peptide libraries for profiling of protease specificity. Mol Biosyst. Jan. 2010;6(1):225-33. doi: 10.1039/b909087h. Epub Oct. 6, 2009.

Martell et al., Engineered ascorbate peroxidase as a genetically encoded reporter for electron microscopy. Nat Biotechnol. Nov. 2012;30(11):1143-8. doi:10.1038/nbt.2375. Epub Oct. 21, 2012.

(56) References Cited

OTHER PUBLICATIONS

Martin, Functional Synthetic DNA Nanostructures. Dissertation. Technische Universität München, Laboratory for Biomolecular Nanotechnology. Filed on Mar. 12, 2013.
Mathieu et al., Six-helix bundles designed from DNA. Nano Lett. Apr. 2005;5(4):661-5.
Mei et al., Stability of DNA origami nanoarrays in cell lysate. Nano Lett. Apr. 13, 2011;11(4):1477-82. doi: 10.1021/nl1040836. Epub Mar. 2, 2011.
Meserve et al., A double-stranded molecular probe for homogeneous nucleic acid analysis. Analyst. Aug. 2008;133(8):1013-9. doi:10.1039/b804853c. Epub Jun. 6, 2008.
Michel et al., Optical study of DNA surface hybridization reveals DNA surface density as a key parameter for microarray hybridization kinetics. Biophys J. Feb. 1, 2007;92(3):999-1004. Epub Nov. 3, 2006.
Mittag et al., Sequential photobleaching of fluorochromes for polychromatic slide-based cytometry. Cytometry A. Mar. 2006;69(3):139-41.
Myhrvold et al., Isothermal self-assembly of complex DNA structures under diverse and biocompatible conditions. Nano Lett. Sep. 11, 2013;13(9):4242-8. doi: 10.1021/nl4019512. Epub Aug. 26, 2013.
Nannenga et al., High-resolution structure determination by continuous-rotation data collection in MicroED. Nat Methods. Sep. 2014;11(9):927-30. doi: 10.1038/nmeth.3043. Epub Aug. 3, 2014.
Nannenga et al., Protein structure determination by MicroED. Curr Opin Struct Biol. Aug. 2014;27:24-31. doi: 10.1016/j.sbi.2014.03.004. Epub Apr. 5, 2014.
Nicewarner-Pena et al., Submicrometer metallic barcodes. Science. Oct. 5, 2011;294(5540):137-41.
Nikogosyan et al., Two-photon ionization and dissociation of liquid water by powerful laser UV radiation. Chem Phys. 1983;77(1):131-43.
Olejnik et al., Photocleavable biotin derivatives: a versatile approach for the isolation of biomolecules. Proc Natl Acad Sci U S A. Aug. 1, 1995;92(16):7590-4.
Ormöet al., Crystal structure of the Aequorea victoria green fluorescent protein. Science. Sep. 6, 1996;273(5280):1392-5.
Paige et al., Fluorescence imaging of cellular metabolites with RNA. Science. Mar. 9, 2012;335(6073):1194. doi:10.1126/science.1218298.
Paige et al., RNA mimics of green fluorescent protein. Science. Jul. 29, 2011;333(6042):642-6. doi:10.1126/science.1207339.
Patterson et al., Photobleaching in two-photon excitation microscopy. Biophys J. Apr. 2000;78(4):2159-62.
Pavani et al., Three dimensional tracking of fluorescent microparticles using a photon-limited double-helix response system. Opt Express. Dec. 22, 2008;16(26):22048-57.
Pavani et al., Three-dimensional, single-molecule fluorescence imaging beyond the diffraction limit by using a double-helix point spread function. Proc Natl Acad Sci U S A. Mar. 3, 2009;106(9):2995-9. doi: 10.1073/pnas.0900245106. Epub Feb. 11, 2009.
Pertsinidis et al., Subnanometre single-molecule localization, registration and distance measurements. Nature. Jul. 29, 2010;466(7306):647-51. doi:10.1038/nature09163. Epub Jul. 7, 2010.
Petruska et al., Enthalpy-entropy compensation in DNA melting thermodynamics. J Biol Chem. Jan. 13, 1995;270(2):746-50.
Piestun et al., Propagation-invariant wave fields with finite energy. J Opt Soc Am A Opt Image Sci Vis. Feb. 2000;17(2):294-303.
Pinheiro et al., Challenges and opportunities for structural DNA nanotechnology. Nat Nanotechnol. Nov. 6, 2011;6(12):763-72. doi:10.1038/nnano.2011.187.
Raj et al., Imaging individual mRNA molecules using multiple singly labeled probes. Nat Methods. Oct. 2008;5(10):877-9. doi: 10.1038/nmeth.1253. Epub Sep. 21, 2008.
Rajendran et al., Selection of fluorescent aptamer beacons that light up in the presence of zinc. Anal Bioanal Chem. Feb. 2008;390(4):1067-75. Epub Nov. 30, 2007.
Ram et al., A novel approach to determining the three-dimensional location of microscopic objects with applications to 3D particle tracking. Proc SPIE. Feb. 14, 2010;6443:7 pages.
Rasnik et al., Nonblinking and long-lasting single-molecule fluorescence imaging. Nat Methods. Nov. 2006;3(11):891-3. Epub Oct. 1, 2006.
Record et al., Thermodynamic analysis of ion effects on the binding and conformational equilibria of proteins and nucleic acids: the roles of ion association or release, screening, and ion effects on water activity. Q Rev Biophys. May 1978;11(2):103-78.
Redmond et al., Excited State Relaxation in Cyanine Dyes: A Remarkably Efficient Reverse Intersystem Crossing from Upper Triplet Levels. J Phys Chem. 1997;101(15):2773-7.
Reindl et al., Higher excited-state triplet-singlet intersystem crossing of some organic dyes. Chem Phys. Nov. 1, 1996;211(1-3):431-9.
Resch-Genger et al., Quantum dots versus organic dyes as fluorescent labels. Nat Methods. Sep. 2008;5(9):763-75. doi: 10.1038/nmeth.1248.
Reuther et al., Primary Photochemical Processes in Thymine in Concentrated Aqueous Solution Studied by Femtosecond UV Spectroscopy. J Chem Phys. 1996;100(13):5570-7.
Rhee et al., Proteomic mapping of mitochondria in living cells via spatially restricted enzymatic tagging. Science. Mar. 15, 2013;339(6125):1328-31. doi: 10.1126/science.1230593. Epub Jan. 31, 2013.
Ries et al., A simple, versatile method for GFP-based super-resolution microscopy via nanobodies. Nat Methods. Jun. 2012;9(6):582-4. doi: 10.1038/nmeth.1991. Epub Apr. 29, 2012.
Ringemann et al., Enhancing fluorescence brightness: effect of reverse intersystem crossing studied by fluorescence fluctuation spectroscopy. Chemphyschem. Mar. 14, 2008;9(4):612-24. doi:10.1002/cphc.200700596.
Rinker et al., Self-assembled DNA nanostructures for distance-dependent multivalent ligand-protein binding. Nat Nanotechnol. Jul. 2008;3(7):418-22. doi: 10.1038/nnano.2008.164. Epub Jun. 22, 2008.
Rodgers et al., Transient association of Ku with nuclear substrates characterized using fluorescence photobleaching. J Immunol. Mar. 1, 2002;168(5):2348-55.
Rosi et al., Nanostructures in biodiagnostics. Chem Rev. Apr. 2005;105(4):1547-62.
Rothemund, Folding DNA to create nanoscale shapes and patterns. Nature. Mar. 16, 2006;440(7082):297-302.
Rust et al., Sub-diffraction-limit imaging by stochastic optical reconstruction microscopy (STORM). Nat Methods. Oct. 2006;3(10):793-5. Epub Aug. 9, 2006.
Ruuckmann et al., On the Influence of Higher Excited States on the ISC Quantum Yield of Octa-aL-alkyloxy-substituted Zn-Phthalocyanine Molecules Studied by Nonlinear Absorption. Photochem Photobiol. Nov. 1997;66(5):576-84.
Sabanayagam et al., Long time scale blinking kinetics of cyanine fluorophores conjugated to DNA and its effect on Förster resonance energy transfer. J Chem Phys. Dec. 8, 2005;123(22):224708.
Sadowski et al., Developmental self-assembly of a DNA tetrahedron. ACS Nano. Apr. 22, 2014;8(4):3251-9. doi:10.1021/nn4038223. Epub Apr. 11, 2014.
Santalucia, A unified view of polymer, dumbbell, and oligonucleotide DNA nearest-neighbor thermodynamics. Proc Natl Acad Sci U S A. Feb. 17, 1998;95(4):1460-5.
Sasmal et al., Single-molecule patch-clamp FRET microscopy studies of NMDA receptor ion channel dynamics in living cells: revealing the multiple conformational states associated with a channel at its electrical off state. J Am Chem Soc. Sep. 17, 2014;136(37):12998-3005. doi:10.1021/ja506231j. Epub Sep. 5, 2014.
Schmidt et al., A fully genetically encoded protein architecture for optical control of peptide ligand concentration. Nat Commun. 2014;5:3019. doi:10.1038/ncomms4019.
Schmied et al., DNA origami-based standards for quantitative fluorescence microscopy. Nat Protoc. 2014;9(6):1367-91. doi: 10.1038/nprot.2014.079. Epub May 15, 2014.

(56) References Cited

OTHER PUBLICATIONS

Schmied et al., Fluorescence and super-resolution standards based on DNA origami. Nat Methods. Dec. 2012;9(12):1133-4. doi: 10.1038/nmeth.2254.
Schneidman et al., Ion channel stochasticity may be critical in determining the reliability and precision of spike timing. Neural Comput. Oct. 1, 1998;10(7):1679-703.
Schubert et al., Analyzing proteome topology and function by automated multidimensional fluorescence microscopy. Nat Biotechnol. Oct. 2006;24(10):1270-8. Epub Oct. 1, 2006.
Schweller et al., Multiplexed in situ immunofluorescence using dynamic DNA complexes. Angew Chem Int Ed Engl. Sep. 10, 2012;51(37):9292-6. doi:10.1002/anie.201204304. Epub Aug. 15, 2012.
Seeman, Nucleic acid junctions and lattices. J Theor Biol. Nov. 21, 1982;99(2):237-47.
Sharonov et al., Wide-field subdiffraction imaging by accumulated binding of diffusing probes. Proc Natl Acad Sci U S A. Dec. 12, 2006;103(50):18911-6. Epub Dec. 1, 2006.
Shi et al., Three-dimensional electron crystallography of protein microcrystals. Elife. Nov. 19, 2013;2:e01345. doi:10.7554/eLife.01345.
Shi, A glimpse of structural biology through X-ray crystallography. Cell. Nov. 20, 2014;159(5):995-1014. doi: 10.1016/j.cell.2014.10.051.
Shigeno et al., Quick regulation of mRNA functions by a few seconds of photoirradiation. Org Biomol Chem. Oct. 14, 2012;10(38):7820-5. doi: 10.1039/c2ob25883h.
Shuai et al., Optimal ion channel clustering for intracellular calcium signaling. Proc Natl Acad Sci U S A. Jan. 21, 2003;100(2):506-10. Epub Jan. 7, 2003.
Smith et al., Fast, single-molecule localization that achieves theoretically minimum uncertainty. Nat Methods. May 2010;7(5):373-5. doi: 10.1038/nmeth.1449. Epub Apr. 4, 2010.
Song et al., Influence of the triplet excited state on the photobleaching kinetics of fluorescein in microscopy. Biophys J. Jun. 1996;70(6):2959-68.
Steinhauer et al., DNA origami as a nanoscopic ruler for super-resolution microscopy. Angew Chem Int Ed Engl. 2009;48(47):8870-3. doi: 10.1002/anie.200903308.
Stoltenburg et al., SELEX—a (r)evolutionary method to generate high-affinity nucleic acid ligands. Biomol Eng. Oct. 2007;24(4):381-403. Epub Jun. 16, 2007.
Szilard, On the decrease of entropy in a thermodynamic system by the intervention of intelligent beings. Zeitschrift fur Physik. 1929;53:840.
Tadross et al., Ca2+ channel nanodomains boost local Ca2+ amplitude. Proc Natl Acad Sci U S A. Sep. 24, 2013;110(39):15794-9. doi:10.1073/pnas.1313898110. Epub Sep. 9, 2013.
Tirlapur et al., Femtosecond near-infrared laser pulses elicit generation of reactive oxygen species in mammalian cells leading to apoptosis-like death. Exp Cell Res. Feb. 1, 2001;263(1):88-97.
Tokumura et al., Reverse intersystem crossing from higher triplet to excited singlet in 2,2'-bipyridine-3,3'-diol phototautomer. J Photochem Photobiol. Aug. 2, 1994;81(3):151-8.
Tokunaga et al., Highly inclined thin illumination enables clear single-molecule imaging in cells. Nat Methods. Feb. 2008;5(2):159-61. doi: 10.1038/nmeth1171. Epub Jan. 6, 2008. Erratum in: Nat Methods. May 2008;5(5):455.
Torquato et al., Random sequential addition of hard spheres in high Euclidean dimensions. Phys Rev E Stat Nonlin Soft Matter Phys. Dec. 2006;74(6 Pt 1):061308. Epub Dec. 20, 2006.
Tørring et al., DNA origami: a quantum leap for self-assembly of complex structures. Chem Soc Rev. Dec. 2011;40(12):5636-46. doi: 10.1039/c1cs15057j. Epub May 19, 2011.
Toyabe et al., Experimental demonstration of information-to-energy conversion and validation of the generalized Jarzynski equality. Nature Phys. 2010;6:988-92.
Tsien, The green fluorescent protein. Annu Rev Biochem. 1998;67:509-44.

Uno et al., A spontaneously blinking fluorophore based on intramolecular spirocyclization for live-cell super-resolution imaging. Nat Chem. Aug. 2014;6(8):681-9. doi: 10.1038/nchem.2002. Epub Jul. 20, 2014.
Vale, The molecular motor toolbox for intracellular transport. Cell. Feb. 21, 2003;112(4):467-80.
Van De Linde et al., Direct stochastic optical reconstruction microscopy with standard fluorescent probes. Nat Protoc. Jun. 16, 2011;6(7):991-1009. doi:10.1038/nprot.2011.336.
Van Den Berg et al., Molecular motors in cargo trafficking and synapse assembly. Adv Exp Med Biol. 2012;970:173-96. doi:10.1007/978-3-7091-0932-8_8.
Vaughan et al., Phosphine quenching of cyanine dyes as a versatile tool for fluorescence microscopy. J Am Chem Soc. Jan. 30, 2013;135(4):1197-200. doi: 10.1021/ja3105279. Epub Jan. 17, 2013.
Vaughan et al., Ultrabright photoactivatable fluorophores created by reductive caging. Nat Methods. Dec. 2012;9(12):1181-4. doi: 10.1038/nmeth.2214. Epub Oct. 28, 2012.
Vieregg et al., Selective nucleic acid capture with shielded covalent probes. J Am Chem Soc. Jul. 3, 2013;135(26):9691-9. doi:10.1021/ja4009216. Epub Jun. 18, 2013.
Von Middendorff et al., Isotropic 3D Nanoscopy based on single emitter switching. Opt Express. Dec. 8, 2008;16(25):20774-88.
Wahlby et al., Sequential immunofluorescence staining and image analysis for detection of large numbers of antigens in individual cell nuclei. Cytometry. Jan. 1, 2002;47(1):32-41.
Wang et al., Prototyping nanorod control: A DNA double helix sheathed within a DNA six-helix bundle. Chem Biol. Aug. 28, 2009;16(8):862-7. doi: 10.1016/j.chembiol.2009.07.008.
Wei et al., Complex shapes self-assembled from single-stranded DNA tiles. Nature. May 30, 2012;485(7400):623-6. doi: 10.1038/nature11075.
Weiss, Fluorescence spectroscopy of single biomolecules. Science. Mar. 12, 1999;283(5408):1676-83.
White et al., Noise from voltage-gated ion channels may influence neuronal dynamics in the entorhinal cortex. J Neurophysiol. Jul. 1998;80(1):262-9.
Widengren et al., Strategies to improve photostabilities in ultrasensitive fluorescence spectroscopy. J Phys Chem A. Jan. 25, 2007;111(3):429-40.
Willig et al., Nanoscale resolution in GFP-based microscopy. Nat Methods. Sep. 2006;3(9):721-3.
Wilner et al., Covalently linked DNA nanotubes. Nano Lett. Apr. 14, 2010;10(4):1458-65.
Winfree et al., Design and self-assembly of two-dimensional DNA crystals. Nature. Aug. 6, 1998;394(6693):539-44.
Wlodawer et al., Protein crystallography for aspiring crystallographers or how to avoid pitfalls and traps in macromolecular structure determination. FEBS J. Nov. 2013;280(22):5705-36. doi:10.1111/febs.12495. Epub Sep. 18, 2013.
Wörner et al., Following a chemical reaction using high-harmonic interferometry. Nature. Jul. 29, 2010;466(7306):604-7. doi: 10.1038/nature09185.
Xiao et al., Direct determination of haplotypes from single DNA molecules. Nat Methods. Mar. 2009;6(3):199-201. doi:10.1038/nmeth.1301. Epub Feb. 8, 2009.
Xu et al., Multiplexed SNP genotyping using the Qbead system: a quantum dot-encoded microsphere-based assay. Nucleic Acids Res. Apr. 15, 2003;31(8):e43.
Yang et al., Nanostructures as Programmable Biomolecular Scaffolds. Bioconjug Chem. Aug. 19, 2015;26(8):1381-95. doi:10.1021/acs.bioconjchem.5b00194. Epub May 22, 2015.
Yin et al., Programming biomolecular self-assembly pathways. Nature. Jan. 17, 2008;451(7176):318-22. doi:10.1038/nature06451.
Yin et al., Programming DNA tube circumferences. Science. Aug. 8, 2008;321(5890):824-6. doi:10.1126/science.1157312.
Yoshimura et al., Ultrafast reversible photo-cross-linking reaction: toward in situ DNA manipulation. Org Lett. Aug. 7, 2008;10(15):3227-30. doi:10.1021/ol801112j. Epub Jun. 27, 2008.
Yurke et al., A DNA-fuelled molecular machine made of DNA. Nature. Aug. 10, 2000;406(6796):605-8.

(56) References Cited

OTHER PUBLICATIONS

Zadeh et al., NUPACK: Analysis and design of nucleic acid systems. J Comput Chem. Jan. 15, 2011;32(1):170-3. doi:10.1002/jcc.21596.
Zhang et al., Dynamic DNA nanotechnology using strand-displacement reactions. Nat Chem. Feb. 2011;3(2):103-13. doi: 10.1038/nchem.957.
Zhang et al., Structural DNA nanotechnology: state of the art and future perspective. J Am Chem Soc. Aug. 13, 2014;136(32):11198-211. doi:10.1021/ja505101a. Epub Jul. 28, 2014.
Zhao et al., Advances of multiplex and high throughput biomeolecular detection technologies based on encoding microparticles. Science China Chemistry. 2011;54(8):1185-1201.
Zheng et al., From molecular to macroscopic via the rational design of a self-assembled 3D DNA crystal. Nature. Sep. 3, 2009;461(7260):74-7. doi:10.1038/nature08274.
Zhong et al., Femtosecond Real-Time Probing of Reactions. 23. Studies of Temporal, Velocity, Angular, and State Dynamics from Transition States to Final Products by Femtosecond-Resolved Mass Spectrometry. J Phys Chem. 1998;102(23):4031-58.

* cited by examiner

Fig. 5D

SEQUENCE LISTING

<160> NUMBER OF SEQ ID NOS: 361

<210> SEQ ID NO 1
<211> LENGTH: 7308
<212> TYPE: DNA
<213> ORGANISM: Artificial Sequence
<220> FEATURE:
<223> OTHER INFORMATION: SCAFFOLD STRAND

<400> SEQUENCE: 1

```
aatgctacta ctattagtag aattgatgcc acctttcag ctcgcgcccc aaatgaaaat        60
atagctaaac aggttattga ccatttgcga aatgtatcta atggtcaaac taaatctact       120
cgttcgcaga attgggaatc aactgttata tggaatgaaa cttccagaca ccgtacttta       180
gttgcatatt taaaacatgt tgagctacag cattatattc agcaattaag ctctaagcca       240
tccgcaaaaa tgacctctta tcaaaaggag caattaaagg tactctctaa tcctgacctg       300
ttggagtttg cttccggtct ggttcgcttt gaagctcgaa ttaaaacgcg atatttgaag       360
tctttcgggc ttcctcttaa tcttttgat gcaatccgct ttgcttctga ctataatagt       420
cagggtaaag acctgatttt tgatttatgg tcattctcgt tttctgaact gtttaaagca       480
tttgaggggg attcaatgaa tatttatgac gattccgcag tattggacgc tatccagtct       540
aaacatttta ctattacccc ctctggcaaa acttcttttg caaaagcctc tcgctatttt       600 ggttttatc gtcgtctggt aaacgagggt tatgatagtg ttgctcttac tatgcctcgt       660 aattccttt ggcgttatgt atctgcatta gttgaatgtg gtattcctaa atctcaactg       720
atgaatcttt ctacctgtaa taatgttgtt ccgttagttc gttttattaa cgtagatttt       780
tcttcccaac gtcctgactg gtataatgag ccagttctta aaatcgcata aggtaattca       840
caatgattaa agttgaaatt aaaccatctc aagcccaatt tactactcgt tctggtgttt       900
ctcgtcaggg caagccttat tcactgaatg agcagctttg ttacgttgat ttgggtaatg       960
aatatccggt tcttgtcaag attactcttg atgaaggtca gccagcctat gcgcctggtc      1020
tgtacaccgt tcatctgtcc tctttcaaag ttggtcagtt cggttccctt atgattgacc      1080
gtctgcgcct cgttccggct aagtaacatg gagcaggtcg cggatttcga cacaatttat      1140
caggcgatga tacaaatctc cgttgtactt tgtttcgcgc ttggtataat cgctgggggt      1200
caaagatgag tgttttagtg tattcttttg cctctttcgt tttaggttgg tgccttcgta      1260
```

```
gtggcattac gtattttacc cgtttaatgg aaacttcctc atgaaaaagt ctttagtcct    1320
caaagcctct gtagccgttg ctaccctcgt tccgatgctg tctttcgctg ctgagggtga    1380
cgatcccgca aaagcggcct ttaactccct gcaagcctca gcgaccgaat atatcggtta    1440
tgcgtgggcg atggttgttg tcattgtcgg cgcaactatc ggtatcaagc tgtttaagaa    1500
attcacctcg aaagcaagct gataaaccga tacaattaaa ggctccttt  ggagcctttt    1560 ttttggagat tttcaacgtg aaaaaattat tattcgcaat tcctttagtt gttcctttct    1620
attctcactc cgctgaaact gttgaaagtt gtttagcaaa atcccataca gaaaattcat    1680
ttactaacgt ctggaaagac gacaaaactt tagatcgtta cgctaactat gagggctgtc    1740
tgtggaatgc tacaggcgtt gtagtttgta ctggtgacga aactcagtgt tacggtacat    1800
gggttcctat tgggcttgct atccctgaaa atgagggtgg tggctctgag ggtggcggtt    1860
ctgagggtgg cggttctgag ggtggcggta ctaaacctcc tgagtacggt gatacaccta    1920
ttccgggcta tacttatatc aaccctctcg acggcactta tccgcctggt actgagcaaa    1980
accccgctaa tcctaatcct tctcttgagg agtctcagcc tcttaatact ttcatgtttc    2040
agaataatag gttccgaaat aggcaggggg cattaactgt ttatacgggc actgttactc    2100
aaggcactga ccccgttaaa acttattacc agtacactcc tgtatcatca aaagccatgt    2160
atgacgctta ctggaacggt aaattcagag actgcgcttt ccattctggc tttaatgagg    2220
atttatttgt ttgtgaatat caaggccaat cgtctgacct gcctcaacct cctgtcaatg    2280
ctggcggcgg ctctggtggt ggttctggtg gcggctctga gggtggtggc tctgagggtg    2340
gcggttctga gggtggcggc tctgagggag gcggttccgg tggtggctct ggttccggtg    2400
attttgatta tgaaaagatg gcaaacgcta ataaggggc  tatgaccgaa aatgccgatg    2460
aaaacgcgct acagtctgac gctaaaggca aacttgattc tgtcgctact gattacggtg    2520
ctgctatcga tggtttcatt ggtgacgttt ccggccttgc taatggtaat ggtgctactg    2580
gtgattttgc tggctctaat cccaaatggc tcaagtcgg  tgacggtgat aattcacctt    2640
taatgaataa tttccgtcaa tatttacctt ccctccctca atcggttgaa tgtcgccctt    2700 ttgtcttttgg cgctggtaaa ccatatgaat tttctattga ttgtgacaaa ataaacttat    2760
tccgtggtgt ctttgcgttt cttttatatg ttgccacctt tatgtatgta ttttctacgt    2820
ttgctaacat actgcgtaat aaggagtctt aatcatgcca gttcttttgg gtattccgtt    2880
attattgcgt ttcctcggtt ccttctggt  aactttgttc ggctatctgc ttacttttct    2940
taaaaagggc ttcggtaaga tagctattgc tatttcattg tttcttgctc ttattattgg    3000
gcttaactca attcttgtgg gttatctctc tgatattagc gctcaattac cctctgactt    3060
tgttcagggt gttcagttaa ttctcccgtc taatgcgctt ccctgttttt atgttattct    3120
ctctgtaaag gctgctattt tcatttttga cgttaaacaa aaaatcgttt cttatttgga    3180
ttgggataaa taatatggct gtttattttg taactggcaa attaggctct ggaaagacgc    3240
tcgttagcgt tggtaagatt caggataaaa ttgtagctgg gtgcaaaata gcaactaatc    3300
ttgatttaag gcttcaaaac ctcccgcaag tcgggaggtt cgctaaaacg cctcgcgttc    3360
ttagaatacc ggataagcct tctatatctg atttgcttgc tattgggcgc ggtaatgatt    3420
cctacgatga aaataaaaac ggcttgcttg ttctcgatga gtgcggtact tggtttaata    3480
cccgttcttg gaatgataag gaaagacagc cgattattga ttggtttcta catgctcgta    3540
aattaggatg ggatattatt tttcttgttc aggacttatc tattgttgat aaacaggcgc    3600
```

```
gttctgcatt agctgaacat gttgtttatt gtcgtcgtct ggacagaatt actttacctt    3660
ttgtcggtac tttatattct cttattactg gctcgaaaat gcctctgcct aaattacatg    3720
ttggcgttgt taaatatggc gattctcaat taagccctac tgttgagcgt tggctttata    3780
ctggtaagaa tttgtataac gcatatgata ctaaacaggc ttttctagt aattatgatt     3840 ccggtgttta ttcttattta acgccttatt tatcacacgg tcggtatttc aaaccattaa    3900
atttaggtca gaagatgaaa ttaactaaaa tatatttgaa aaagttttct cgcgttcttt    3960
gtcttgcgat tggatttgca tcagcattta catatagtta tataacccaa cctaagccgg    4020
aggttaaaaa ggtagtctct cagacctatg attttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgtttcca    4200
ttaaaaaagg taattcaaat gaaattgtta aatgtaatta attttgtttt cttgatgttt    4260
gtttcatcat cttcttttgc tcaggtaatt gaaatgaata attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
gttttacgtg caaataattt tgatatggta ggttctaacc cttccattat tcagaagtat    4500
aatccaaaca atcaggatta tattgatgaa ttgccatcat ctgataatca ggaatatgat    4560
gataattccg ctccttctgg tggttttctt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg ctctaatct attagttgtt     4740 agtgctccta aagatatttt agataaacctt cctcaattcc tttcaactgt tgatttgcca    4800
actgaccaga tattgattga gggttttgata tttgaggttc agcaaggtga tgctttagat    4860
ttttcatttg ctgctggctc tcagcgtggc actgttgcag gcggtgttaa tactgaccgc    4920
ctcacctctg ttttatcttc tgctggtggt tcgttcggta ttttttaatgg cgatgttta    4980 gggctatcag ttcgcgcatt aaagactaat agccattcaa aaatattgtc tgtgccacgt    5040
attcttacgc tttcaggtca gaagggttct atctctgttg gccagaatgt ccctttttatt    5100 actggtcgtg tgactggtga atctgccaat gtaaataatc catttcagac gattgagcgt    5160
caaaatgtag gtatttccat gagcgttttt cctgttgcaa tggctggcgg taatattgtt    5220
ctggatatta ccagcaaggc cgatagtttg agttcttcta ctcaggcaag tgatgttatt    5280
actaatcaaa gaagtattgc tacaacggtt aatttgcgtg atggacagac tcttttactc    5340
ggtggcctca ctgattataa aaacacttct caggattctg gcgtaccgtt cctgtctaaa    5400
atccctttaa tcggcctcct gtttagctcc cgctctgatt ctaacgagga aagcacgtta    5460
tacgtgctcg tcaaagcaac catagtacgc gccctgtagc ggcgcattaa gcgcggcggg    5520
tgtggtggtt acgcgcagcg tgaccgctac acttgccagc gccctagcgc ccgctccttt    5580
cgctttcttc ccttcctttc tcgccacgtt cgccggcttt cccgtcaag ctctaaatcg     5640 ggggctccct ttagggttcc gatttagtgc tttacggcac ctcgacccca aaaaacttga    5700
tttgggtgat ggttcacgta gtgggccatc gccctgatag acggtttttc gccctttgac    5760
gttggagtcc acgttcttta atagtggact cttgttccaa actggaacaa cactcaaccc    5820
tatctcgggc tattcttttg atttataagg gattttgccg atttcggaac caccatcaaa    5880
caggattttc gcctgctggg gcaaaccagc gtggaccgct tgctgcaact ctctcagggc    5940
caggcggtga agggcaatca gctgttgccc gtctcactgg tgaaaagaaa aaccaccctg    6000
```

```
gcgcccaata cgcaaaccgc ctctccccgc gcgttggccg attcattaat gcagctggca    6060
cgacaggttt cccgactgga aagcgggcag tgagcgcaac gcaattaatg tgagttagct    6120
cactcattag gcaccccagg ctttacactt tatgcttccg gctcgtatgt tgtgtggaat    6180
tgtgagcgga taacaatttc acacaggaaa cagctatgac catgattacg aattcgagct    6240
cggtacccgg ggatccttat acgggtacta gccatgcgta tacggtcgct agcggacttg    6300
cctcgctatc aaaggtctag agtcgacctg caggcatgca agcttggcac tggccgtcgt    6360
tttacaacgt cgtgactggg aaaaccctgg cgttacccaa cttaatcgcc ttgcagcaca    6420
tccccctttc gccagctggc gtaatagcga agaggcccgc accgatcgcc cttcccaaca    6480
gttgcgcagc ctgaatggcg aatggcgctt tgcctggttt ccggcaccag aagcggtgcc    6540
ggaaagctgg ctggagtgcg atcttcctga ggccgatact gtcgtcgtcc cctcaaactg    6600
gcagatgcac ggttacgatg cgcccatcta caccaacgtg acctatccca ttacggtcaa    6660
tccgccgttt gttcccacgg agaatccgac gggttgttac tcgctcacat ttaatgttga    6720
tgaaagctgg ctacaggaag gccagacgcg aattatttt gatggcgttc ctattggtta    6780
aaaaatgagc tgatttaaca aaaatttaat gcgaattta acaaaatatt aacgtttaca    6840
atttaaatat ttgcttatac aatcttcctg tttttgggc ttttctgatt atcaaccggg    6900
gtacatatga ttgacatgct agttttacga ttaccgttca tcgattctct tgtttgctcc    6960
agactctcag gcaatgacct gatagccttt gtagatctct caaaaatagc taccctctcc    7020
ggcattaatt tatcagctag aacggttgaa tatcatattg atggtgattt gactgtctcc    7080
ggcctttctc acccttttga atctttacct acacattact caggcattgc atttaaaata    7140
tatgagggtt ctaaaaattt ttatccttgc gttgaaataa aggcttctcc cgcaaaagta    7200
ttacagggtc ataatgtttt tggtacaacc gatttagctt tatgctctga ggctttattg    7260
cttaattttg ctaattcttt gccttgcctg tatgatttat tggatgtt                7308
```

```
<210> SEQ ID NO 2
<211> LENGTH: 21
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 2
ttcctctacc acctacatca c                                                21

<210> SEQ ID NO 3
<211> LENGTH: 21
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 3
taacattcct aacttctcat a                                                21

<210> SEQ ID NO 4
<211> LENGTH: 21
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (21)..(21)
```

```
<220> FEATURE:
<221> NAME/KEY: misc_feature
<222> LOCATION: (21)..(21)
<223> OTHER INFORMATION: RHODAMINE GREEN

<400> SEQUENCE: 4
gtgatgtagg tggtagagga a                                                   21

<210> SEQ ID NO 5
<211> LENGTH: 24
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (24)..(24)
<223> OTHER INFORMATION: CY3

<400> SEQUENCE: 5
gtgatgtagg tggtagagga attt                                                24

<210> SEQ ID NO 6
<211> LENGTH: 21
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: MISC_FEATURE
<222> LOCATION: (21)..(21)
<223> OTHER INFORMATION: CY5

<400> SEQUENCE: 6
gtgatgtagg tggtagagga a                                                   21

<210> SEQ ID NO 7
<211> LENGTH: 21
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: MISC_FEATURE
<222> LOCATION: (21)..(21)
<223> OTHER INFORMATION: ALEXA FLUOR 488

<400> SEQUENCE: 7
tatgagaagt taggaatgtt a                                                   21

<210> SEQ ID NO 8
<211> LENGTH: 21
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: MISC_FEATURE
<222> LOCATION: (21)..(21)
<223> OTHER INFORMATION: CY3

<400> SEQUENCE: 8
tatgagaagt taggaatgtt a                                                   21

<210> SEQ ID NO 9
<211> LENGTH: 21
<212> TYPE: DNA
<213> ORGANISM: Artificial Sequence
<220> FEATURE:
```

```
<223> OTHER INFORMATION: SYNTHETIC OLIGONUCLEOTIDE
<220> FEATURE:
<221> NAME/KEY: MISC_FEATURE
<222> LOCATION: (21)..(21)
<223> OTHER INFORMATION: CY5

<400> SEQUENCE: 9
tatgagaagt taggaatgtt a                                             21

<210> SEQ ID NO 10
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 10
gaatcggtca cagtacaacc gcgccgtagg gctgatcaaa gc                      42

<210> SEQ ID NO 11
<211> LENGTH: 21
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: MISC_FEATURE
<222> LOCATION: (1)..(1)
<223> OTHER INFORMATION: BIOTIN

<400> SEQUENCE: 11
gctttgatca gccctacggc g                                             21

<210> SEQ ID NO 12
<211> LENGTH: 21
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 12
cggttgtact gtgaccgatt c                                             21

<210> SEQ ID NO 13
<211> LENGTH: 32
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 13
aggatccccg ggtaccggct agtacccgta ta                                 32

<210> SEQ ID NO 14
<211> LENGTH: 40
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 14 atatttagt taatttcatc ttctgaccta aatttaatgg                          40

<210> SEQ ID NO 15
<211> LENGTH: 40
<212> TYPE: DNA
<213> ORGANISM: Artificial Sequence
```

```
<220> FEATURE:
<223> OTHER INFORMATION: SYNTHETIC OLIGONUCLEOTIDE

<400> SEQUENCE: 15
tttgaaatac cgaccgtgtg ataaataagg cgttaaataa                    40

<210> SEQ ID NO 16
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 16
agtaataaaa gggactgttt cctgtgtgcc tttgatagcg agttcctcta ccacctacat    60
cac                                                           63

<210> SEQ ID NO 17
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 17
aaatggatta tttaaacata cgagccggac ggccagtgcc aattcctcta ccacctacat    60
cac                                                           63

<210> SEQ ID NO 18
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 18
aacgctcatg gaaataatga gtgagctatg ggtaacgcca gg                 42

<210> SEQ ID NO 19
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 19
aatatccaga acaacccgct ttccagtccg ccagctggcg aa                 42

<210> SEQ ID NO 20
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 20
acttgcctga gtagtgaatc ggccaacgaa ctgttgggaa gg                 42

<210> SEQ ID NO 21
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE
```

<400> SEQUENCE: 21
attaaccgtt gtagcgccag ggtggtttgc cggaaaccag gc        42

<210> SEQ ID NO 22
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 22
atcagtgagg ccacctgatt gcccttcagg aagatcgcac tc        42

<210> SEQ ID NO 23
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 23
agacaggaac ggtagcggtc cacgctggtg catctgccag tt        42

<210> SEQ ID NO 24
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 24
atcagagcgg gagcgatggt ggttccgaat gggataggtc ac        42

<210> SEQ ID NO 25
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 25
ggttgctttg acgagaatag cccgagatcc cgtcggattc tc        42

<210> SEQ ID NO 26
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 26 acaccgccg cgctaagagt ccactatttg tagccagctt tc        42

<210> SEQ ID NO 27
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 27
agggcgctgg caagcgaaaa accgtctacc aataggaacg cc        42

<210> SEQ ID NO 28
<211> LENGTH: 42

```
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 28
gtggcgagaa aggatcaccc aaatcaagaa aattcgcatt aa                              42

<210> SEQ ID NO 29
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 29
gggagccccc gattctaaat cggaaccctg tataagcaaa ta                              42

<210> SEQ ID NO 30
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 30
aagaactggc tcatcggaac aacattatta ccccggttga ta                              42

<210> SEQ ID NO 31
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 31
taatttcaac tttatttagg aataccacat cgatgaacgg ta                              42

<210> SEQ ID NO 32
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 32
gagaaacacc agaaaaagga attacgaggg ctatcaggtc at                              42

<210> SEQ ID NO 33
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 33
cgtaacaaag ctgcctcgtt taccagacat taatgccgga ga                              42

<210> SEQ ID NO 34
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 34
```

```
gagtaatctt gacattttgc aaaagaagca aatcaccatc aa                              42
```

<210> SEQ ID NO 35
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 35

```
cggtgtacag accatttaga ctggatagtg taggtaaaga tt                              42
```

<210> SEQ ID NO 36
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 36

```
taagggaacc gaacattcat tgaatccctt tagaaccctc at                              42
```

<210> SEQ ID NO 37
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 37

```
ctccatgtta cttacgagaa tgaccatatt ttgcgggaga ag                              42
```

<210> SEQ ID NO 38
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 38

```
ttgtatcatc gcctattata gtcagaagag ctaaatcggt tg                              42
```

<210> SEQ ID NO 39
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 39

```
cccagcgatt atacaggaag cccgaaagca aagaattagc aa                              42
```

<210> SEQ ID NO 40
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 40

```
cgaaagaggc aaaattcaaa gcgaaccaaa tagtagtagc at                              42
```

<210> SEQ ID NO 41
<211> LENGTH: 42
<212> TYPE: DNA
<213> ORGANISM: Artificial Sequence

<220> FEATURE:
<223> OTHER INFORMATION: SYNTHETIC OLIGONUCLEOTIDE

<400> SEQUENCE: 41
gggtaaaata cgtaattaga gagtaccttt catttggggc gc        42

<210> SEQ ID NO 42
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 42
ttgaggacta aagattttgc ggatggctag atacatttcg ca        42

<210> SEQ ID NO 43
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 43
aaagacagca tcggtagctc aacatgtttg attcccaatt ct        42

<210> SEQ ID NO 44
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 44
ttaccagcgc caaattagtt tgaccattta gagcttaatt gc        42

<210> SEQ ID NO 45
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 45
aataagttta tttttgttta gctatatttt aattgctcct tt        42

<210> SEQ ID NO 46
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 46
ataaaggtgg caacgcatca attctactga ccggaagcaa ac        42

<210> SEQ ID NO 47
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 47
tccttattac gcagtcatac aggcaaggac ttcaaatatc gc        42

<210> SEQ ID NO 48
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 48
caataataac ggaagcctca gagcataaca aagcggattg ca                          42

<210> SEQ ID NO 49
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 49
cagatagccg aacatgaccc tgtaatacaa tcaaaaatca gg                          42

<210> SEQ ID NO 50
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 50
agcaatagct atctcaagga taaaaattcc tcaaatgctt ta                          42

<210> SEQ ID NO 51
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 51
aattgagtta agccatgcct gagtaatgcg tccaatactg cg                          42

<210> SEQ ID NO 52
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 52
agagggtaat tgagaggccg gagacagttt ttgccagagg gg                          42

<210> SEQ ID NO 53
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 53
cgcattagac gggagttcta gctgataaga cgataaaaac ca                          42

<210> SEQ ID NO 54
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 54
aatagcagcc tttagagaga tctacaaagc atagtaagag ca                            42

<210> SEQ ID NO 55
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 55
atccaaataa gaaagagcaa acaagagaat tcaactaatg ca                            42

<210> SEQ ID NO 56
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 56
aatttgccag ttacatgtca atcatatgta caggtagaaa ga                            42

<210> SEQ ID NO 57
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 57
tcctgaatct taccaaaaac aggaagatta aaatctacgt ta                            42

<210> SEQ ID NO 58
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 58
aaatcaagat tagtgttaat attttgtttt ttttggggtc ga                            42

<210> SEQ ID NO 59
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 59
gttttagcga acctagctca ttttttaatc agggcgatgg cc                            42

<210> SEQ ID NO 60
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 60
tcagatatag aagggcgtct ggccttccaa agaacgtgga ct                            42

<210> SEQ ID NO 61

<210> SEQ ID NO 61
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 61
ttttcatcgt aggatgagcg agtaacaaag ggttgagtgt tg         42

<210> SEQ ID NO 62
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 62
aaccaagtac cgcagcggat tgaccgtaaa tcggcaaaat cc         42

<210> SEQ ID NO 63
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 63
ataatcggct gtctgcgcat cgtaaccgtt tgccccagca gg         42

<210> SEQ ID NO 64
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 64
ataatatccc atcccagtat cggcctcacc gcctggccct ga         42

<210> SEQ ID NO 65
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 65
cgcgcctgtt tatcgcaccg cttctggttt cttttcacca gt         42

<210> SEQ ID NO 66
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 66
tccagacgac gacacattca ggctgcgccg cggggagagg cg         42

<210> SEQ ID NO 67
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 67

```
ataagagaat ataacctctt cgctattagg gaaacctgtc gt                    42
```

<210> SEQ ID NO 68
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 68

```
acgccaacat gtaacaaggc gattaagtac tcacattaat tg                    42
```

<210> SEQ ID NO 69
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 69

```
cgctcaacag tagggacgtt gtaaaacgaa gcataaagtg ta                    42
```

<210> SEQ ID NO 70
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 70

```
gtatcatatg cgttaggtcg actctagaaa attgttatcc gcttcctcta ccacctacat    60
cac                                                                  63
```

<210> SEQ ID NO 71
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 71

```
gaataaacac cggagaccgt atacgcatga gctcgaattc gtttcctcta ccacctacat    60
cac                                                                  63
```

<210> SEQ ID NO 72
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 72

```
aaactttttc aaatcctgaa agcgtaagga gatagaaccc ttttcctcta ccacctacat    60
cac                                                                  63
```

<210> SEQ ID NO 73
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 73

```
aaatgctgat gcaatggcta ttagtcttcc agtcacacga ccttcctcta ccacctacat    60
cac                                                                  63

<210> SEQ ID NO 74
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 74 cttttttaacc tccgtcgcca ttaaaaatcg ctcaatcgtc tg                      42

<210> SEQ ID NO 75
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 75
gtcaatagtg aattacagag gtgaggcgat tgcaacagga aa                       42

<210> SEQ ID NO 76
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 76
cttgaaaaca tagcccacgc tgagagcctc ggccttgctg gt                       42

<210> SEQ ID NO 77
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 77
cttctgtaaa tcgtccttgc tgaacctctt agtaataaca tc                       42

<210> SEQ ID NO 78
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 78
ggaaacagta catatcagtt ggcaaatctg tccatcacgc aa                       42

<210> SEQ ID NO 79
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 79
ttaattacat ttaatctaaa atatctttga agtgttttta ta                       42

<210> SEQ ID NO 80
<211> LENGTH: 42
```

```
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 80
tgagcaaaag aagaccgtca atagataaat taaagggatt tt                           42

<210> SEQ ID NO 81
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 81
gttacaaaat cgcgtttaca aacaattcct ttcctcgtta ga                           42

<210> SEQ ID NO 82
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 82
ggagaaacaa taacacgtta ttaattttag ggcgcgtact at                           42

<210> SEQ ID NO 83
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 83
ttaacgtcag atgaggaaca aagaaacctg cgcgtaacca cc                           42

<210> SEQ ID NO 84
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 84
gcacgtaaaa cagatcctga ttatcagaaa ggagcgggcg ct                           42

<210> SEQ ID NO 85
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 85
tgaataatgg aaggttgttt ggattataga aagccggcga ac                           42

<210> SEQ ID NO 86
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 86
```
agtaacagtg cccggaaagt attaagagcg ttgggaagaa aa        42

<210> SEQ ID NO 87
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 87
aggagtgtac tggtattagc ggggttttcc ttatgcgatt tt        42

<210> SEQ ID NO 88
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 88
tttaccgttc cagtgagagg gttgatatgg cttgagatgg tt        42

<210> SEQ ID NO 89
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 89
taaatcctca ttaagtactc aggaggttag gcttgccctg ac        42

<210> SEQ ID NO 90
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 90
ttgaggcagg tcagctcaga accgccacat tacccaaatc aa        42

<210> SEQ ID NO 91
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 91
accagaacca ccacgatagc aagcccaact gaccttcatc aa        42

<210> SEQ ID NO 92
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 92
ctcagaaccg ccacttcgtc accagtacag aggacagatg aa        42

<210> SEQ ID NO 93
<211> LENGTH: 42
<212> TYPE: DNA
<213> ORGANISM: Artificial Sequence

```
<220> FEATURE:
<223> OTHER INFORMATION: SYNTHETIC OLIGONUCLEOTIDE

<400> SEQUENCE: 93
accagagcca ccacacagcc ctcatagtca gacggtcaat ca                    42

<210> SEQ ID NO 94
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 94
cttattagcg tttgtttcca gacgttagaa atccgcgacc tg                    42

<210> SEQ ID NO 95
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 95
agactgtagc gcgttaaaca actttcaaag tacaacggag at                    42

<210> SEQ ID NO 96
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 96
accgtaatca gtagaacaac taaaggaaac tcatctttga cc                    42

<210> SEQ ID NO 97
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 97
agcaaggccg gaaaaatctc caaaaaaagc accaacctaa aa                    42

<210> SEQ ID NO 98
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 98
ggaattagag ccagcggttt atcagcttag tttccattaa ac                    42

<210> SEQ ID NO 99
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 99
cattaaaggt gaattgatac cgatagttcg gctacagagg ct                    42
```

```
<210> SEQ ID NO 100
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 100
tgaatataat gctgaacgag ggtagcaagc gccgacaatg ac              42

<210> SEQ ID NO 101
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 101
tgataagagg tcatcttttt catgaggagc tttcgaggtg aa              42

<210> SEQ ID NO 102
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 102
tccaacaggt caggatgcca ctacgaagag gctccaaaag ga              42

<210> SEQ ID NO 103
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 103
gttttaattc gagcgaatac actaaaactt gcgaataata at              42

<210> SEQ ID NO 104
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 104
tcaaaaagat taagcaagcg cgaaacaaca gtttcagcgg ag              42

<210> SEQ ID NO 105
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 105
tctttaccct gactgataaa ttgtgtcgta aatgaattttt ct             42

<210> SEQ ID NO 106
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE
```

<400> SEQUENCE: 106
aacagttcag aaaagccgga acgaggcgta gcgtaacgat ct                              42

<210> SEQ ID NO 107
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 107
gaatcgtcat aaattgacca actttgaaaa actacaacgc ct                              42

<210> SEQ ID NO 108
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 108
gtaatagtaa aatgggcgca taggctggta ggaacccatg ta                              42

<210> SEQ ID NO 109
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 109
aaatagcgag aggcagaacc ggatattccc tcagagccac ca                              42

<210> SEQ ID NO 110
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 110
acactatcat aacctcattc agtgaatata gtaccgccac cc                              42

<210> SEQ ID NO 111
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 111
gatacataac gccacgagta gtaaattgaa gtatagcccg ga                              42

<210> SEQ ID NO 112
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 112
ttcatcagtt gagaatcatt gtgaattagc tcagtaccag gc                              42

<210> SEQ ID NO 113

-continued

<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 113
ataaaacgaa ctaatatacc agtcaggagc tgagactcct ca                          42

<210> SEQ ID NO 114
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 114
ggtgccgtaa agcatagagc ttgacgggct tttcggaacc ta                          42

<210> SEQ ID NO 115
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 115
cactacgtga accaagggaa gaaagcgatg atggcaattc at                          42

<210> SEQ ID NO 116
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 116
ccaacgtcaa agggtgtagc ggtcacgcac cagaaggagc gg                          42

<210> SEQ ID NO 117
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 117
ttccagtttg gaactaatgc gccgctacaa aagtttgagt aa                          42

<210> SEQ ID NO 118
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 118
cttataaatc aaaagcacgt ataacgtgga caactcgtat ta                          42

<210> SEQ ID NO 119
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 119
cgaaaatcct gttttaaaca ggaggccgta catttgagga tt                          42

<210> SEQ ID NO 120
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 120
gagagttgca gcaacgccag aatcctgaag gagcactaac aa                          42

<210> SEQ ID NO 121
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 121
gagacgggca acagcgagta aaagagtcaa cagttgaaag ga                          42

<210> SEQ ID NO 122
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 122
gtttgcgtat tgggcaatac ttctttgaaa atatcaaacc ct                          42

<210> SEQ ID NO 123
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 123
gccagctgca ttaaaagaac tcaaactaag cagcaaatga aa                          42

<210> SEQ ID NO 124
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 124
cgttgcgctc actgtattac cgccagccgt cagtattaac ac                          42

<210> SEQ ID NO 125
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 125
aagcctgggg tgcctaccta cattttgaac cgaacgaacc ac                          42

<210> SEQ ID NO 126
<211> LENGTH: 63
<212> TYPE: DNA

```
<213> ORGANISM: Artificial Sequence
<220> FEATURE:
<223> OTHER INFORMATION: SYNTHETIC OLIGONUCLEOTIDE

<400> SEQUENCE: 126
tcacaattcc acaccattgg cagattcata atgcgcgaac tgttcctcta ccacctacat    60
cac                                                                  63

<210> SEQ ID NO 127
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 127
aatcatggtc atagcattct ggccaacaaa tacgtggcac agttcctcta ccacctacat    60
cac                                                                  63

<210> SEQ ID NO 128
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 128
gcaagtccgc tagcatcata attactagca aagaacgcga gattcctcta ccacctacat    60
cac                                                                  63

<210> SEQ ID NO 129
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 129
gcttgcatgc ctgcatacaa attcttacat ataactatat gtttcctcta ccacctacat    60
cac                                                                  63

<210> SEQ ID NO 130
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 130
gttttcccag tcacgcttaa ttgagaatgt ctgagagact ac                       42

<210> SEQ ID NO 131
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 131 aggggggatgt gctgtttagg cagaggcaag acgctgagaa ga                      42

<210> SEQ ID NO 132
<211> LENGTH: 42
```

```
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 132
gcgatcggtg cgggagtacc gacaaaagtt tcccttagaa tc                    42

<210> SEQ ID NO 133
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 133
aaagcgccat tcgcataaac aacatgttag tgaataacct tg                    42

<210> SEQ ID NO 134
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 134
cagccagctt tccgaacaat agataagttt acctttttta at                    42

<210> SEQ ID NO 135
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 135
tgaggggacg acgataattt acgagcattc aagaaaacaa aa                    42

<210> SEQ ID NO 136
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 136
gttggtgtag atggttcctt atcattcctc atttcaatta cc                    42

<210> SEQ ID NO 137
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 137
cgtgggaaca aacgctcatc gagaacaagc tttgaatacc aa                    42

<210> SEQ ID NO 138
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 138
```
atcaacatta aatgatcatt accgcgccta ccttttacat cg                              42

<210> SEQ ID NO 139
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 139
atcaaaaata attccttatc cggtattcgt agattttcag gt                              42

<210> SEQ ID NO 140
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 140
atttttgtta aatccccgac ttgcgggata tcaaaattat tt                              42

<210> SEQ ID NO 141
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 141
tttaaattgt aaactgctat tttgcaccgc ccctgccta tc                               42

<210> SEQ ID NO 142
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 142
atcagaaaag ccccaacgct aacgagcggg gtcagtgcct tg                              42

<210> SEQ ID NO 143
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 143
atcgtaaaac tagcaaaata aacagccagc ttttgatgat ac                              42

<210> SEQ ID NO 144
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 144
tgcctgagag tctgcgattt tttgtttagc gcagtctctg aa                              42

<210> SEQ ID NO 145
<211> LENGTH: 42
<212> TYPE: DNA
<213> ORGANISM: Artificial Sequence

```
<220> FEATURE:
<223> OTHER INFORMATION: SYNTHETIC OLIGONUCLEOTIDE

<400> SEQUENCE: 145
gggtagctat ttttcagaga gaataacata ttcacaaaca aa          42

<210> SEQ ID NO 146
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 146
tatgatattc aaccgaatta actgaacagc attgacagga gg          42

<210> SEQ ID NO 147
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 147
caaaagggtg agaacgctaa tatcagagcc ctcagagccg cc          42

<210> SEQ ID NO 148
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 148
atattttaaa tgcacaataa taagagcatc agagccgcca cc          42

<210> SEQ ID NO 149
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 149
cctttatttc aacgtaccga agcccttttc aaaatcaccg ga          42

<210> SEQ ID NO 150
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 150
taccaaaaac attaaagtta ccagaaggtc ggtcatagcc cc          42

<210> SEQ ID NO 151
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 151
aattaagcaa taaatacccaa aagaactttt gcctttagcg tc          42
```

<210> SEQ ID NO 152
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 152
taacatccaa taaatatgtt agcaaacgcc atcgatagca gc         42

<210> SEQ ID NO 153
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 153
gagctgaaaa ggtgatataa aagaaacggc accattacca tt         42

<210> SEQ ID NO 154
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 154
aatggtcaat aaccgtcaca atcaatagac ttgagccatt tg         42

<210> SEQ ID NO 155
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 155
gcgaacgagt agatgacaaa agggcgactg acggaaatta tt         42

<210> SEQ ID NO 156
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 156
aacaaccatc gcccgggaag gtaaatatat tcaaccgatt ga         42

<210> SEQ ID NO 157
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 157
tttcttaaac agcttatcac cgtcaccgaa aattcatatg gt         42

<210> SEQ ID NO 158
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

```
<400> SEQUENCE: 158
gcctttaatt gtatcaaaat caccagtaca aagacaccac gg                           42

<210> SEQ ID NO 159
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 159
tttttcacgt tgaacgtcac caatgaaata gaaaatacat ac                           42

<210> SEQ ID NO 160
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 160
tgagaataga aaggcgacag aatcaagtgg catgattaag ac                           42

<210> SEQ ID NO 161
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 161
gtatgggatt ttgctttcat cggcatttaa accgaggaaa cg                           42

<210> SEQ ID NO 162
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 162
aaagttttgt cgtcccatct tttcataatt aagaaaagta ag                           42

<210> SEQ ID NO 163
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 163
gtagcattcc acagcggaac cgcctcccag aaacaatgaa at                           42

<210> SEQ ID NO 164
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 164
ccgtaacact gagtcctcag agccaccaag ataacccaca ag                           42

<210> SEQ ID NO 165
```

<210> SEQ ID NO 165
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 165
ccctcatttt caggcagagc cgccgccacc ctgaacaaag tc            42

<210> SEQ ID NO 166
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 166
tcagaaccgc caccacgatt ggccttgata aaaacaggga ag            42

<210> SEQ ID NO 167
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 167
ataggtgtat caccagccag aatggaaaac gtcaaaatg aa             42

<210> SEQ ID NO 168
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 168
ggataagtgc cgtcaagcgt catacatgta ttatttatcc ca            42

<210> SEQ ID NO 169
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 169
agagaaggat taggaataag ttttaacgtc tttccagagc ct            42

<210> SEQ ID NO 170
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 170
ttattctgaa acattataaa cagttaatca gctacaattt ta            42

<210> SEQ ID NO 171
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 171
caatataatc ctgagttaga acctaccagg ttttgaagcc tt       42

<210> SEQ ID NO 172
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 172
aattatcatc atataataaa gaaattgcta agaacgcgag gc       42

<210> SEQ ID NO 173
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 173
cattatcatt ttgcatatac agtaacagca atagcaagca aa       42

<210> SEQ ID NO 174
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 174
aatcctttgc ccgaggattc gcctgattgc aagccgtttt ta       42

<210> SEQ ID NO 175
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 175
tagaagtatt agaccagagg cgaattataa gaacgggtat ta       42

<210> SEQ ID NO 176
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 176
ctaatagatt agagtgatga acaaacagt agaaaccaat ca       42

<210> SEQ ID NO 177
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 177
attgaggaag gttacaattt catttgaacc tgaacaagaa aa       42

<210> SEQ ID NO 178
<211> LENGTH: 42
<212> TYPE: DNA

```
<213> ORGANISM: Artificial Sequence
<220> FEATURE:
<223> OTHER INFORMATION: SYNTHETIC OLIGONUCLEOTIDE

<400> SEQUENCE: 178
caatcaatat ctggaatcaa tatatgtgca gctaatgcag aa                        42

<210> SEQ ID NO 179
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 179
aatctaaagc atcacgctat taattaatgt aaagtaattc tg                        42

<210> SEQ ID NO 180
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 180
cgcctgcaac agtggatagc ttagattatt ttcgagccag ta                        42

<210> SEQ ID NO 181
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 181
cagcagaaga taaatatcaa aatcatagcg ccatatttaa ca                        42

<210> SEQ ID NO 182
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 182
atagccctaa aacagcttag gttgggttca gtataaagcc aattcctcta ccacctacat     60
cac                                                                   63

<210> SEQ ID NO 183
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 183
acaatatttt tgaaatccaa tcgcaagaaa aaagcctgtt tattcctcta ccacctacat     60
cac                                                                   63

<210> SEQ ID NO 184
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE
```

<400> SEQUENCE: 184
ggatgtaaat gctgttccat ataacagttt aaatatgcaa ct       42

<210> SEQ ID NO 185
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 185
ttatataact atgaacgcat aaccgataca ccctcagcag cg       42

<210> SEQ ID NO 186
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 186
aaagtacggt gtactttgc gggatcgtta ttcggtcgct ga        42

<210> SEQ ID NO 187
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 187
cgctggaagt ttcaatgcaa atccaatccg gcttaggttg gg       42

<210> SEQ ID NO 188
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 188
ggcttgcagg gacgaccttt ttaacctcgc aagacaaaga ac       42

<210> SEQ ID NO 189
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 189
gagttaaagg ccgcggccag tgccaagcac gacgttgtaa aa       42

<210> SEQ ID NO 190
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 190
ccattgcaac aggatttgat agcgaggctg caaggcgatt aa       42

<210> SEQ ID NO 191

```
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 191
tatcggcctt gctgctagta cccgtatagg cctcttcgct at                42

<210> SEQ ID NO 192
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 192
gattagtaat aacagtaatc atggtcatgc cattcaggct gc                42

<210> SEQ ID NO 193
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 193
tctgtccatc acgcgctcac aattccaccg gcaccgcttc tg                42

<210> SEQ ID NO 194
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 194
gagaagtgtt tttataaagc ctggggtgga cagtatcggc ct                42

<210> SEQ ID NO 195
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 195
cgattaaagg gatttgcgtt gcgctcacgg gcgcatcgta acttcctcta ccacctacat    60
cac                                                                  63

<210> SEQ ID NO 196
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 196
tgctttcctc gttagtgcca gctgcattcg gcggattgac cgttcctcta ccacctacat    60
cac                                                                  63

<210> SEQ ID NO 197
<211> LENGTH: 42
<212> TYPE: DNA
<213> ORGANISM: Artificial Sequence
```

<220> FEATURE:
<223> OTHER INFORMATION: SYNTHETIC OLIGONUCLEOTIDE

<400> SEQUENCE: 197
acagggcgcg tactcggttt gcgtattgtg tgagcgagta ac         42

<210> SEQ ID NO 198
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 198
gctgcgcgta accagtgaga cgggcaactc gcgtctggcc tt         42

<210> SEQ ID NO 199
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 199
gaaaggagcg ggcggagaga gttgcagctc agctcatttt tt         42

<210> SEQ ID NO 200
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 200
gggaaagccg gcgaggcgaa aatcctgtac gttaatattt tg         42

<210> SEQ ID NO 201
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 201
aaatcggaac cctacccctta taaatcaacc aaaaacagga ag         42

<210> SEQ ID NO 202
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 202
acccaaatca agtttgttcc agtttggagc atgtcaatca ta         42

<210> SEQ ID NO 203
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 203
aaaaaccgtc tatcctccaa cgtcaaagtg gagcaaacaa ga         42

<210> SEQ ID NO 204
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 204
taaggcttgc cctgacttta atcattgttt gagagatcta ca         42

<210> SEQ ID NO 205
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 205
tcattaccca aatcgctcat tataccagcc gttctagctg at         42

<210> SEQ ID NO 206
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 206
ggctgacctt catctaataa aacgaactaa aggccggaga ca         42

<210> SEQ ID NO 207
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 207
aaagaggaca gatggattca tcagttgaca atgcctgagt aa         42

<210> SEQ ID NO 208
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 208
cgcagacggt caatcagata cataacgccg caaggataaa aa         42

<210> SEQ ID NO 209
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 209
cgaaatccgc gacccaacac tatcataata tgaccctgta at         42

<210> SEQ ID NO 210
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 210
aaagtacaac ggagcaaaat agcgagagaa gcctcagagc at                42

<210> SEQ ID NO 211
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 211
acactcatct ttgagggtaa tagtaaaaaa tcatacaggc aa                42

<210> SEQ ID NO 212
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 212
aggcaccaac ctaacggaat cgtcataatg gcatcaattc ta                42

<210> SEQ ID NO 213
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 213
gaagtttcca ttaataaaca gttcagaacc tgtttagcta ta                42

<210> SEQ ID NO 214
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 214
aacggctaca gagggtctt taccctgaat ttagtttgac ca                 42

<210> SEQ ID NO 215
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 215
gtcaccctca gcagcatcaa aaagattaca ttccatataa ca                42

<210> SEQ ID NO 216
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 216
cgctgaggct tgcagcgttt taattcgaca tgttttaaat attaacattc ctaacttctc    60
ata                                                                 63

<210> SEQ ID NO 217
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 217
aatgacaaca accaactcca acaggtcaat ggcttagagc tttaacattc ctaacttctc    60
ata                                                                 63

<210> SEQ ID NO 218
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 218
cgtagaaaat acatatgctg tagctcaagc ttcaaagcga actaacattc ctaacttctc    60
ata                                                                 63

<210> SEQ ID NO 219
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 219
ctggcatgat taaggtgtct ggaagtttag aggaagcccg aataacattc ctaacttctc    60
ata                                                                 63

<210> SEQ ID NO 220
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 220
ggaaaccgag gaaactgcga acgagtagct attatagtca ga                      42

<210> SEQ ID NO 221
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 221
ttttaagaaa agtacaaatg gtcaataaaa cgagaatgac ca                      42

<210> SEQ ID NO 222
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 222
caagaaacaa tgaagcgagc tgaaaaggat attcattgaa tc                      42

```
<210> SEQ ID NO 223
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 223
agagataacc cacaattaac atccaatatg tttagactgg at                    42

<210> SEQ ID NO 224
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 224
caccctgaac aaagaaaatt aagcaatagc ttttgcaaaa ga                    42

<210> SEQ ID NO 225
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 225
cataaaaaca gggatgtacc aaaaacatcc ctcgtttacc ag                    42

<210> SEQ ID NO 226
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 226
taacgtcaaa aatgagcctt tatttcaaca aaaggaatta cg                    42

<210> SEQ ID NO 227
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 227
catattattt atccatatat tttaaatgga tttaggaata cc                    42

<210> SEQ ID NO 228
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 228
cgtctttcca gagcttcaaa agggtgagaa cggaacaaca tt                    42

<210> SEQ ID NO 229
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE
```

<400> SEQUENCE: 229
cccagctaca atttaatatg atattcaatc aggacgttgg ga         42

<210> SEQ ID NO 230
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 230
gaggttttga agccgagggt agctatttga attaccttat gc         42

<210> SEQ ID NO 231
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 231
tctaagaacg cgagattgcc tgagagtcgg attgggcttg ag         42

<210> SEQ ID NO 232
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 232
cccaatagca agcataatcg taaaactaac aagagtccac ta         42

<210> SEQ ID NO 233
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 233
aagcaagccg tttttaatca gaaaagccaa gaatagcccg ag         42

<210> SEQ ID NO 234
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 234
ccaagaacgg gtattattta aattgtaatt gatggtggtt cc         42

<210> SEQ ID NO 235
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 235
atgtagaaac caataaattt ttgttaaaaa gcggtccacg ct         42

<210> SEQ ID NO 236
<211> LENGTH: 42

```
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 236
gtcctgaaca agaaccatca aaataatag ctgattgccc tt                        42

<210> SEQ ID NO 237
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 237
ttcagctaat gcagtcatca acattaaagg cgccagggtg gt                       42

<210> SEQ ID NO 238
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 238
aggtaaagta attctccgtg ggaacaaaaa tgaatcggcc aa                       42

<210> SEQ ID NO 239
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 239
cattttcgag ccagacgttg gtgtagattg cccgctttcc agttcctcta ccacctacat    60
cac                                                                  63

<210> SEQ ID NO 240
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 240
atcgccatat ttaatttgag gggacgaccc taatgagtga gcttcctcta ccacctacat    60
cac                                                                  63

<210> SEQ ID NO 241
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 241
accagtataa agcctccagc cagctttcac aacatacgag cc                       42

<210> SEQ ID NO 242
<211> LENGTH: 42
<212> TYPE: DNA
<213> ORGANISM: Artificial Sequence
<220> FEATURE:
```

<223> OTHER INFORMATION: SYNTHETIC OLIGONUCLEOTIDE

<400> SEQUENCE: 242
agaaaaagcc tgttgcaaag cgccattcag ctgtttcctg tg         42

<210> SEQ ID NO 243
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 243
ataaggcgtt aaatgggcga tcggtgcgag gatccccggg ta         42

<210> SEQ ID NO 244
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 244
ctgacctaaa tttaaaaggg ggatgtgcaa gtccgctagc ga         42

<210> SEQ ID NO 245
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 245
gcgagaaaac ttttgggttt tcccagtctt gcatgcctgc ag         42

<210> SEQ ID NO 246
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 246
aggtctgaga gactctcaat cgtctgaaaa tacctacatt tt         42

<210> SEQ ID NO 247
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 247
taagacgctg agaaagtcac acgaccagaa tattaccgcc ag         42

<210> SEQ ID NO 248
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 248
attttccctt agaagataga acccttctag aagaactcaa ac         42

```
<210> SEQ ID NO 249
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 249
tgagtgaata acctagacaa tatttttgag caatacttct tt                        42

<210> SEQ ID NO 250
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 250
aattaccttt tttatgatag ccctaaaaac cgagtaaaag ag                        42

<210> SEQ ID NO 251
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 251
catcaagaaa acaaaccagc agaagatata cgccagaatc ctttcctcta ccacctacat    60
cac                                                                  63

<210> SEQ ID NO 252
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 252
attcatttca attaaccgcc tgcaacaggc taaacaggag gcttcctcta ccacctacat    60
cac                                                                  63

<210> SEQ ID NO 253
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 253
ttgctttgaa taccaaaatc taaagcatga gcacgtataa cg                        42

<210> SEQ ID NO 254
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 254
agtacctttt acatctcaat caatatctct taatgcgccg ct                        42

<210> SEQ ID NO 255
<211> LENGTH: 42
<212> TYPE: DNA
```

<213> ORGANISM: Artificial Sequence
<220> FEATURE:
<223> OTHER INFORMATION: SYNTHETIC OLIGONUCLEOTIDE

<400> SEQUENCE: 255
gcgtagattt tcaggaattg aggaaggtag tgtagcggtc ac                42

<210> SEQ ID NO 256
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 256
catatcaaaa ttataactaa tagattagga agggaagaaa gc                42

<210> SEQ ID NO 257
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 257
gtttggatta tacttttaga agtattagtt tagagcttga cg                42

<210> SEQ ID NO 258
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 258
ctgattatca gatgtaaatc ctttgccctg ccgtaaagca ct                42

<210> SEQ ID NO 259
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 259
aacaaagaaa ccacaacatt atcattttct acgtgaacca tc                42

<210> SEQ ID NO 260
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 260
aagcgcagtc tctgactggt aataagttaa cgagtagtaa cg                42

<210> SEQ ID NO 261
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 261
gatattcaca aacatgcccg tataaacagc tcattcagtg aa                42

<210> SEQ ID NO 262
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 262
cagcattgac aggatattat tctgaaacca agaaccggat at       42

<210> SEQ ID NO 263
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 263
caccctcaga gccgcaagag aaggattaca ggcgcatagg ct       42

<210> SEQ ID NO 264
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 264
cctcagagcc gccagcggat aagtgccgac tgaccaactt tg       42

<210> SEQ ID NO 265
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 265
aatcaaaatc accggaatag gtgtatcata gccggaacga gg       42

<210> SEQ ID NO 266
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 266
tttcggtcat agcccctcag aaccgccact gataaattgt gt       42

<210> SEQ ID NO 267
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 267
gtttgccttt agcgcaccct cattttcaac caagcgcgaa ac       42

<210> SEQ ID NO 268
<211> LENGTH: 42
<212> TYPE: DNA
<213> ORGANISM: Artificial Sequence
<220> FEATURE:

<223> OTHER INFORMATION: SYNTHETIC OLIGONUCLEOTIDE

<400> SEQUENCE: 268
aaccatcgat agcataccgt aacactgaaa gaatacacta aa        42

<210> SEQ ID NO 269
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 269
tagcaccatt accactgtag cattccacta atgccactac ga        42

<210> SEQ ID NO 270
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 270
cgacttgagc cattctaaag ttttgtcgga cttttcatg ag        42

<210> SEQ ID NO 271
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 271
attgacggaa attactgtat gggattttgg aacgagggta gc        42

<210> SEQ ID NO 272
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 272
caaaagggcg acatagtgag aatagaaagc ttttgcggga tctaacattc ctaacttctc        60
ata        63

<210> SEQ ID NO 273
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 273
cacaatcaat agaaattttt tcacgttgcc gatatattcg gttaacattc ctaacttctc        60
ata        63

<210> SEQ ID NO 274
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 274

```
cagaccggaa gcaatcgccc acgcataaaa aatctccaaa aataacattc ctaacttctc    60
ata                                                                 63

<210> SEQ ID NO 275
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 275
agacttcaaa tatcgggagt taaaggccgg aacaactaaa ggtaacattc ctaacttctc    60
ata                                                                 63

<210> SEQ ID NO 276
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 276
agcaaagcgg attgcgaaag acagcatcgc taaacaactt tc                      42

<210> SEQ ID NO 277
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 277
taaatcaaaa atcactttga ggactaaatc tttccagacg tt                      42

<210> SEQ ID NO 278
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 278
cccctcaaat gcttacgggt aaaatacgag acagccctca ta                      42

<210> SEQ ID NO 279
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 279
agcgtccaat actgaacgaa agaggcaagt ttcgtcacca gt                      42

<210> SEQ ID NO 280
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 280
agttttgcca gaggccccca gcgattatgg gatagcaagc cc                      42
```

<210> SEQ ID NO 281
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 281
acgacgataa aaacatttgt atcatcgccc ctcagaaccg cc         42

<210> SEQ ID NO 282
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 282
aggcatagta agagtgctcc atgttactcc gtactcagga gg         42

<210> SEQ ID NO 283
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 283
acattcaact aatgcataag ggaaccgatc gagagggttg at         42

<210> SEQ ID NO 284
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 284
attacaggta gaaaaacggt gtacagacgg attagcgggg tt         42

<210> SEQ ID NO 285
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 285
agaaaaatct acgtaagagt aatcttgaat gaaagtatta ag         42

<210> SEQ ID NO 286
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 286
gattttaaga actgaacgta acaaagctgt taatgccccc tg         42

<210> SEQ ID NO 287
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 287
atggtttaat ttcaacgaga aacaccagtt aacggggtca gt                              42

<210> SEQ ID NO 288
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 288
ttaaagaacg tggaagggcg atggcccagc catggctttt ga                              42

<210> SEQ ID NO 289
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 289
atagggttga gtgtttttgg ggtcgaggga acgttattaa tt                              42

<210> SEQ ID NO 290
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 290
gaaatcggca aataaggga gcccccgaac tttacaaaca at                               42

<210> SEQ ID NO 291
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 291
ggtttgcccc agcaacgtgg cgagaaagag ccgtcaatag at                              42

<210> SEQ ID NO 292
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 292
caccgcctgg ccctctaggg cgctggcata tctaaaatat ct                              42

<210> SEQ ID NO 293
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 293
ttttcttttc accaccacac ccgccgcggg tcagttggca aa                              42

<210> SEQ ID NO 294

```
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 294
cgcgcgggga gaggatggtt gctttgacca ccttgctgaa cc                    42

<210> SEQ ID NO 295
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 295
tcgggaaacc tgtcgaatca gagcgggatg ccacgctgag agttcctcta ccacctacat    60
cac                                                                  63

<210> SEQ ID NO 296
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 296
taactcacat taatttagac aggaacggaa acagaggtga ggttcctcta ccacctacat    60
cac                                                                  63

<210> SEQ ID NO 297
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 297
ggaagcataa agtgtaatca gtgaggccca tcgccattaa aa                    42

<210> SEQ ID NO 298
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 298
tgaaattgtt atccaaatta accgttgtaa tggctattag tc                    42

<210> SEQ ID NO 299
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 299
ccgagctcga attctcactt gcctgagtga cctgaaagcg ta                    42

<210> SEQ ID NO 300
<211> LENGTH: 42
<212> TYPE: DNA
<213> ORGANISM: Artificial Sequence
```

```
<220> FEATURE:
<223> OTHER INFORMATION: SYNTHETIC OLIGONUCLEOTIDE

<400> SEQUENCE: 300
ccgtatacgc atgggtaata tccagaacta ataaaaggga ca                              42

<210> SEQ ID NO 301
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 301
gtcgactcta gaccaaaacg ctcatggaat ggattattta ca                              42

<210> SEQ ID NO 302
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 302
gttgggtaac gccatcaaat atatttatt tatcaaaatc at                               42

<210> SEQ ID NO 303
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 303
tacgccagct ggcgatggtt tgaaatacgc gatagcttag at                              42

<210> SEQ ID NO 304
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 304
gcaactgttg ggaaaagaat aaacaccggt cgctattaat ta                              42

<210> SEQ ID NO 305
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 305
gtgccggaaa ccagtagtat catatgcgta aatcaatata tg                              42

<210> SEQ ID NO 306
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 306
caggaagatc gcacaacgct caacagtaaa caatttcatt tg                              42
```

<210> SEQ ID NO 307
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 307
cgtgcatctg ccagcaacgc caacatgtga tgatgaaaca aattcctcta ccacctacat    60
cac                                                                 63

<210> SEQ ID NO 308
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 308
taatgggata ggtctaataa gagaatatcg cagaggcgaa ttttcctcta ccacctacat    60
cac                                                                 63

<210> SEQ ID NO 309
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 309
aacccgtcgg attctgtcca gacgacgaac ggattcgcct ga                      42

<210> SEQ ID NO 310
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 310
cctgtagcca gcttaacgcg cctgtttaga atatacagta ac                      42

<210> SEQ ID NO 311
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 311
aaccaatagg aacgaaataa tatcccatga aataaagaaa tt                      42

<210> SEQ ID NO 312
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 312
ttaaaattcg cattcaataa tcggctgtgg gttagaacct ac                      42

<210> SEQ ID NO 313
<211> LENGTH: 42

```
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 313
attgtataag caaataaacc aagtaccgat ataatcctga tt                    42

<210> SEQ ID NO 314
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 314
tgtaccccgg ttgatatttt catcgtagtt atcatcatat tc                    42

<210> SEQ ID NO 315
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 315
gaatcgatga acggaatcag atatagaagt aagcgtcata gg                    42

<210> SEQ ID NO 316
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 316
aaggctatca ggtcgcgttt tagcgaacaa agccagaatg ga                    42

<210> SEQ ID NO 317
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 317
aaattaatgc cggattaaat caagattaag acgattggcc tt                    42

<210> SEQ ID NO 318
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 318
gtcaaatcac catctatcct gaatcttaac cagagccgcc gc                    42

<210> SEQ ID NO 319
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 319
```
tgtgtaggta aagactaatt tgccagttac cctcagagcc ac					42

<210> SEQ ID NO 320
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 320
tttttagaac cctccaatcc aaataagaac cggaaccgcc tc					42

<210> SEQ ID NO 321
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 321
acttttgcgg gagaaaaata gcagcctttg ccatcttttc at					42

<210> SEQ ID NO 322
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 322
aaagctaaat cggtagcgca ttagacgggt tttcatcggc at					42

<210> SEQ ID NO 323
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 323
ggcaaagaat tagctcagag ggtaattgag cgacagaatc aa					42

<210> SEQ ID NO 324
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 324
ctaatagtag tagcagaatt gagttaagaa cgtcaccaat ga					42

<210> SEQ ID NO 325
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 325
ttttcatttg gggcatagca atagctatag caaaatcacc ag					42

<210> SEQ ID NO 326
<211> LENGTH: 42
<212> TYPE: DNA
<213> ORGANISM: Artificial Sequence -continued

<220> FEATURE:
<223> OTHER INFORMATION: SYNTHETIC OLIGONUCLEOTIDE

<400> SEQUENCE: 326
ttagatacat tcgagcaga tagccgaaat tatcaccgtc ac                    42

<210> SEQ ID NO 327
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 327
gttgattccc aattcgcaat aataacggga gggaaggtaa at                   42

<210> SEQ ID NO 328
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 328
gcaactaaag tacgactcct tattacgcac cagcgccaaa gataacattc ctaacttctc    60
ata                                                                   63

<210> SEQ ID NO 329
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 329
aattgctgaa tataacataa aggtggcata agtttatttt gttaacattc ctaacttctc    60
ata                                                                   63

<210> SEQ ID NO 330
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 330
aaaggctcca aagaagaca ccacggaaac atataaaaga aataacattc ctaacttctc     60
ata                                                                   63

<210> SEQ ID NO 331
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 331
aattgcgaat aataaattca tatggtttag tatgttagca aataacattc ctaacttctc    60
ata                                                                   63

<210> SEQ ID NO 332
<211> LENGTH: 42
<212> TYPE: DNA

-continued

```
<213> ORGANISM: Artificial Sequence
<220> FEATURE:
<223> OTHER INFORMATION: SYNTHETIC OLIGONUCLEOTIDE

<400> SEQUENCE: 332
aacagtttca gcggtcaacc gattgaggaa tacccaaaag aa                              42

<210> SEQ ID NO 333
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 333
agtaaatgaa ttttttcatt aaaggtgaca aagttaccag aa                              42

<210> SEQ ID NO 334
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 334
gttagcgtaa cgattgggaa ttagagccct taccgaagcc ct                              42

<210> SEQ ID NO 335
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 335
acaaactaca acgcttagca aggccggacc caataataag ag                              42

<210> SEQ ID NO 336
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 336
aataggaacc catggcaccg taatcagtag cgctaatatc ag                              42

<210> SEQ ID NO 337
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 337
accctcagag ccactcagac tgtagcgcga gaattaactg aa                              42

<210> SEQ ID NO 338
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 338
tttagtaccg ccacccctta ttagcgttta cagagagaat aa                              42
```

<210> SEQ ID NO 339
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 339
ataagtatag cccggaacca gagccaccaa cgattttttg tt                42

<210> SEQ ID NO 340
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 340
ttgctcagta ccagccctca gaaccgccac aaaataaaca gc                42

<210> SEQ ID NO 341
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 341
aggctgagac tcctccacca gaaccacccc aacgctaacg ag                42

<210> SEQ ID NO 342
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 342
cctatttcgg aaccggttga ggcaggtcgt tgctattttg ca                42

<210> SEQ ID NO 343
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 343
gccttgagta acagaataaa tcctcattct cccgacttgc gg                42

<210> SEQ ID NO 344
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 344
tgatacagga gtgtaattta ccgttccagg cttatccggt at                42

<210> SEQ ID NO 345
<211> LENGTH: 42
<212> TYPE: DNA
<213> ORGANISM: Artificial Sequence
<220> FEATURE:

```
<223> OTHER INFORMATION: SYNTHETIC OLIGONUCLEOTIDE

<400> SEQUENCE: 345
ttaaaagttt gagtcagaag gagcggaaga atcattaccg cg                              42

<210> SEQ ID NO 346
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 346
tcgacaactc gtatatggca attcatcaca ctcatcgaga ac                              42

<210> SEQ ID NO 347
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 347
aatacatttg aggatctgaa taatggaact ttccttatca tt                              42

<210> SEQ ID NO 348
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 348
ttaggagcac taacttgcac gtaaaacacc taatttacga gc                              42

<210> SEQ ID NO 349
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 349
tcaacagttg aaaggtttaa cgtcagattc aacaatagat aa                              42

<210> SEQ ID NO 350
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 350
tcaaatatca aacccgggag aaacaataca ataaacaaca tg                              42

<210> SEQ ID NO 351
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 351
ccagcagcaa atgaaagtta caaaatcgaa agtaccgaca aattcctcta ccacctacat          60
cac                                                                        63
```

<210> SEQ ID NO 352
<211> LENGTH: 63
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 352
cggtcagtat taaccctgag caaaagaaaa tttaggcaga ggttcctcta ccacctacat    60
cac    63

<210> SEQ ID NO 353
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 353
ataccgaacg aaccaattaa ttacatttgg gcttaattga ga    42

<210> SEQ ID NO 354
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 354
tttaatgcgc gaacatggaa acagtacatt atacaaattc tt    42

<210> SEQ ID NO 355
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 355
agaatacgtg gcactgcttc tgtaaatcga atcataatta ct    42

<210> SEQ ID NO 356
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 356
ttctggccaa cagatccttg aaaacatacg accgtgtgat aa    42

<210> SEQ ID NO 357
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 357
ttggcagatt caccgagtca atagtgaagt taatttcatc tt    42

<210> SEQ ID NO 358
<211> LENGTH: 26
<212> TYPE: DNA

```
<213> ORGANISM: Artificial Sequence
<220> FEATURE:
<223> OTHER INFORMATION: SYNTHETIC OLIGONUCLEOTIDE

<400> SEQUENCE: 358
cttttgataa gaggtcattt ttgcgg                                        26

<210> SEQ ID NO 359
<211> LENGTH: 26
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 359
ggattagaga gtacctttaa ttgctc                                        26

<210> SEQ ID NO 360
<211> LENGTH: 40
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 360
tgaatttctt aaacagcttg ataccgatag ttgcgccgac                         40

<210> SEQ ID NO 361
<211> LENGTH: 40
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 361
gagcctttaa ttgtatcggt ttatcagctt gctttcgagg                         40
```

NUCLEIC ACID NANOSTRUCTURE BARCODE PROBES

RELATED APPLICATIONS

This application is a divisional of U.S. application Ser. No. 13/882,223, filed Jun. 11, 2013, which is a national stage filing under 35 U.S.C. § 371 of International Application No. PCT/US2011/058458, filed Oct. 28, 2011, which was published under PCT Article 21(2) in English and claims the benefit of U.S. Provisional Application Ser. No. 61/408,358, filed on Oct. 29, 2010, the entire contents of each of which are incorporated by reference herein.

GOVERNMENT SUPPORT

This invention was made with U.S. Government support under grant numbers OD004641, HG005592 and OD007292 awarded by the National Institutes of Health, CCF-1054898 awarded by the National Science Foundation, and N00014-10-1-0827 and N00014-11-1-0914 awarded by the Office of Naval Research. The Government has certain rights in the invention.

REFERENCE TO A COMPACT DISK APPENDIX

A computer program listing is appended to this disclosure and is hereby incorporated herein by this reference. The appendix includes the file programlisting.txt which includes listings for 6ht-v5-1color-1.json and 6ht-v6-2color-1.json.

BACKGROUND OF INVENTION

A major challenge in modern biology and nanotechnology is to observe, identify and differentiate a large number of different molecular species in real time. Fluorescent microscopy is a powerful tool for non-destructively and dynamically monitoring many individual molecular events. However, the multiplexing ability of fluorescent imaging is limited by the number of spectrally non-overlapping fluorophores available. There is therefore a great need for novel addressable fluorescent probes useful in multiplex detection systems.

BRIEF SUMMARY OF INVENTION

The invention provides, inter alia, nucleic acid barcode probes that comprise a nucleic acid nanostructure comprising one or more fluorescently labeled regions that may be stably or transiently bound (and thus labeled) with fluorophore-bearing oligonucleotides. The barcode probes may further comprise a target binding moiety. The invention also provides methods of use for such barcode probes including but not limited to their use in analyte detection assays (e.g., assays for detecting and optionally quantitating one or more analytes). The nature of the fluorescent signals (e.g., the wavelength or "color", intensity, etc.) and the pattern (or orientation, or arrangement or geometry) of such signals on the barcode can also be used to identify particular analytes in a sample. This facilitates multiplexed assays in which a plurality of analytes are detected simultaneously (or at a minimum with a single sample or a single aliquot from a sample).

In one aspect, the invention provides a method of detecting a target comprising: contacting a sample with a nucleic acid barcode probe, and determining whether the nucleic acid barcode probe binds to one or more components in the sample, wherein binding of the nucleic acid barcode probe to one or more components of the sample indicates presence of a target in the sample, and wherein the nucleic acid barcode probe comprises a nucleic acid nanostructure comprising a target binding moiety and at least two fluorescently labeled regions.

In some embodiments, the method further comprises identifying the target based on the color and/or orientation of the fluorescently labeled regions of the nucleic acid barcode probe bound to one or more components of the sample.

In some embodiments, whether the nucleic acid barcode probe binds to one or more components in the sample comprises contacting the nucleic acid barcode probe with soluble, transiently binding fluorophore-bearing oligonucleotides.

In some embodiments, the nucleic acid barcode probe comprises stably bound fluorophore-bearing oligonucleotides.

In another aspect, the invention provides a method of detecting a target comprising contacting the target with a nucleic acid barcode probe, under conditions sufficient for the target to bind to the nucleic acid barcode probe; separating the target from material that is not bound to the target; and detecting the presence of the nucleic acid barcode probe bound to the target, wherein the nucleic acid barcode probe comprises a nucleic acid nanostructure comprising a target binding moiety and at least two fluorescently labeled regions.

In some embodiments, the method further comprises identifying the target based on the color and/or orientation of the fluorescently labeled regions of the nucleic acid barcode probe bound to the target.

In some embodiments, detecting the presence of the nucleic acid barcode probe bound to the target comprises contacting the nucleic acid barcode probe with soluble, transiently bound fluorophore-bearing oligonucleotides.

In some embodiments, the nucleic acid barcode probe comprises stably bound fluorophore-bearing oligonucleotides.

In another aspect, the invention provides a nucleic acid barcode probe comprising a nucleic acid nanostructure, such as a DNA barcode probe comprising a DNA nanostructure, having at least two fluorescently-labeled regions. In some embodiments, the nanostructure comprises at least three fluorescently-labeled regions, and the orientation is determinable due to asymmetric spacing of the fluorescently-labeled regions. The locations of each of the fluorescently-labeled regions on the nanostructure are such that a pattern of the fluorescent labels is determinable based on the emission of visible light by the fluorescently-labeled regions. In some embodiments, the orientation of the barcode probe is determinable based on the emission of visible light by the fluorescently-labeled regions.

In some embodiments, each of the fluorescently-labeled regions has a center that is located at least 200 nm from the centers of the other fluorescently-labeled regions. In some embodiments, each of the fluorescently-labeled regions has a center that is located at least 250 nm from the centers of the other fluorescently-labeled regions. In some embodiments, each of the fluorescently-labeled regions has a center that is located at least about 25 nm, at least about 50 nm, or at least about 75 nm, or at least about 100 nm, or at least 150 nm from the centers of the other fluorescently-labeled regions.

In some embodiments, the nanostructure comprises a scaffold strand and plurality of staple strands. In some embodiments, the scaffold strand has a sequence derived from M13 bacteriophage. In some embodiments, the fluorescently-labeled regions of the DNA nanostructure comprise fluorophore-labeled staple strands. In some embodiments, the fluorophore-labeled staple strand is a transiently binding fluorophore-labeled staple strand. In some embodiments, the fluorophore-labeled staple strand is transiently binding at room temperature. In some embodiments, the fluorophore-labeled staple strand is 7-12 nucleotides in length. In some embodiments, the fluorophore-labeled staple strand is about 9 nucleotides in length. In some embodiments, the fluorophore-labeled staple strand is a stably binding fluorophore-labeled staple strand. In some embodiments, the fluorophore-labeled staple strand is a stably binding fluorophore-labeled staple strand at room temperature. In some embodiments, the fluorophore-labeled staple strand is at least 18 nucleotides in length, including in some embodiments 18-25 nucleotides in length.

In some embodiments, the fluorophore-labeled staple strands are directly labeled. In some embodiments, the fluorophore-labeled staple strands are indirectly labeled.

In some embodiments, the fluorophore-labeled staple strands have a staple domain hybridized to a scaffold strand and a handle domain hybridized to a fluorophore-labeled oligonucleotide. In some embodiments, the handle domain is 7-12 nucleotides in length. In some embodiments, the handle domain is about 9 nucleotides in length. In some embodiments, the handle domain is at least 18 nucleotides in length. In some embodiments, the handle domain is 18-25 nucleotides in length.

In some embodiments, the nanostructure is a nanotube. In some embodiments, the nanostructure is prepared using a DNA origami method. In some embodiments, the nanostructure comprises a single-stranded DNA tile. In some embodiments, the nanostructure comprises DNA hairpins.

In some embodiments, the barcode probe further comprises a target binding moiety. In some embodiments, the target binding moiety is a single-stranded nucleic acid complementary to a nucleic acid target. In some embodiments, the target binding moiety is an antibody. In some embodiments, the target binding moiety is a protein or peptide.

In some embodiments, wherein the nanostructure, once assembled, is sufficiently immutable in a resting state that the pattern of the fluorescent regions can be detected using light microscopy in that resting state. In some embodiments, the resting state comprises absence of an applied electric field.

In another aspect, the invention provides a composition comprising a plurality of any of the foregoing nucleic acid nanostructure barcode probes. In some embodiments, some or all members of the plurality are different from other members in the plurality. The members may differ from each other based on the target binding moiety and the signal and orientation (arrangements) of the barcode. In some embodiments, the plurality is equal to or less than 2, 3, 4, 5, 6, 7, 8, 9, 10, 11, 12, 13, 14, 15, 16, 17, 18, 19, 20, 25, 30, 40, 50, 100, 200 or more. In some instances, the plurality is equal to or less than 216.

In another aspect, the invention provides a method of identifying a target nucleic acid comprising contacting the target nucleic acid with any of the foregoing barcode probes under conditions such that the target nucleic acid binds to the barcode probe; separating the target nucleic acid from material that is not bound to the target nucleic acid; and detecting the presence of the barcode probe bound to the target nucleic acid.

In another aspect, the invention provides a method of identifying a target protein or cell comprising contacting the target protein or cell with any of the foregoing barcode probes under conditions such that the target protein or cell binds to the barcode probe; separating the target protein or cell from material that is not bound to the target protein or cell; and detecting the presence of the barcode probe bound to the target protein or cell.

In another aspect, the invention provides a method of identifying a target protein or cell comprising contacting the target protein or cell with any of the foregoing barcode probes under conditions such that the target protein or cell binds to the barcode probe; separating the target protein or cell from material that is not bound to the target protein or cell; and detecting the presence of the barcode probe bound to the target protein or cell.

In another aspect, the invention provides a method of detecting a target comprising contacting a sample with any of the foregoing nucleic acid barcode probes, and determining whether the nucleic acid barcode probe binds to one or more components in the sample, wherein binding of the nucleic acid barcode probe to one or more components in the sample indicates presence of a target in the sample.

In some embodiments, the method further comprises removing components in the sample that are not bound to the nucleic acid barcode probe following the contacting step.

In some embodiments, the target is a nucleic acid, a protein, a peptide, or a cell, or a combination thereof.

In some embodiments, the presence of the barcode probe is detected by fluorescent microscopy.

In some embodiments, the presence of the barcode probe is detected without exposing the DNA barcode probe to an electric field.

In some embodiments, each probe comprises a nucleic acid nanostructure having at least two fluorescently-labeled regions and a target binding moiety, wherein the locations of each of the fluorescently-labeled regions on the nanostructure are such that a pattern of the fluorescent labels of the barcode probe and the identity of the target binding moiety is determinable based on the emission of visible light by the fluorescently-labeled regions; and each of the fluorescently-labeled regions has a center that is located at least 200 nm from the centers of the other fluorescently-labeled regions.

In another aspect, the invention provides a population of nucleic acid barcode probes such as DNA barcode probes, wherein each probe comprises a nucleic acid nanostructure such as a DNA nanostructure having at least two fluorescently-labeled regions and a target binding moiety, wherein the locations of each of the fluorescently-labeled regions on the nucleic acid nanostructure are such that a pattern of the fluorescent labels of the nucleic acid barcode probe and the identity of the target binding moiety is determinable based on the emission of visible light by the fluorescently-labeled regions.

In some embodiments, each of the fluorescently-labeled regions has a center that is located at least about 25 nm, at least about 50 nm, at least about 100 nm, at least about 200 nm, or at least about 250 nm from the centers of the other fluorescently-labeled regions.

These and other aspects and embodiments of the invention will be described in greater detail herein.

BRIEF DESCRIPTION OF DRAWINGS

(FIG. 1A) Two schematic drawings of the Blue--Red-Green (BRG, "--" and "-" denotes larger and smaller inter-zone distance in the barcode, respectively) barcode with a segment diagram on the top and a 3D view at the bottom. The main-body of the barcode is a DNA nanotube formed from by dimerizing two origami monomers, each consisting of 28 segments with 42-bp (13.6 nm) length. The grey segment in the middle represents the junction where the two monomers are joined together through cross-hybridization between their scaffolds and staples. Three 84-bp zones of the nanotube are fluorescently labeled (shown as blue, red and green segments) to produce the BRG barcode with an inter-zone distance of 450-nm between the first two zones and 270-nm between the last two. Note that each zone is only labeled with one fluorophore species. The resulting barcodes are thus referred as single-labeled-zone barcodes. (FIG. 1B) 3D cartoons showing the details of one fluorescently labeled zone. Left: a scaffold-plus-staple model of such an 84-bp zone before labeling. Each of the twelve 63-base-long staples (shown in varying shades of grey) contains two parts: the 42-base region at the 5'-end weaves through three double-helices to fold the scaffold (shown in black) into a six-helix bundle nanotube; and the 21-base extension at the 3'-end protrudes out for fluorescent labeling. Middle: an identical but simplified model to emphasize the six-helix bundle structure (each helix shown as a semi-transparent grey cylinder) and the positioning of the twelve 21-base staple extensions (each shown as a light-grey curl). Right: Cartoon representation of a "green" 84-bp zone. The labeling is achieved by hybridizing the Cy3 (shown as glowing spheres at the 3'-ends) modified strands to the staple extensions.

(FIG. 2A) Superimposed TIRF microscopy images of five barcode species (top) and the statistics from manual counting (bottom). From left to right are the BBB, BRG, BRR, GRG and RGB barcodes with a representative image on top of the corresponding bar-graph. Each bar-graph is generated based on the manual sorting and counting of the objects found in a 50×50 μm$^2$ image (~40 barcodes, the exact sample size N is noted beside the corresponding bar-graph). (FIG. 2B) A representative image of the equimolar mixture of 27 barcode species. (FIG. 2C) Statistics obtained by analyzing twenty-seven 50×50 μm$^2$ images of the 27 barcode mixture (1,500 barcodes in total). Left: barcode counts of the 27 species (average count of 55 with a standard deviation of 9). A representative TIRF image (1.4×0.7 μm$^2$) of each barcode type is placed underneath the corresponding bar. Right: sorting result of the observed objects shown as a pie-chart. The bar-graphs and the pie-chart include correct barcodes (qualified barcode with expected identity); incorrect barcodes (qualified barcode with unexpected identity); monomer nanotubes (one spot or two connecting spots); barcodes with wrong geometry (i.e., bending angle <120°); and barcodes containing at least one spot with two colors. In the 27-barcode pool, correct vs. incorrect barcodes were not distinguishable because all barcode types are expected. As a result the bars and pie representing the qualified barcodes in (FIG. 2C) are shown. Scale bars: 5 μm.

(FIG. 3A) TIRF image of BRG nano-barcodes. (FIG. 3B) Software constructed image of (FIG. 3A), inset showing calculation of barcode bending angle. (FIG. 3C) TIRF image of BRG nano-barcodes. (FIG. 3D) Software constructed image of (FIG. 3C). (FIG. 3E) Theoretical designed distances between each region of BRG (upper) and GRG (lower) nano-barcodes. Scale bar: 10 pixels or 0.714 μm.

(FIG. 4A) A GRG barcode with a capture probe is biotinylated as a result of the target binding and a nude BRG barcode stays untouched. Note that the drawing is not to scale. (FIG. 4B) TIRF images of nano-barcodes immobilized on streptavidin coated glass cover-slip. Left: with target; Right: without target. (FIG. 4C) Statistical detection result showing the average barcode counts per 71.4×71.4 μm$^2$ area. Error bars represent the standard deviation.

FIGS. 5A-5D. Dual-labeled-zone fluorescent barcodes. (FIG. 5A) Typical TIRF microscopy images of five selected barcode species, shown both in separate channels and after superimposing. Scale bar: 5 μm. (FIG. 5B) Statistics obtained by analyzing two 50×50 μm$^2$ images of each barcode species (~85 barcodes, the exact sample size N is noted beside the corresponding bar-graph). The barcode types are noted under the x-axis of the diagram. The bar graph includes correct barcodes (correct geometry and color identity); incorrect barcodes (correct geometry but incorrect color identity); monomer nanotubes (one spot or two connecting spots); and barcodes with wrong geometry (i.e., bending angle <120°). (FIG. 5C) Computer-aided barcode counting results of the 72-barcode pool (N=2,617) and the 216-barcode pool (N=7,243) plotted as bar-graphs with descending barcode counts from left to right (data not shown). A computer-generated reference barcode image is placed underneath the corresponding bar. (FIG. 5D) A table containing one representative TIRF image (1.4×0.7 μm$^2$) for each of the 216 dual-labeled-zone barcode species.

(FIG. 6A) Scheme of DNA-PAINT used for super-resolution barcode imaging. The 400 nm nanotube consists of 4 binding zones spaced by ~114 nm. Each zone can be decorated with the desired combination of "docking" sequences for imager strands. The orthogonal imager strands bind transiently to their respective "docking" sites on the nanotube, creating the necessary "blinking" for super-resolution reconstruction (FIG. 6B) Top: Segment diagram (similar to the one used in FIG. 1B) of the DNA nanotube monomers used for creating five barcodes for super-resolution imaging. Bottom: super-resolution images of the five barcodes shown in each channel separately and as an overlay of all channels. Scale bar: 100 nm. (FIG. 6C) Super-resolution image showing all five barcodes in one mixture. Scale bar: 500 nm.

(FIG. 7A) Cartoon illustrating the tagging mechanism. The biotinylated barcodes are anchored on the yeast cell through streptavidin molecules bound to biotinylated polyclonal antibodies coated on the yeast surface. Only two of the ten biotinylated staples on the barcode are shown here for clarity. (FIG. 7B) Overlaid microscope images (acquired in bright field and TIRF) of the yeast cells treated with the barcodes. Top: Yeast cells treated as illustrated in (FIG. 7A). Bottom: Negative control: yeast cells treated with non-biotinylated barcodes. Scale bars: 5 μm.

(FIG. 8A) A schematic of three identical ~400-nm long DNA nanotubes are linked to the outer edge of a DNA ring with diameter of ~60 nm through the hybridization between staple extensions. The ring and the end of the tube are labeled by Cy3 and Cy5, respectively. (FIG. 8B) A representative TIRF microscope image of the barcode shown in (FIG. 8A). Scale bar: 5 μm.

DETAILED DESCRIPTION OF INVENTION

Figure 1A:
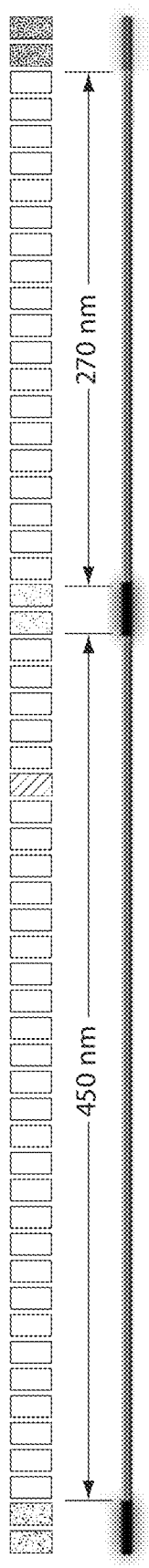
FIGS. 1A-1B. Design of the DNA nanotube based barcode.

Provided herein are nucleic acid (e.g., DNA) nanostructure barcode probes that are fully addressable and able to be read using standard fluorescent microscope.

Previously described molecular barcodes are constructed using one of two strategies: (1) By combining multiple spectrally non-overlapping fluorophores in a controlled molar ratio to generate a mixed color signature; or (2) by separating fluorophores beyond the diffraction limit (~200 nm) and arranging them in a specific geometric pattern. The first category of barcode has been made, for example, from dendrimeric DNA (see, e.g., Li et al., *Nat. Biotechnol.* 23:885-889 (2005)), self-assembled 2D DNA arrays (see, e.g., Lin et al., *Nano Lett.* 7:507-512 (2007)) and quantum dots (see, e.g., Han et al., *Nat. Biotechnol.* 19:631-635 (2001)). The successful construction and decoding of such barcodes heavily depends on both the fluorescent labeling efficiency and the imaging instrument's ability to precisely detect different fluorescent intensity levels.

In contrast, barcodes constructed according to the second strategy are more robust, and can be constructed and detected even when the labeling efficiency and imaging conditions are sub-optimal. Furthermore, when such methods are used, the ability to multiplex increases exponentially with each additional fluorescent spot that is incorporated. Examples of barcodes that fall in this category include rare-earth doped glass microfibers (~100 μm long) (see, e.g., Dejneka et al., *Proc. Nat. Acad. Sci. USA* 100:389-393 (2003)) and double-stranded linear DNA with one strand fluorescently tagged at specific locations (2-5 μm long) (see, e.g., Xiao et al., *Nat. Methods* 6:199-201 (2009) and Geiss et al., *Nat. Biotechnol.* 26:317-325 (2008)). However, existing methods using this strategy are limited both in the addressability of the fluorescent spots and because, in the absence of specialized equipment, the labeled barcodes will fold into a conformation that brings the fluorescent spots within the diffraction limit of visible light, rendering the barcode unreadable using a fluorescent microscope.

The instant inventors recognized that the problems associated with existing molecular barcode strategies could be addressed by using nucleic acid nanostructures such as DNA nanostructures to create novel molecular barcode probes. Nucleic acids such as DNA may be folded into predetermined one-, two- or three-dimensional nanostructures using a variety of techniques, such as DNA origami (Rothemund US-2007/0117109 A1), single-stranded tiles (Yin et al., "Programming DNA Tube Circumferences," *Science* (2008): 321: 824-826), DNA hairpins (Yin et al. US-2009/0011956 A1; Yin et al., "Programming biomolecular self-assembly pathways," *Nature* (2008) 451:318-323), and others.

In general, the DNA origami process involves the folding of one or more long, "scaffold" DNA strands into a particular shape using a plurality of rationally designed "staple" DNA strands. The sequences of the staple strands are designed such that they hybridize to particular portions of the scaffold strands and, in doing so, force the scaffold strands into a particular shape. Methods useful in the making of DNA origami structures can be found, for example, in U.S. Pat. App. Pub. Nos. 2007/0117109, 201008/0287668, 2010/0069621 and 2010/0216978, each of which is incorporated by reference in its entirety. Staple design can be facilitated using, for example, caDNAno software, available on the internet at the cadnano website.

In certain embodiments, a DNA nanostructure barcode probe may include a DNA nanostructure made of one or more scaffold strands held in a specific shape by rationally designed staple strands. The sequence listing provides the nucleotide sequence of a scaffold strand, as SEQ ID NO:1, that may be used to construct an exemplary DNA origami barcode probe. The sequence listing also provides nucleotide sequences of staple strands, as SEQ ID NOs: 13-361, that may be used to construct an exemplary DNA origami barcode probe, together with the scaffold strand represented by SEQ ID NO:1. As will be discussed in greater detail herein, SEQ ID NOs: 13-186 represent nucleotide sequences of staple strands used to form a front monomer and SEQ ID NOs: 187-361 represent nucleotide sequences of staple strands used to form a rear monomer in an exemplary DNA origami barcode probe. As used herein, the term "DNA nanostructures" is used for convenience and it is to be understood that the invention contemplates nucleic acid nanostructures generally. The nanostructures of the invention may be linear (e.g., nanorods) or non-linear (e.g., star-shaped, triangular, etc.).

The DNA nanostructure has at least two non-overlapping, fluorescently-labeled regions. In certain embodiments, the DNA nanostructure barcode probe has at least 3, 4, 5, 6, 7, 8, 9, 10, 11 or 12 non-overlapping, fluorescently-labeled regions.

The fluorophore pattern of the probe is determined using light microscopy. In some embodiments, each of the fluorescently labeled regions can be visibly distinguished using a fluorescent light microscope. In some of these embodiments, the center of each fluorescently labeled region is separated from the centers of other fluorescently labeled regions by a distance greater than the visible light diffraction limit of visible light (i.e. at least 200 nm). In certain embodiments, therefore, each fluorescently labeled region is at least 200 nm from any other fluorescently labeled region. In some embodiments, each fluorescently labeled region is at least 250 nm from any other fluorescently labeled region.

In some embodiments, even higher resolution is achievable and the fluorescently labeled regions may be spaced apart from each other at even shorter distances (i.e., a distance of less than 200 nm). Accordingly, in some embodiments, the distance between the fluorescently labeled regions may be equal to or about 175 nm, 150 nm, 125 nm, 100 nm, 75 nm, 50 nm, 25 nm, or smaller distances. When the fluorescently labeled regions are spaced apart at distances that are less than the diffraction limit of visible light, the barcoded probes are imaged using super-resolution techniques such as Point Accumulation for Imaging in Nanoscale Topography (PAINT, DNA-PAINT), Stimulated Emission Depletion Microscopy (STED), Reversible Saturable Optical Fluorescence Transitions (RESOLFT), Stochastic Optical Reconstruction Microscopy (STORM, dSTORM), Photoactivated Localization Microscopy (PALM), Blink Microscopy (BM), and any other form of super-resolution microscopy.

It is to be understood that the term "fluorescently-labeled region" embraces regions that are stably labeled and those that are transiently labeled with fluorophore-bearing moieties such as fluorophore-bearing oligonucleotides that are complementary to a handle domain or docking strand (or sequence), as described in greater detail herein. In some instances, the barcode probes of the invention are provided with such fluorophore-bearing oligonucleotides bound thereto, and therefore these probes would be fluorescent. In other instances, the barcode probes of the invention are provided without such fluorophore-bearing oligonucleotides bound thereto, and therefore these probes may not be fluorescent until they are bound to a fluorophore-bearing oligonucleotide. In these latter instances, a probe may be provided together with a plurality of fluorophore-bearing oligonucleotides that are specific for (e.g., typically, complementary to) the handle domains or docking strands of the probe. The probes and the oligonucleotides may be provided in a kit, optionally with each in a separate container within the kit.

The positions of the fluorescently labeled regions can be selected such that the orientation of the DNA nanostructure barcode may be determinable through visualization of the barcode on a fluorescent microscope (typically by some form of asymmetry in the arrangement of the labeled regions or by some arrangement convention, such a particular color or pattern reserved to indicate an end of the barcode). In some instances, orientation information is unnecessary and the barcode pattern need not be absolutely unique. Thus, barcodes with even just two labels may be used, and the presence and/or intensity of various labels provides the information required.

Figure 1B:
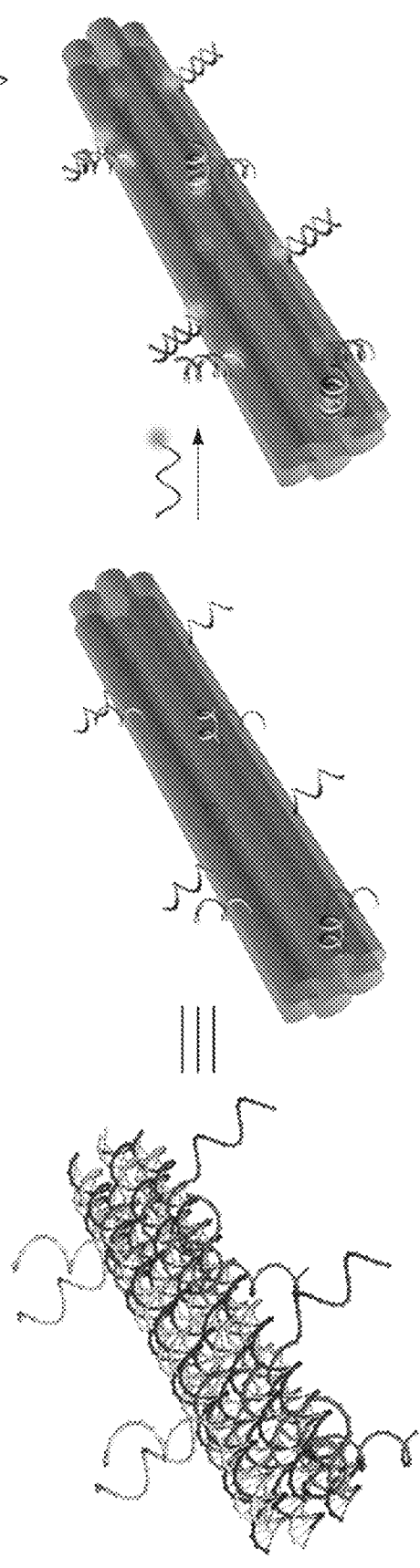

In some instances, the fluorescently labeled regions are arranged in a linear manner. An examples is shown in, for example, FIGS. 1A-1B. The fluorescently labeled regions may however be arranged in a non-linear manner as well. An example is shown in FIG. 8. Other non-linear arrangements will be apparent to those of ordinary skill in the art and are embraced by the invention. In some instances, a non-linear orientation (or arrangement or geometry) of the fluorescently labeled regions is used to detect and/or identify analytes. In some instances, the signal (including for example the color or color combination) of non-linearly arranged fluorescently labeled regions is used to detect and/or identify analytes. In still other instances, orientation and signal are used together to detect and/or identify analytes. Thus, it is to be understood that the nano structure may be linear or non-linear and/or the arrangement of the fluorescently labeled regions may be linear or non-linear.

The DNA nanostructure, once assembled, is sufficiently immutable in a resting state (i.e., in the absence of external influence from e.g. an electrical field) that the spatial pattern of the fluorescent regions can be detected using light microscopy in that resting state. Portions of the nanostructure may be flexible, such as unlabeled portions. In some embodiments, a probe may include a (relatively) rigid portion carrying label and an unlabeled flexible portion. In some embodiments, a probe may have two rigid labeled regions connected by a deformable linker.

In certain embodiments, the DNA nanostructure of the DNA barcode probe can be of any one-, two- or three dimensional shape that is able to support at least three fluorescently labeled regions at least 200 nm apart from each other. As stated herein, however, the invention is not so limited as nanostructures having fluorescently labeled regions spaced at distances of less than 200 nm from each other are also contemplated.

In certain embodiments, the DNA nanostructure is a nanotube. In some embodiments, the nanotube is at least 200, 300, 400, 500, 600, 700 or 800 nm long. In certain embodiments, the DNA nanostructure is a six helix bundle dimer nanotube. Description of DNA nanotube design (via DNA origami) can be found in, for example, Douglas et al., Proc. Natl. Acad. Sci. USA 104:6644-6648 (2006) and U.S. Pat. App. Pub. No. 2010/0216978, each of which is incorporated by reference in its entirety.

In some embodiments, the DNA barcode probes are designed such that the orientation of the DNA barcode probe is determinable based on the emission of visible light by the fluorescently-labeled regions. Any property of the barcode can be used to render the orientation of the DNA barcode can be determinable. For example, if the DNA barcode probe has a substantially one-dimensional (linear) structure, such as a nanotube, the fluorescently labeled regions can be positioned asymmetrically along the DNA nanostructure. The orientation of a substantially one-dimensional (linear) DNA barcode probe can also be made determinable by asymmetrically using a particular fluorophore or combination of fluorophores to label one side of the DNA nanostructure consistently. If the DNA nanostructure is two- or three-dimensional, the orientation of the DNA barcode probe can also be rendered determinable based, for example, on an asymmetry of the shape of the structure itself.

In certain embodiments, the fluorescently labeled regions of the DNA barcode probe are generated by labeling specific staples of the DNA nanostructure with a fluorescent moiety. The staples can be directly labeled or indirectly labeled. As used herein, the term "directly labeled" refers to a nucleic acid that is covalently bonded to a detectable moiety. In contrast, the term "indirectly labeled" refers to a nucleic acid that is attached to a detectable moiety through one or more non-covalent interactions.

In certain embodiments, certain staples of the DNA nanostructure are directly labeled with a fluorescent moiety. In such embodiments, the staple can be, for example, synthesized with a particular fluorescent moiety attached, or covalently bonded to a fluorescent moiety prior to its incorporation into the DNA nanostructure.

Any combination of fluorescent moieties may be used in a single barcode, provided the fluorescent signal from each labeled region is detectable. Preferably, the combination of fluorescent moieties is chosen so that there is no energy transfer between the fluorescent moieties (i.e., the fluorophore combination used on a single barcode probe does not contain pairs of fluorophores that act together as a donor-acceptor pair).

In some embodiments, certain staples of the DNA nanostructure are indirectly labeled with a fluorescent moiety. In such embodiments, such staples can be synthesized to have at least two domains, a staple domain and a handle domain. The staple domain is a region (or nucleotide sequence) of the staple that hybridizes to the scaffold strand to contribute to the formation and stability of the DNA nanostructure. The handle domain contains additional nucleic acid sequence that is not necessary for the creation of the DNA nanostructure. Before, during or after the formation of the DNA nanostructure, the handle sequences are available to be hybridized by oligonucleotides having a complementary DNA sequence. Thus, such staples can be indirectly labeled by hybridizing the handle domain to another nucleic acid that has a nucleic acid sequence complementary to the handle and that is itself either directly or indirectly labeled with a fluorescent moiety.

In some embodiments, each fluorescent region of the DNA barcode probe includes at least one fluorescently labeled staple. In certain embodiments, the fluorescently labeled region may include a plurality of fluorescently labeled staples. For example, in certain embodiments, each fluorescently labeled region may include at least 2, 3, 4, 5, 6, 7, 8, 9, 10, 11, 12, or more fluorescently labeled staples. In regions designed to have multiple staples labeled, all the staples may be labeled by a single type of fluorophore, or the staples may be labeled by a combination of fluorophore types. For example, in certain embodiments, a fluorescently labeled region is designed to be labeled by multiple types of fluorophores present at a predetermined ratio. An example of this latter type of labeling, referred to as dual-labeling, is demonstrated in the Examples. In dual-labeling, a single region is labeled with two fluorophores in a predetermined ratio, to yield a fluorescent signal that is distinguishable from either of the contributing fluorophores. In this way, the variety of barcode probes is increased.

In still other embodiments, the barcode probe may comprise one or more regions that are transiently labeled with fluorophore-bearing oligonucleotide strands. These embodiments may be used when the fluorescently labeled regions are within 200 nm of each other. In some embodiments, all the regions contributing to the barcode will be designed to be transiently labeled. Transient labeling of a region is achieved by using a nanostructure comprised of staple strands with handle domains that are shorter in length than those used for more permanent binding of a fluorescently labeled oligonucleotide. As an example, permanent (or stable) binding of fluorophore-bearing oligonucleotides to a handle domain of a staple strand can be achieved using oligonucleotides and handle domains that are about 21 nucleotides in length. When shorter oligonucleotides and handle domains are used, the strength of binding between the two is reduced and accordingly they are more likely to dissociate than are longer strands. At room temperature, oligonucleotides and handle domains that are about 9 nucleotides in length associate with each other only transiently. As will be understood in the art, at higher temperatures, the length of the oligonucleotide and handle domain will typically be increased in order to achieve the same association/dissociation kinetics.

Accordingly, the invention contemplates handle domains that are directly or indirectly labeled with fluorophores as well as those that are transiently labeled with fluorophores. The length of the handle domain (and similarly its complementary oligonucleotide) will depend upon the nature of the binding (i.e., whether it is intended to be permanent or transient binding), and the reaction conditions such as but not limited to temperature, salt concentration, and the like. Such lengths may range, without limitation, from about 5 nucleotides to 30 nucleotides, or from about 7 nucleotides to about 25 nucleotides, or from about 9 nucleotides to about 21 nucleotides.

In some embodiments, the DNA barcode probe may further include a target binding moiety that acts as a binding partner for the target (or analyte) of interest. As used herein, the term "binding" refers to an association between at least two molecules due to, for example, electrostatic, hydrophobic, ionic and/or hydrogen-bond interactions under physiological conditions. Such a target binding moiety can be, for example, without limitation, a nucleic acid such as an oligonucleotide, a protein or peptide such as an antibody or antibody fragment, a carbohydrate or a polysaccharide, or a small molecule. The target binding moiety and the target to which it binds can also be viewed in a receptor and ligand relationship. In certain embodiments, the DNA barcode probe may include multiple target capture moieties, which may be identical or different.

The target capture moiety can be attached to the DNA nanostructure of the DNA barcode probe using any method known in the art. For example, the target capture moiety can be covalently bonded to a staple strand or a scaffold strand. The capture moiety can also be indirectly attached to either a staple strand or the scaffold strand by, for example, hybridizing to a handle domain of a staple strand, as described above.

In certain embodiments, the DNA barcode probe may include a target binding moiety that is an oligonucleotide or other nucleic acid capable of hybridizing to a target nucleic acid. In general, an oligonucleotide is capable of hybridizing to a target nucleic acid if it includes a nucleic acid sequence that is substantially complementary a sequence of the target nucleic acid. In certain embodiments, the oligonucleotide may include a sequence that is perfectly complementary to a target (i.e. that is able to base pair at every nucleotide with the target sequence). In some embodiments, the oligonucleotide is less than perfectly complementary to the target but is still able to hybridize to a target nucleic acid under certain conditions. Thus, in certain embodiments the sequence of the oligonucleotide is at least 10%, 20%, 30%, 40%, 50%, 60%, 65%, 70%, 75%, 80%, 85%, 90% or 95% complementary to a sequence of the target nucleic acid. In certain embodiments, the DNA barcode probe may include a target binding moiety that is an aptamer.

In certain embodiments, the DNA barcode probe may include a target binding moiety that is an antibody. As used herein, the term "antibody" includes full-length antibodies and any antigen binding fragment (i.e., "antigen-binding portion") or single chain thereof. The term "antibody" includes, but is not limited to, a glycoprotein comprising at least two heavy (H) chains and two light (L) chains interconnected by disulfide bonds, or an antigen binding portion thereof. Antibodies may be polyclonal or monoclonal; xenogeneic, allogeneic, or syngeneic; or modified forms thereof (e.g., humanized, chimeric).

As used herein, the phrase "antigen-binding portion" of an antibody, refers to one or more fragments of an antibody that retain the ability to specifically bind to an antigen. The antigen-binding function of an antibody can be performed by fragments of a full-length antibody. Examples of binding fragments encompassed within the term "antigen-binding portion" of an antibody include (i) a Fab fragment, a monovalent fragment consisting of the $V_H$, $V_L$, CL and CH1 domains; (ii) a F(ab')2 fragment, a bivalent fragment comprising two Fab fragments linked by a disulfide bridge at the hinge region; (iii) a Fd fragment consisting of the $V_H$ and CH1 domains; (iv) a Fv fragment consisting of the $V_H$ and $V_L$ domains of a single arm of an antibody, (v) a dAb fragment (Ward et al., (1989) Nature 341:544 546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); see e.g., Bird et al. (1988) Science 242:423 426; and Huston et al. (1988) Proc. Natl. Acad. Sci. USA 85:5879 5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

In certain embodiments the target binding moiety is a protein or peptide. For example, a protein or peptide can be used to bind the DNA barcode probe to the protein's ligand. DNA barcodes having protein or peptide target binding moieties can also be used, for example, to identify antibodies or receptors such as but not limited to cell surface receptors such as but not limited to T cell receptors and B cell receptors and intracellular receptors such as but not limited to hormone receptors that are able to bind to an epitope present on the protein or peptide.

In certain embodiments, the target binding moiety is a small molecule. DNA barcode probes having small molecule target binding moieties can, for example, be used to identify molecular or cellular targets of small molecules of interest. Furthermore, libraries of small molecules, where each small molecule is individually tagged with a DNA barcode, can be used in small molecule library screens to identify small molecules that specifically bind to a target of interest.

DNA barcode probes may be provided as a population of distinct species. The number of distinct barcode probes in the population is limited only by the multiplexing capability of the particular barcodes in the population. In certain embodiments, the population contains at least 10, 50, 100, 500, 1000, 2000, 3000, 4000, 5000, $10^4$, 50000, $10^5$, $10^5$, $10^6$, $10^7$, $10^8$, $10^9$, $10^{10}$, $10^{11}$ distinct barcode probes. The population may contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more distinct species. The population may contain less than or equal to about 5, 10, 15, 20, 25, 30, 35, 40, 45, 50, 55, 60, 65, 70, 75, 80, 85, 90, 95, 100 or more distinct species. In some embodiments, the population comprises 216 distinct barcode probes. The barcode probes described herein are sufficiently adaptable and expandable to permit creation of such large-scale populations of distinguishable species.

Methods of Use

The DNA nanostructure barcode probes can be used, inter alia, in any assay in which existing molecular barcode technologies are used. For example, the DNA barcode probes can be used according to the methods described in U.S. Pat. App. Pub. No. 2010/0015607, the content of which is incorporated by reference in its entirety.

Typically assays include detection assays including diagnostic assays, prognostic assays, patient monitoring assays, screening assays, biowarfare assays, forensic analysis assays, prenatal genomic diagnostic assays, and the like. The assay may be an in vitro assay or an in vivo assay. The sample being analyzed may be a biological sample, such as blood, sputum, lymph, mucous, stool, urine and the like. The sample may be an environmental sample such as a water sample, an air sample, a food sample, and the like. The assay may be carried out with one or more components of the binding reaction immobilized. Thus, the targets or the barcodes may be immobilized. The assay may be carried out with one or more components of the binding reaction non-immobilized. The assays may involve detection of a number of targets in a sample, essentially at the same time, in view of the multiplexing potential offered by the barcode probes of the invention. As an example, an assay may be used to detect a particular cell type (e.g., based on a specific cell surface receptor) and a particular genetic mutation in that particular cell type. In this way, an end user may be able to determine how many cells of a particular type carry the mutation of interest, as an example.

In certain embodiments, a method of identifying a target nucleic acid may include contacting the target nucleic acid with a DNA barcode having an oligonucleotide target capture moiety that includes a nucleic acid sequence capable of hybridizing to a sequence of the target nucleic acid. In certain embodiments, the target nucleic acid is contacted with a DNA barcode probe under conditions such that the target nucleic acid binds to the DNA barcode probe. In some embodiments, the target nucleic acid is then separated from at least some material that is not bound to the target nucleic acid. In certain embodiments the presence of the target nucleic acid is then determined by detecting the presence of the DNA barcode probe bound to the target nucleic acid. The detection of the DNA barcode probe can be accomplished by any appropriate method known in the art, including through fluorescent microscopy.

In some embodiments, the above-described method may further include immobilizing a capture probe containing a nucleic acid sequence complementary to a second target nucleic acid sequence to a solid support. In some embodiments the target nucleic acid is contacted with both the capture probe and the DNA barcode probe. The target nucleic acid can be contacted by the capture probe first, the DNA barcode probe first, or by both probes simultaneously. The capture probe can be immobilized on the solid support before hybridizing to the target nucleic acid, after hybridizing to the target nucleic acid, or simultaneously with hybridizing to the target nucleic acid. In such embodiments, the presence of the target nucleic acid will cause the formation of a tertiary complex that includes the capture probe, the target nucleic acid and the DNA barcode probe, immobilized to a solid support. As described above, the presence of the target nucleic acid is then determined by detecting the presence of the DNA barcode probe by any appropriate method known in the art, including through fluorescent microscopy In certain embodiments, a method of identifying a target protein or cell may include contacting the target protein or cell with a DNA barcode probe described herein. In certain embodiments, the DNA probe has a protein, peptide or antibody target capture moiety. In some embodiments, the DNA barcode probe is contacted to a target cell or protein under conditions such that the target cell or protein binds to the DNA barcode probe. In some embodiments, the method further includes the step of separating the target protein or cell from at least some material that is not bound to the target protein or cell. In certain embodiments, the method further includes identifying a target protein or cell by detecting the presence of the DNA barcode probe bound to the target protein or cell. In some embodiments, the target protein is an antibody or receptor such as but not limited to a T cell receptor.

It will be appreciated that for some of the aspects and embodiments of the invention, it is preferable for the barcode probe and/or target to remain stationary during image acquisition, particularly if a super-resolution approach is being used and/or if the imaging technique requires superimposition of separately acquired images.

Super-Resolution Imaging

As discussed herein, in some aspects of the invention, the barcode probes comprise fluorescently labeled regions that are spaced at distances less than 200 nm (i.e., the diffraction limit of visible light). In some of these instances, the probe is contacted to a sample and once bound to one or more components of that sample it is exposed to soluble oligonucleotides each of which is specific for one of the regions and is labeled with fluorophores. Such soluble, transiently binding oligonucleotides may be referred to herein as "imager" strands. In some instances, the unbound components in the sample are removed prior to the addition of the fluorophore-bearing oligonucleotides. The presence of the barcode probe (and its identity based on its barcode) is then determined by imaging the remaining sample components using a series of single time lapsed images or a time lapsed movie in order to detect the binding of a fluorophore-bearing oligonucleotide to its complement on the probe. The complement on the probe may be referred to herein as a "docking" strand. The conditions are set such that at any given time only a single fluorophore-bearing oligonucleotide is bound to the barcode probe. If only a single fluorophore is bound at any given time, its color identity can be determined even if the neighboring regions are less than 200 nm away (since there would be no fluorophores bound to the neighboring regions at the same time). In this way, one is able to position adjacent "fluorescently labeled" regions at distances of less than 200 nm, and thereby generate an even greater diversity of barcodes. It is to be understood that in these embodiments, the fluorescently labeled regions are only transiently fluorescent and that the barcodes are only fluorescent when bound by imager strands.

In some embodiments, the imager and/or docking strands are about 5 to about 18 nucleotides in length, or about 6 to about 15 nucleotides in length, or about 7 to about 12 nucleotides in length. In some embodiments, the length is about 8, 9, 10, 11 or 12 nucleotides.

The art is familiar with other localization-based super-resolution fluorescence techniques including, for example, the STORM technique as described in U.S. Pat. No. 7,838,302, the disclosure of which relating to STORM is incorporated by reference herein. The invention contemplates labeling of the nanostructure barcode probes in any manner sufficient for any super-resolution technique.

In other aspects of the invention, the nanostructure barcode probes of the invention may be used to calibrate and/or confirm calibration of fluorescence microscopy equipment, including standard or conventional fluorescence microscopes, confocal microscopes, super-resolution fluorescence microscopes, and the like. Accordingly, nanostructure barcode probes may be used as calibration standards (or tools). Of particular interest in these instances are the barcode probes having "fluorescently-labeled" regions that are spaced apart at less than the diffraction limit of visible light (i.e., less than about 200 nm). When used in this manner, the probes may or may not have a target binding moiety. As an example, they may comprise a target binding moiety such as biotin or streptavidin that facilitates their immobilization for imaging purposes.

EXAMPLES

Example 1: Creation of a DNA Barcode

DNA origami barcode probes were constructed by fluorescently labeling three separate regions of an 800-nm six-helix bundle dimer nanotube (FIG. 1). Each of the approximately 28 nm long fluorescently labeled regions was modified with twelve oligonucleotides attached to one of the three fluorophores (rhodamine-green, Cy3 or Cy5). The DNA origami barcode probe was designed to be asymmetric by placing the first two labeled regions further apart (approximately 460 nm apart) than the last two (approximately 270 nm apart). It is to be understood that other arrangements, including symmetric arrangements, are also contemplated by the invention.

The main structure of the DNA origami barcode probe is a DNA six-helix bundle nanotube dimer designed using the caDNAno software available at the cadnano website. The sequence of the scaffold strand used for each monomer is provided as SEQ ID NO:1. The sequences of the staples used in the construction of the DNA origami barcode are provided as SEQ ID NOs: 13-361. Certain selected staples were elongated (after rational design) to include 21-nt single stranded overhangs (handles) for fluorescent labeling. Table 1 provides the handle and anti-handle sequences used.

TABLE 1

DNA sequences used for fluorescently labeling nano-barcode.

| Name | Sequence (SEQ. ID. NO.) |
|---|---|
| Handle 1 | 5'-TTCCTCTACCACCTACATCAC-3' (SEQ ID NO: 2) |
| Handle 2 | 5'-TAACATTCCTAACTTCTCATA-3' (SEQ ID NO: 3) |
| "Blue" anti-handle 1 | 5'-GTGATGTAGGTGGTAGAGGAA/rhodamine green/-3' (SEQ ID NO: 4) |
| "Green" anti-handle 1 | 5'-GTGATGTAGGTGGTAGAGGAATTT/Cy3/-3' (SEQ ID NO: 5) |
| "Red" anti-handle 1 | 5'-GTGATGTAGGTGGTAGAGGAA/Cy5/-3' (SEQ ID NO: 6) |
| "Blue" anti-handle 2 | 5'-TATGAGAAGTTAGGAATGTTA/Alexa Fluor 488/-3' (SEQ ID NO: 7) |
| "Green" anti-handle 2 | 5'-TATGAGAAGTTAGGAATGTTA/Cy3/-3' (SEQ ID NO: 8) |
| "Red" anti-handle 2 | 5'-TATGAGAAGTTAGGAATGTTA/Cy5/-3' (SEQ ID NO: 9) |

Accordingly, of the staple strands provided in the Sequence Listing, SEQ ID NOs: 16, 17, 70-73, 126-129, 182 and 183 are labeled "blue"; SEQ ID NOs: 195, 196, 239, 240, 251, 252, 295, 296, 307, 308, 351 and 352 are labeled "red"; and SEQ ID NOs: 216-219, 272-275 and 328-331 are labeled "green".

caDNAno JSON files showing the arrangement of the front and rear monomers of the probe are provided in the computer program listing appendix as "6ht-v5-1color-1.json" and "6ht-v6-2color-1.json" respectively.

To assemble the DNA origami barcode probe, the front and rear monomers were each assembled and fluorescently labeled in a separate test tube and then mixed together to form the dimer. The assembly of each monomer is accomplished in one-pot reaction by mixing 100 nM scaffold strand derived from M13 bacteriophage (termed p'7308) (SEQ ID NO:1) with a pool of oligonucleotide staple strands (SEQ ID NOs: 13-186 for the front monomer and 187-361 for the rear monomer; 600 nM of each; reverse-phase cartridge purified, Bioneer Inc.) in folding buffer containing 5 mM Tris, 1 mM EDTA, 20 mM MgCl$_2$, 50 mM NaCl (pH 8) and subjecting the mixture to a thermal-annealing ramp that cooled from 80° C. to 60° C. over the course of 80 minutes and then cooled from 60° C. to 24° C. over 15 hours. Excessive staples were removed by polyethylene glycol (PEG) fractionation before each monomer was incubated with anti-handles carrying appropriate fluorophores at 1:1.2 molar ratio for labeling. For dimerization, a stoichiometric amount of the fluorescently labeled front and rear monomers were mixed and incubated a 37° C. for 2 hours. The final product was purified by agarose gel (non-denaturing, 1.0%) electrophoresis. The purified nano-barcode can be stored at −20° C. for at least 3 months.

Although this example uses a barcode made of two monomers, a DNA barcode probe could include 3, 4, 5, or more monomers. The platform is therefore scalable to any desired level, and can provide any desired number of distinct probes.

Example 2: Detection of a Singly-Labeled DNA Barcode Using Fluorescent Microscopy Two of the monomer nanotubes were folded and fluorescently labeled separately and combined together as described above to yield the nano-barcode. The final product was purified by agarose gel electrophoresis and directly deposited on a glass slide for imaging using a total internal reflection fluorescence microscope (TIRFM). In brief, 5 μL of the purified nano-barcode (~20 pM) was deposited on a glass slide, sandwiched by a coverslip (No. 1.5, 18×18 mm$^2$, ~0.17 mm thick) and let sit for 5 minutes before being imaged on a Leica DM16000B TIRFM. The samples were imaged sequentially through three channels, each assigned a false color (blue, green and red). For the blue channel, the 488 nm laser beam was reflected by a dichroic mirror (430/505/575/670) and shined on the sample through a 100× objective (HCX PL APO 100×/1.47 oil CORR TIRF, Leica). The emission light was collected through the same objective, filtered through the same dichroic mirror and an external emission filter (525/36) and integrated for 800 ms on an EM-CCD camera (Hamamatsu C9100-02). For the green and red channels, similar configurations were used except for the excitation laser (561 and 635 nm, respectively), emission filter (605/52 and 705/72, respectively) and exposure time (500 and 700 ms, respectively). The imaging process was automatically controlled by a Leica LAS software. The images were processed by Image J and a custom written software for decoding.

The following false-colors were assigned to the fluorescently labeled regions: Alexa Fluor 488/rhodamine green (blue), Cy3 (green) and Cy5 (red). TIRFM images resolved the DNA origami barcode as a strip of three distinct bright spots. Notably, the distance between blue and green spots is farther than that between green and red showing the asymmetry of the barcode (data not shown)

A DNA origami barcode system having three fluorescently labeled regions, each of which is labeled by one of three distinct fluorophores can generate $3^3$ (27) distinct DNA origami barcode probes. All 27 possible DNA origami barcode probes were assembled separately and purified together by agarose gel electrophoresis.

Figure 2A:
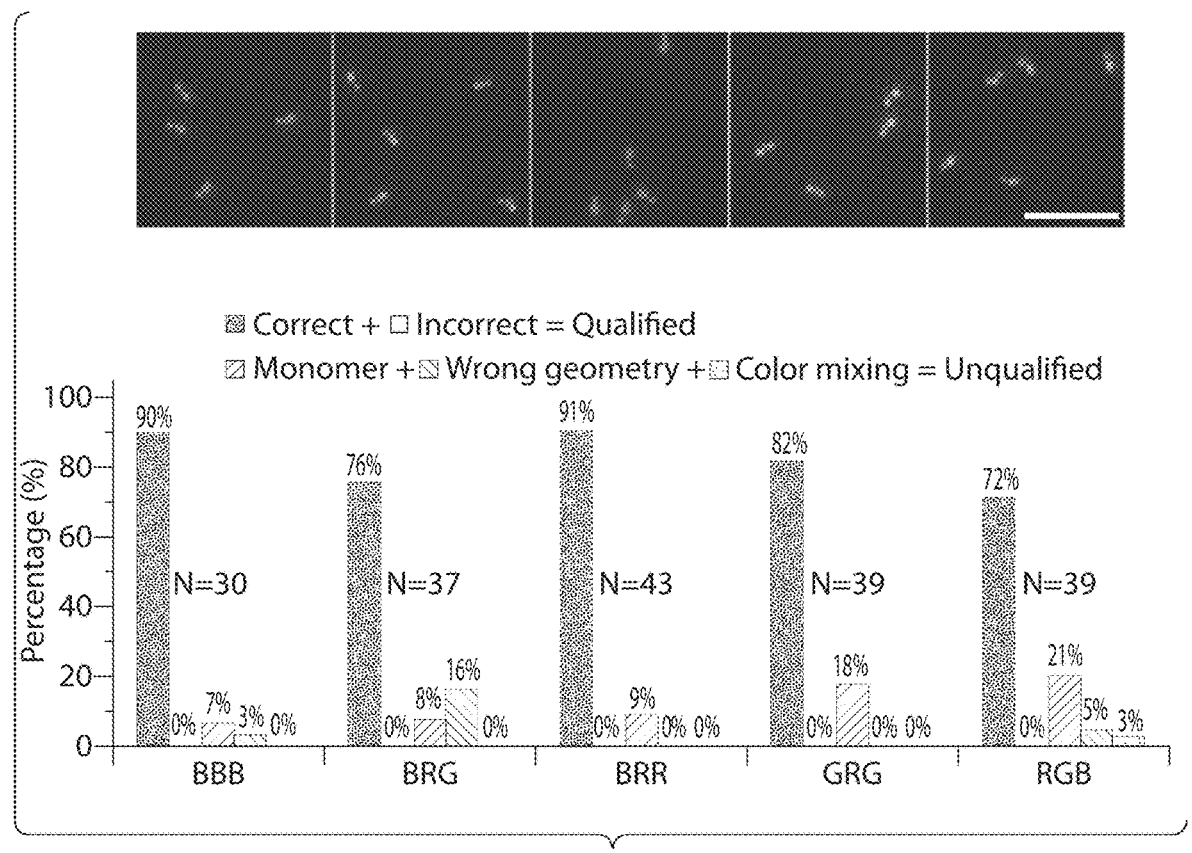
FIGS. 2A-2C. Single-labeled-zone fluorescent barcodes.

Five distinct barcodes from the 27 members in the barcode family were randomly chosen for quality control experiments. The barcodes were assembled and purified separately and imaged under the same experimental conditions. Two distinct features of the barcode were clearly visible from the TIRF images (FIG. 2A, top panel): first, each fluorescently labeled zone on a barcode was resolved as a single-color spot and each complete barcode consisted of three of such spots; Second, two of the neighboring spots were separated by a small gap while the other 7 two neighbors sat closely together. Therefore one can visually recognize and decode those geometrically encoded barcodes based on the color identity of the spots and their relative spatial positions, even without the aid of any specialized decoding software. Using a custom-written software that localizes the center of each spot on the BRG barcodes, we measured the average center-to-center distance between the neighboring spots to be 433±53 nm (mean±s.d., N=70; larger distance) and 264±52 nm (mean±s.d., N=70; smaller distance), confirming the correct formation of the barcodes. These experimentally measured distances were slightly smaller than the designed values (478 nm and 298 nm). We attribute this discrepancy to random thermal bending of the nanotubes (persistence length of ~1-2 μm), which has been observed previously by others[23,28] and confirmed by us (data not shown) using transmission electron microscopy (TEM). It is important to note that unlike some other geometrically encoded barcoding systems (e.g., NanoString nCounter[12]), there was no molecular combing step involved in the sample preparation. The separation between the fluorescent spots was exclusively created by the inherently rigid structure of the six-helix bundle nanotube. It is also notable that the spot intensities were not perfectly uniform across the whole image, which can be explained by factors such as the uneven illumination of the sample stage and differences in labeling efficiency. Nevertheless, the TIRF images proved that the barcodes were successfully assembled and can be resolved unambiguously. We then manually investigated TIRF images with an area of 50×50 μm$^2$ for the selected five barcodes (FIG. 2A, bottom panel). The objects found within the images were first sorted into qualified (i.e., three single-color spots arranged in a nearly linear and asymmetric fashion as designed) and unqualified (i.e., all other objects) barcodes. The qualified 8 barcodes were further categorized into correct and incorrect (false-positive) barcodes based on the fluorescent signatures of the composing spots to reflect whether the barcode was the expected type. The unqualified barcodes were further sorted into (1) monomer nanotubes (single spot or two "kissing" spots), (2) barcode with "wrong" geometry (i.e., extreme bending), and (3) barcode containing at least one spot with multiple colors. Our statistics revealed that more than 70% of the visible objects were qualified barcodes, which we further determined to be exclusively the expected type (i.e., zero false-positive out of 188 qualified barcodes observed). The unqualified barcodes arose likely from folding defects, sample damage during handling and overlapping nanotubes on the surface, which can be largely reduced by optimizing the sample preparation and imaging protocol.

Typically, a number of different barcode species coexist in one pool. Thus it is important to examine the robustness of our system by mixing different types of barcode together. In an initial test, we synthesized BRG and RGB barcodes separately, mixed them together at equal molar ratio and co-purified them via gel electrophoresis. The TIRF analysis of the purified mixture confirmed the 1:1 stoichiometry of the two barcodes and the overall assembly success rate (qualified barcode/all objects) of ~80%, suggesting that both barcodes maintained their integrity in the mixing and co-purification process. In addition, over 98% of the qualified barcodes fell into one of the two expected types (BRG and RGB). The 2% false-positive rate was due to an unexpected barcode namely BGB, which could be attributed to a rare occasion when the front monomer of the BRG barcode lay in proximity of the rear monomer of the RGB barcode. This can be eliminated using a more stringent purification condition to minimize the amount of leftover monomers.

Figure 2B:
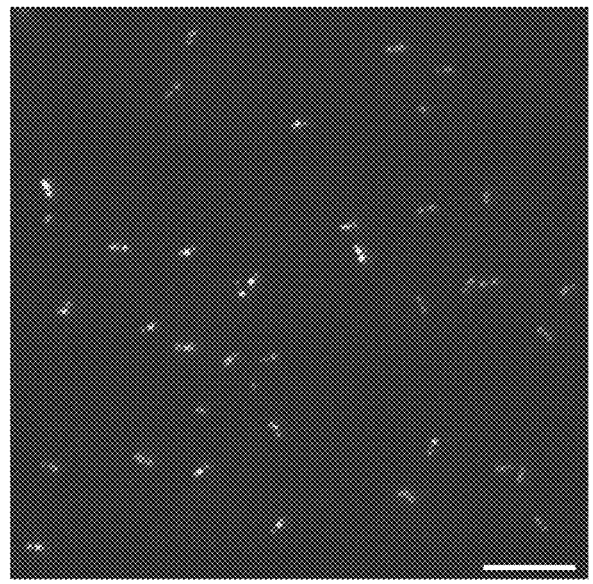
Figure 2C:
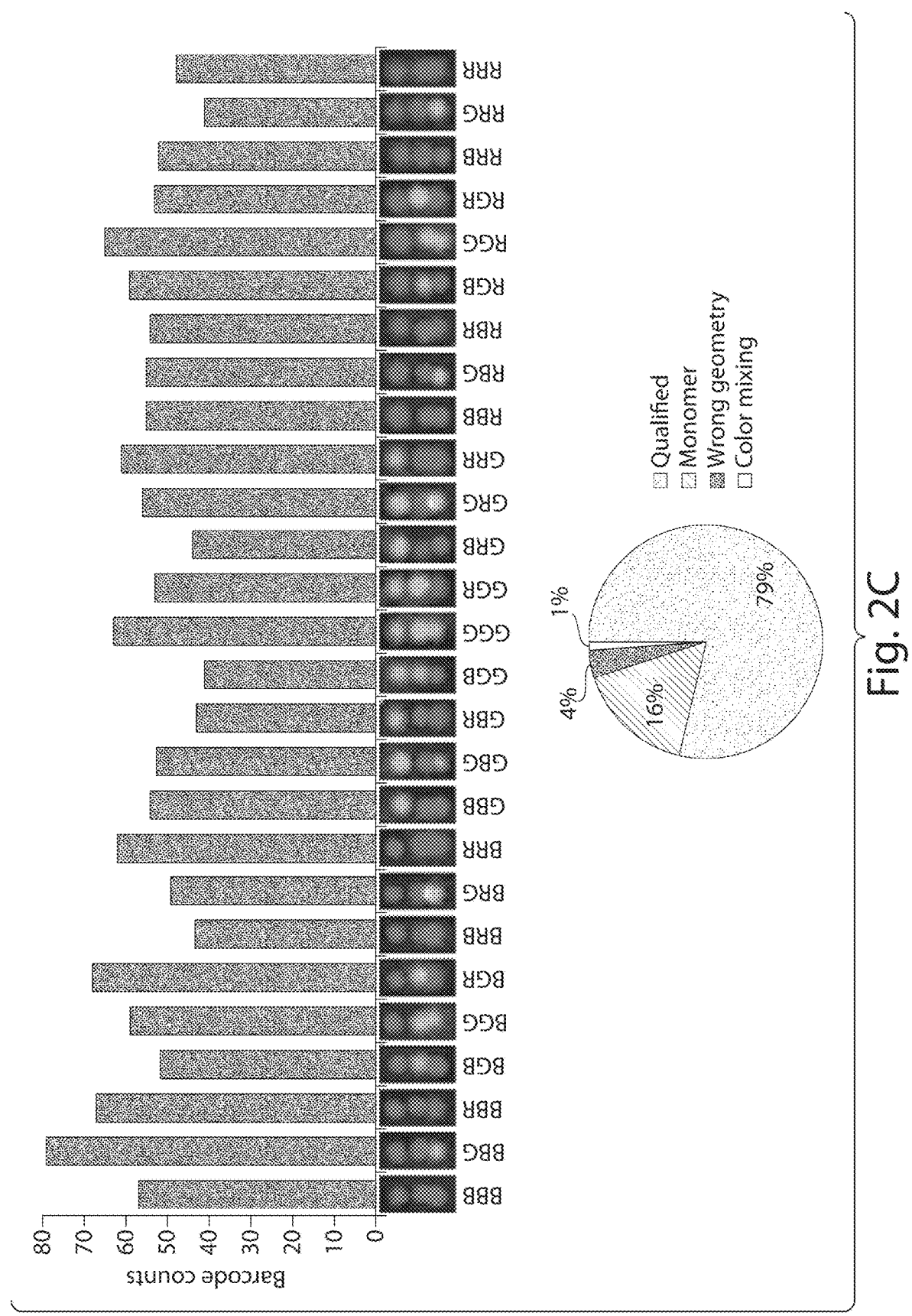

We next challenged the system by imaging a pool of all 27 members of the barcode family in which all species were mixed at equimolar amount. The TIRF images (FIG. 2B) showed that all types of barcodes were resolved. Statistics by sampling twenty-seven 50×50 μm$^2$ images (1,500 barcodes in total) revealed an average count of 55 per barcode type with a standard deviation of 9 (FIG. 2C), fitting well with the expected stoichiometry considering the pipetting and sampling error. The distribution of observed objects over the four categories (note that here correct vs. incorrect barcodes were not distinguishable as all 27 types were included) was consistent with the values measured from the single-type barcode samples. The above observations suggest that the sub-micrometer-long DNA nanotube represents a reliable platform to construct geometrically encoded barcodes with built-in structural rigidity.

Software could be used to recognize and decode the image of different types of DNA origami barcode probes automatically. Typically, such software has three basic steps: recognition, filtering and decoding. In the first step, the fluorescent spots are identified. For each fluorescent channel (blue, red or green), the software identifies fluorescent spots based on their intensity and size, then compares them to automatically determined thresholds using overall image intensity and pre-defined spot sizes. The fluorescent spots below those thresholds are removed along with general background noise. After processing all three channels, a barcode image is constructed by merging spots identified in three channels. An example of such a barcode image is provided in FIG. 3. In the second step, the distances (calculated from (x,y) coordinates of fluorescent spots) between each region of DNA origami barcode probes and the barcode bending angle (based on the center spot) are calculated. The software then filters DNA origami barcode probes and removes those with region distances that disagreed with the theoretical region distances or had a barcode bending angle smaller than a currently arbitrarily set threshold angle of 140 degrees. As an example, the BRG barcodes were filtered using three distance rules: (1) The distance between blue and green spot cannot be greater than 15 pixels (theoretical distance was 11 pixels); (2) The distance between red and blue spot cannot be greater than 9 pixels (theoretical distance was 6.8 pixels); and (3) The distance between red and green spot cannot be greater than 6 pixels (theoretical distance was 4.2 pixels). The BRG barcodes that had a bending angle (at the red spot) smaller than 140 degrees were removed. In the last step, after all barcodes are identified and filtered, the software uses different criteria (based on theoretical distance and color) to sort barcodes into specific types. Therefore, multiple types of DNA barcode probes can be decoded based on how they were originally designed. Besides the final constructed DNA barcode probe image, the software can output statistical information regarding the (x,y) coordinates of each DNA barcode probe fluorescent spot, distances between adjacent spots, barcode bending angle, and barcode types.

Figure 3A:
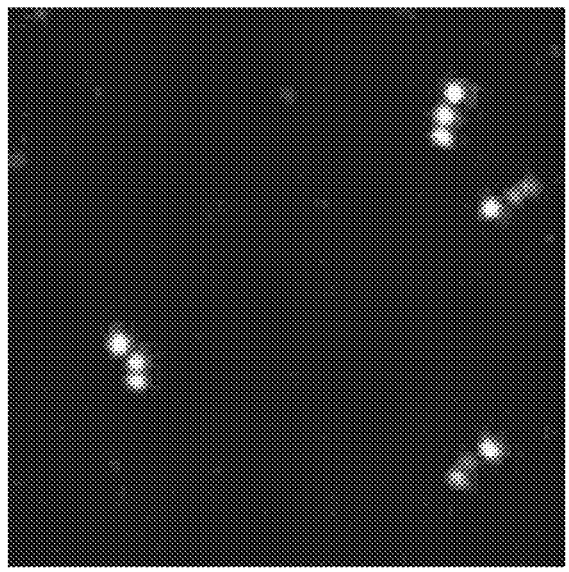
FIGS. 3A-3E. Representative TIRF and software reconstructed images of BRG and GRG nano-barcodes.
Figure 3B:
Figure 3C:
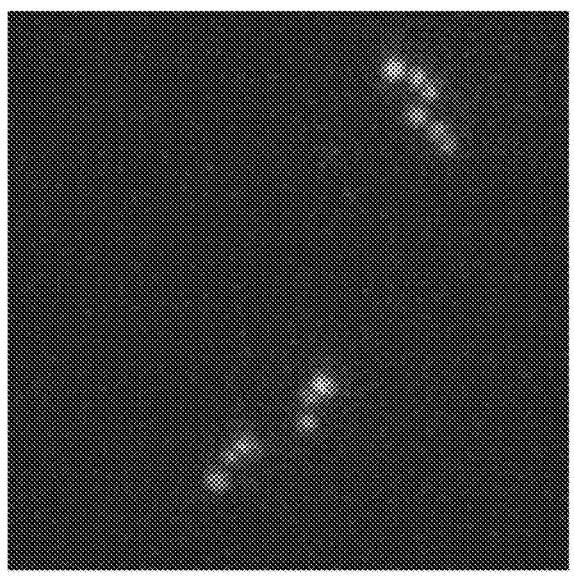
Figure 3D:
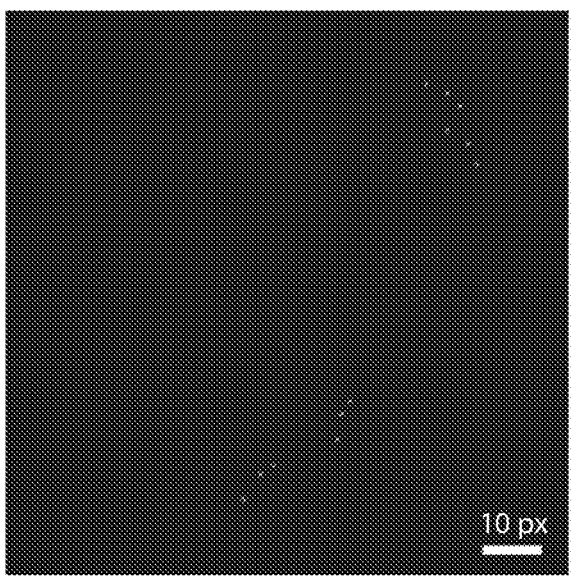
Figure 3E:
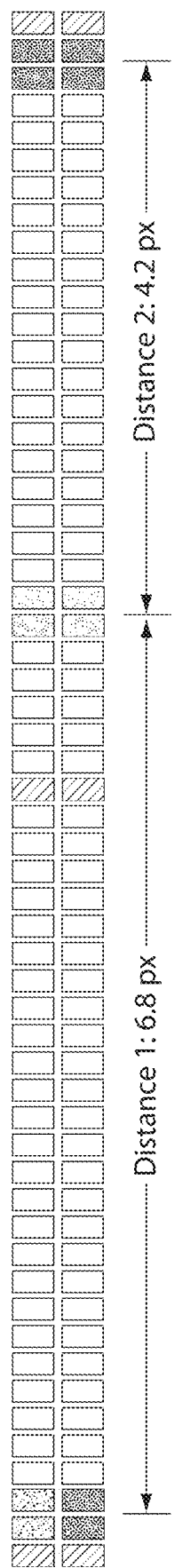

The software described above was used to detect BRG and GRG DNA origami barcode probes. As shown in FIG. 3, the BRG and GRG DNA origami barcode probes were clearly identified by the automated decoding software. The software used a number of filters to select the valid DNA origami barcode probes. As a result, 88% and 85% of BRG and GRG nano-barcodes were counted. The software generated statistical information on BRG and GRG barcodes (Table 2) that showed that the measured distances between each region on those DNA origami barcode probes were in good agreement with the theoretical region distances as designed (FIG. 3E).

TABLE 2

| Barcode type | Barcode identified | Barcode discarded | Barcode bending angle α (degree) | Distance 1 (pixel) | Distance 2 (pixel) |
|---|---|---|---|---|---|
| BRG | 70 | 9 | 165.11 ± 10.08 | 6.18 ± 0.76 | 3.77 ± 0.74 |
| GRG | 81 | 15 | 161.51 ± 11.73 | 6.12 ± 0.95 | 3.95 ± 0.98 |

Example 3: Detection of an Oligonucleotide Target Using a DNA Barcode Probe

A 42-nt DNA oligonucleotide target was detected using a DNA origami barcode probe. Two different purified barcodes Green, Red, Green (GRG) with the 21-nt oligonucleotide target capture moiety specific for a 42-nt oligonucleotide target (Target 1, see Table 3 for sequences) and Blue, Red, Green (BRG) without a target capture moiety, were mixed at 1:1 ratio and diluted to 20 pM in folding buffer. Biotin probe specific for Target 1 (0.2 μL of 100 nM) and Target 1 (0.4 μL of 10 nM) was added to 100 μL of the barcode mixture. In a separate test tube containing 100 μL of the barcode mixture, 0.2 μL of 100 nM biotin probe for Target 1 and 0.4 μL of 1× folding buffer was added as a negative control. The above samples were both incubated at 37° C. overnight before being run through separate channels of a micro-fluidic cell with a streptavidin coated glass cover-slip (Xenopore) substrate. Both channels were then washed with 40 μL of washing buffer (5 mM Tris-HCl pH 8.0, 500 mM NaCl) and imaged on a Leica TIRFM as described above. Ten images were taken in each channel at random locations and the total number of DNA origami barcode probes was counted manually.

TABLE 3

DNA sequences used in oligonucleotide target detection

| Name | Sequence (SEQ ID NO:) |
|---|---|
| Target oligo | 5'-GAATCGGTCACAGTACAACCGCGCCGTAGGGCTG-ATCAAAGC-3' (SEQ ID NO: 10) |
| Biotin probe | 5'-/Biotin/GCTTTGATCAGCCCTACGGCG-3' (SEQ ID NO: 11) |
| Capture probe | 5'-CGGTTGTACTGTGACCGATTC-3' (SEQ ID NO: 12) |

Figure 4A:
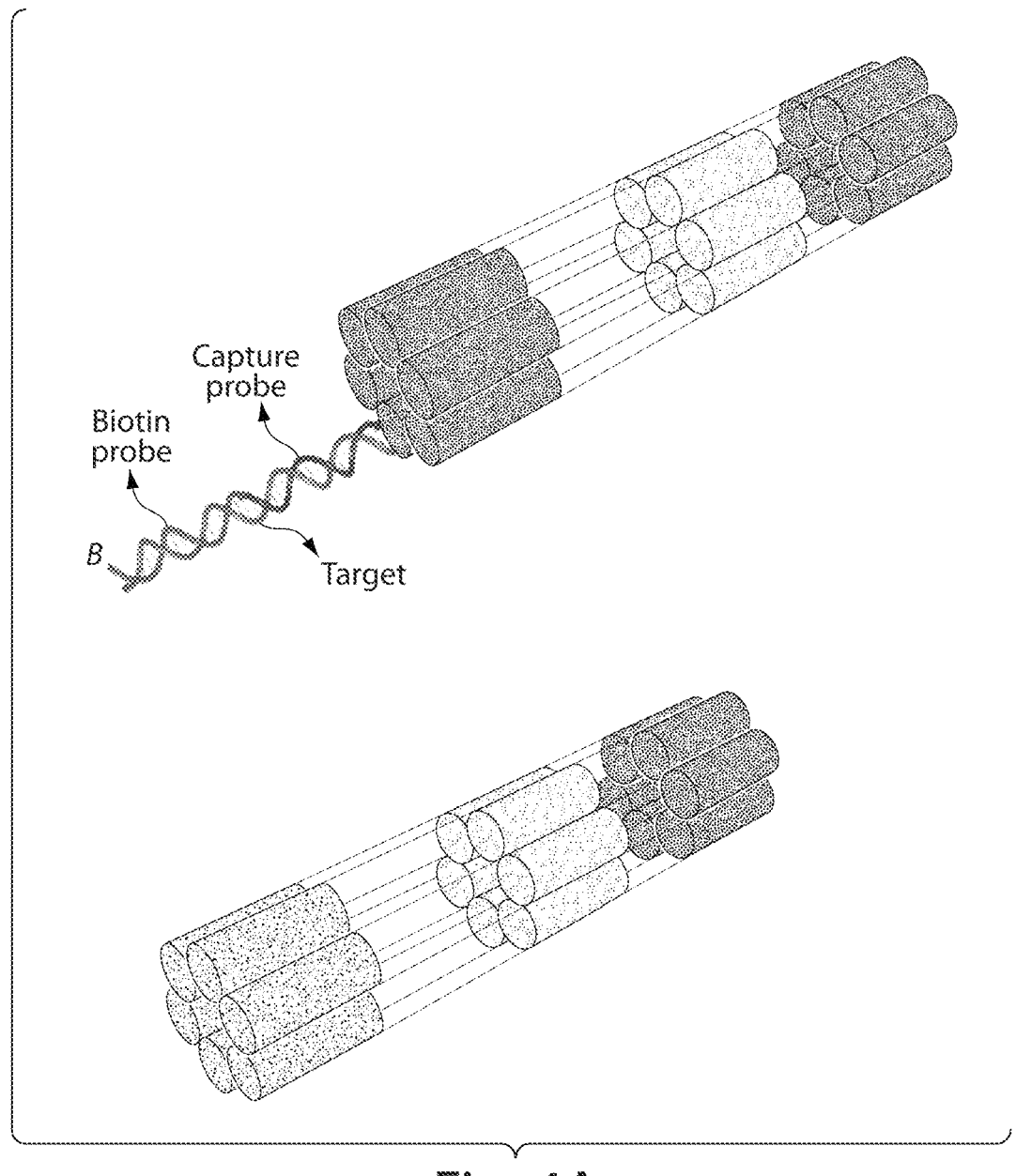
FIGS. 4A-4C. Schematic illustration and result of a 21-mer oligonucleotide detection using nano-barcodes.
Figure 4B:
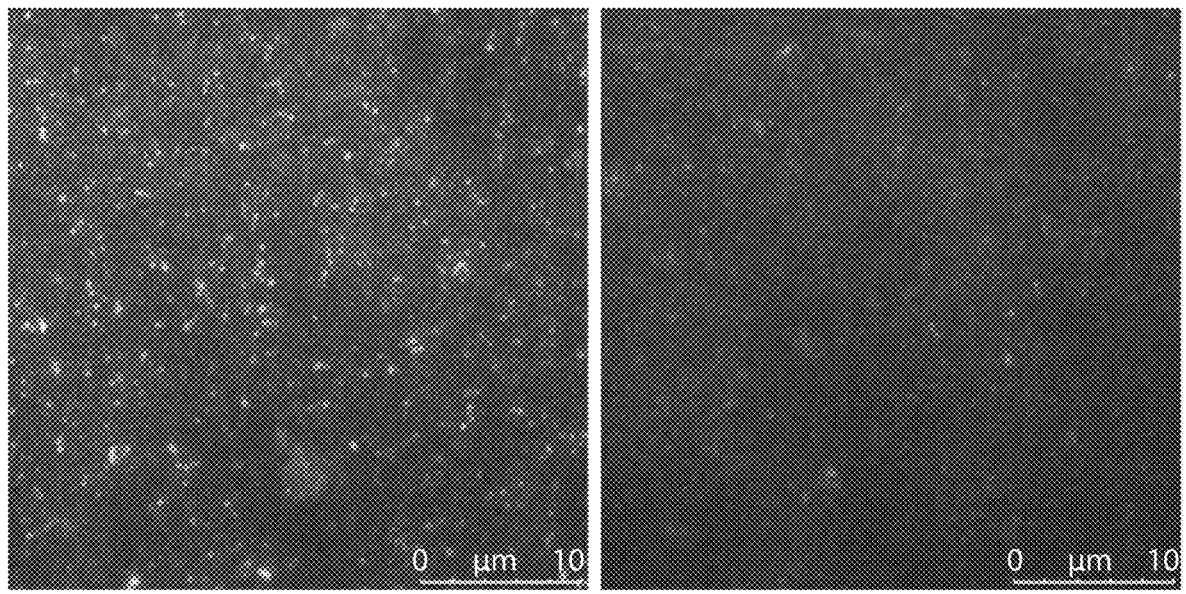
Figure 4C:
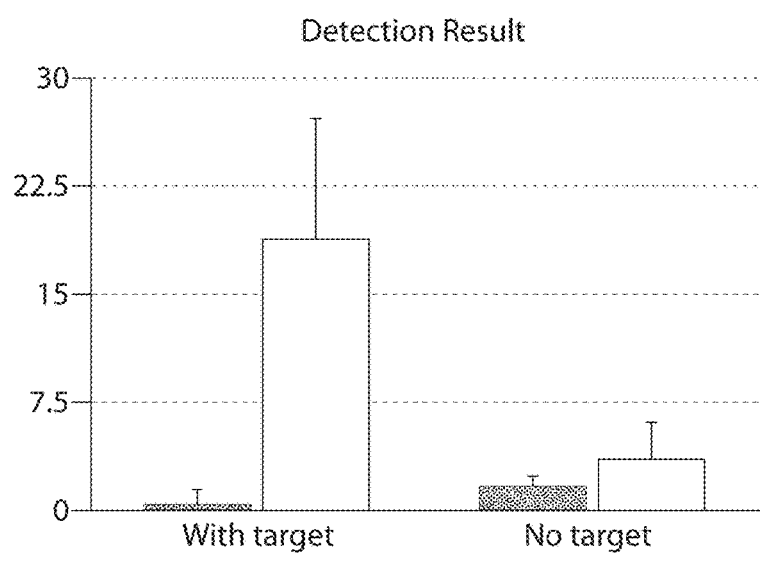

In the presence of the target oligonucleotide, the biotin probe hybridized to one 21 nt sequence of the target oligonucleotide, while the GRG barcode hybridized to a second 21 nt sequence of the target oligonucleotide. The BRG probe, however, lacking a target capture moiety specific for the target oligonucleotide does not hybridize to the target and therefore does not become bound by the biotin probe. (FIG. 4A). As a consequence, when the detection reaction mixture was run through the streptavidin-coated glass surface, the GRG barcode binds to the surface, while BRG barcode is washed away. TIRF images and statistical analysis supported the specificity of the detection (FIGS. 4B and C). In the presence of 40 pM oligonucleotide target, there were ~20 times more GRG barcodes than BRG barcodes bound to the surface. In the absence of the target, both barcodes did not show significant surface binding.

Example 4: Dual-Labeled Barcode Probes

In order to enhance multiplexing capability even further, the sequence of six staple extensions per zone was changed so that instead of using twelve identical fluorescent oligonucleotides for labeling, a combination of up to two fluorophores was used to create more unique fluorescence signatures (pseudo-colors) for each zone. Six pseudo-colors (B, R, G, BG, BR, and GR) were generated by this "dual-labeling" strategy using three spectrally differentiable fluorophores. Consequently, the total number of distinct barcodes was raised from 27 to $6^3$=216, which represented an order of magnitude increase in the multiplexing capability.

Figure 5A:
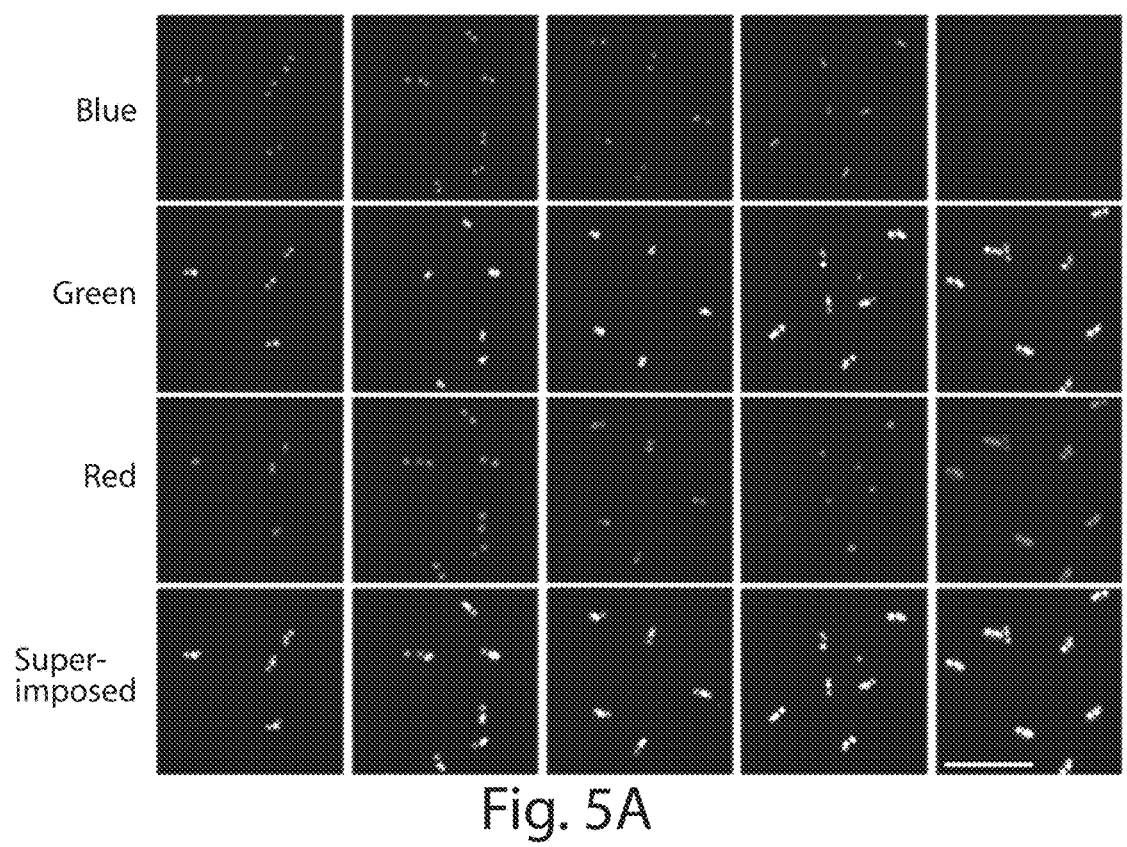
Figure 5B:
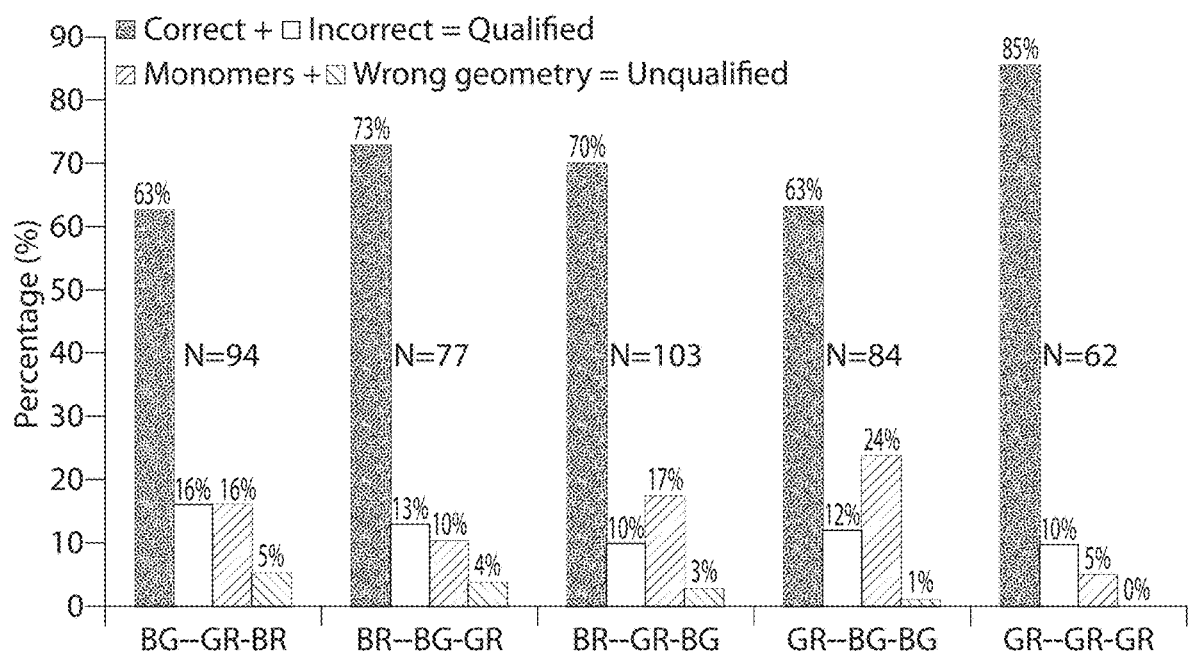

Similar to the single-labeled-zone barcode family, 5 members from the dual-labeled-zone barcode family were chosen for quality control purpose. The barcodes can be visually decoded either solely from the superimposed image or by examining all different channels simultaneously. For example, as shown in the first column of FIG. 5A, the barcode "BG--GR-BR" ("--" and "-" denotes larger and smaller inter-zone distance in the barcode, respectively) exhibited two spots each in the blue, green and red channels but with descending gaps between them, matching its design. In the superimposed image, the barcodes were seen as Cyan--Yellow-Pink, an expected consequence of color mixing caused by the dual-labeling strategy. In a similar fashion, we further verified the correct formation of the other four selected barcodes (FIG. 5A). Although the final pseudo-color from the dual-labeled zones was not always uniform (e.g., some yellow spots were green-tinted while the others were red-tinted) due to the inconsistent labeling efficiency and minor sample displacement during imaging, the fluorescence signature of any given spot could be identified by checking the raw images acquired from the three imaging channels. We manually analyzed two 50×50 µm$^2$ images of each dual-labeled-zone barcode and plotted the statistical data in FIG. 5B. Here, objects were sorted into qualified barcodes and unqualified barcodes based on their geometry and the qualified ones were further categorized as correct and incorrect. 75-95% of the objects were qualified barcodes, among which 80-90% were the correct type (percentage varies depending on the exact type of barcode). Compared to the single-labeled-zone barcode family, the percentage of qualified barcodes remained the same, while the false positive rate increased significantly from zero to 10-20%. This observed increased false positive rate is consistent with the expected decreased robustness of the dual-labeling strategy (as compared to single-labeling). In one design, a dual-labeled zone carried 6 staple extensions for each fluorophore species, only half as many as in a single-labeled zone.

As a result, the dual-labeled-zone barcode consisted of dimmer spots that were more susceptible to damages such as photo bleaching. In this sense, a single-labeled-zone barcode can be thought of as a redundantly encoded dual-labeled-zone barcode. For instance, a single-labeled-zone barcode can still be recognized as the correct type when six fluorophores were missing from each zone, a scenario in which the dual-labeled-zone barcode could be disqualified or categorized as incorrect. In the latter case, it will increase the false positive rate. In principle, the false positive rate can be decreased by increasing the copy number of each fluorophore species in a dual-labeled zone. The five barcodes we examined have each of their zones labeled with two distinct fluorophore species, making them likely among the most error-prone members of the dual-labeled-zone barcode family. Therefore, we would expect a smaller false-positive rate on average from the whole family.

Figure 5C:
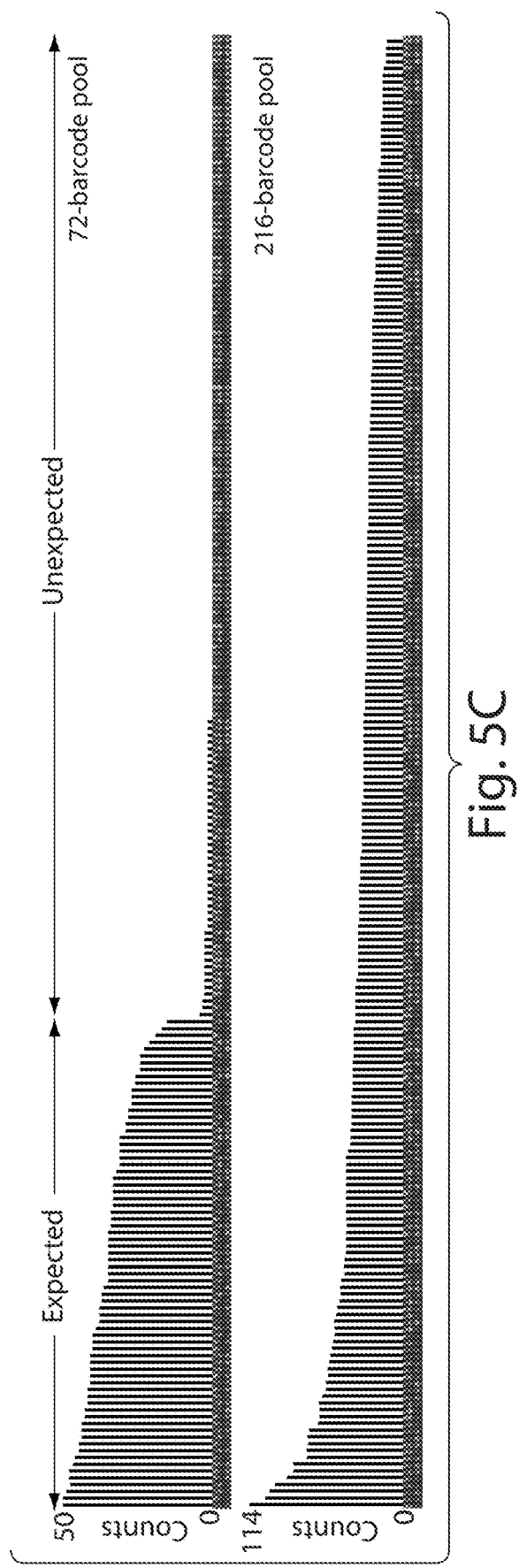

We further tested the dual-labeled-zone barcoding system by imaging a mixture containing 72 barcode species that were individually assembled and co-purified. Custom MATLAB scripts were used to assist the decoding process in two steps. In step one, a three-channel (red, green, blue) TIRF image containing barcodes was pre-processed to remove background and thresholded so that only pixels containing qualified barcodes remained. The resulting three-channel binary image was merged to generate a single-channel binary image. Next, the software identified the location and orientation of geometrically legitimate barcodes based on their shape in the binary image. In step two, for each barcode located in step one, the corresponding region of the three-channel image was compared against a library of all possible reference barcodes. The observed barcode was assigned the identity of the reference barcode with the highest correlation. The fully automated decoding process (unsupervised mode) ended after the above two steps. In an optional supervised mode, the software presented the user with the observed barcode and its most likely identity for approval. Comparison between supervised and unsupervised decoding results confirmed >80% agreement between the computer and the user. The computer-aided (supervised mode) analysis of thirty-six 64×64 µm$^2$ three-channel images registered ~2,600 qualified barcodes that belonged to 116 different species (FIG. 5C, top panel). The expected 72 species constituted ~98% of the total barcode population with an average barcode count of 36 per species and a standard deviation of 8. In contrast, the unexpected species averaged only ~1.4 barcodes per species (maximum 4 counts).

Figure 5D:
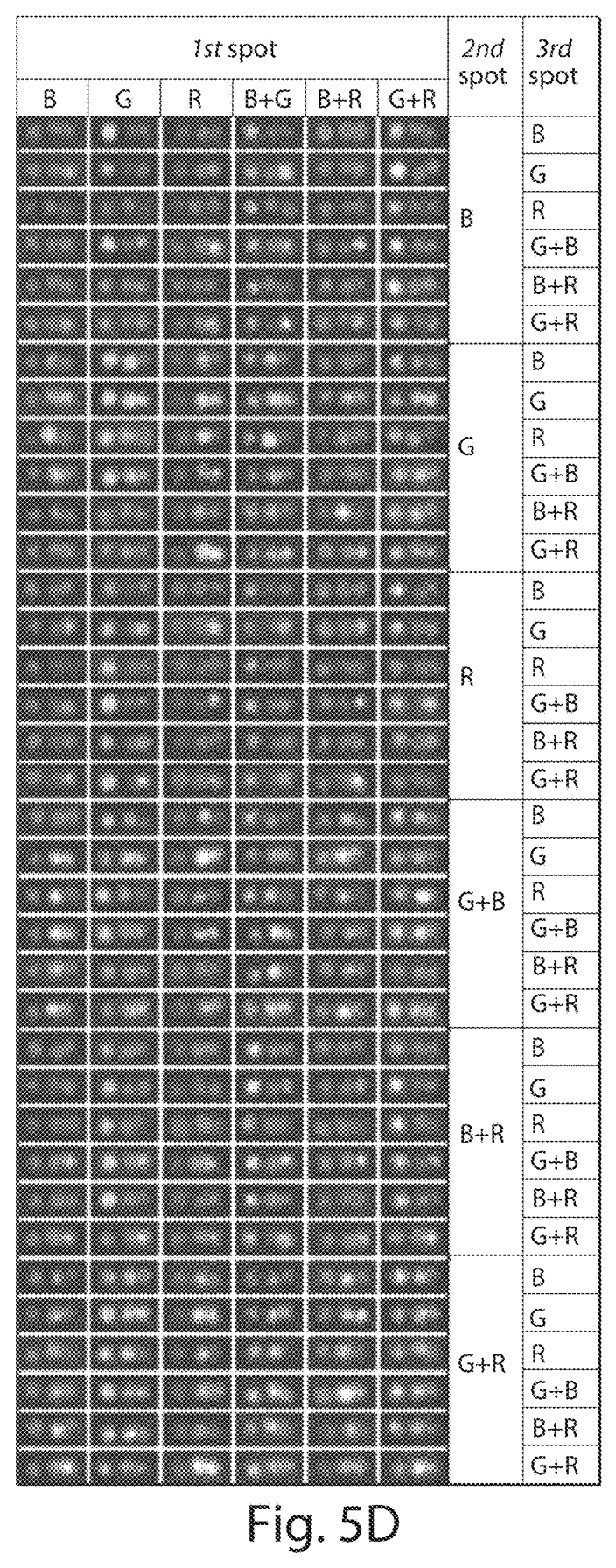

Finally, we analyzed a mixture containing all the 216 members of the dual-labeled-zone barcode. Sixty 64×64 µm$^2$ images of this mixture were processed by the decoding software in the unsupervised mode. The fully automated analysis registered ~34 barcode counts per species (~7,200 barcodes total) with a standard deviation of 17 (FIG. 5C, bottom panel). The relatively large standard deviation could be attributed to the decoding error in the fully automated data analysis. Our study demonstrated that 216 barcode species were successfully constructed and resolved (FIG. 5D).

Example 5: Super-Resolution Barcode Probes

Barcodes with higher spatial information density were also generated using geometrically encoded super-resolution barcodes with fluorescent features spaced by ~100-nm.

As a feasibility demonstration of the latter approach, we applied DNA-PAINT[31], a recently developed super-resolution fluorescence technique, to image the barcodes. Over the last years, several techniques have been developed that allow imaging beyond the diffraction limit using far-field fluorescence microscopy[40-44]. In most super-resolution implementations, fluorophores are switched between fluorescence ON- and OFF-states, so that individual molecules can be localized consecutively. In methods relying on targeted readout schemes such as in Stimulated Emission Depletion Microscopy[45] (STED) or other Reversible Saturable Optical Fluorescence Transitions[40] (RESOLFT) techniques, fluorescence emission is actively confined to an area below the diffraction limit. Switching of fluorescent molecules can also be carried out stochastically such as in (direct) Stochastic Optical Reconstruction Microscopy[46,47] (STORM, dSTORM), Photoactivated Localization Microscopy[48] (PALM) and Blink Microscopy[49] (BM) where most fluorescent molecules are "prepared" in a dark state and only stochastically switched on to emit fluorescence. In Point Accumulation for Imaging in Nanoscale Topography[50] (PAINT), fluorescence switching is obtained by targeting a surface with fluorescent molecules. In all stochastic approaches, fluorescence from single molecules is localized[51,52] in a diffraction-limited area to yield super-resolved images. DNA-PAINT uses transient binding of fluorescently labeled oligonucleotides (imager strands) to complementary "docking" strands on DNA nanostructures to obtain switching between a fluorescence ON- and OFF-state, which is necessary for localization-based super-resolution microscopy (cf. FIG. 6A). By adjusting the length of the imager/docking strand duplex and the concentration of imager strands in solution, fluorescence ON- and OFF-times can be tuned independently.

Figure 6A:
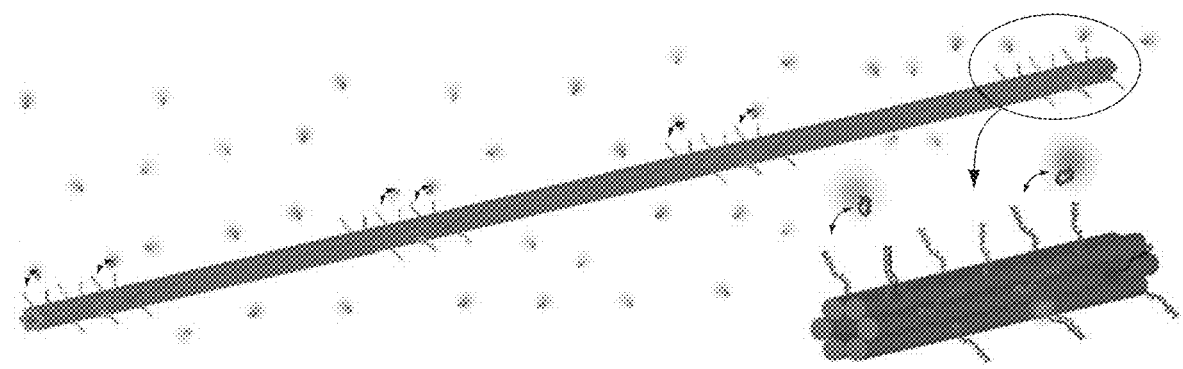
FIGS. 6A-6C. Super-resolution fluorescent barcodes.
Figure 6B:
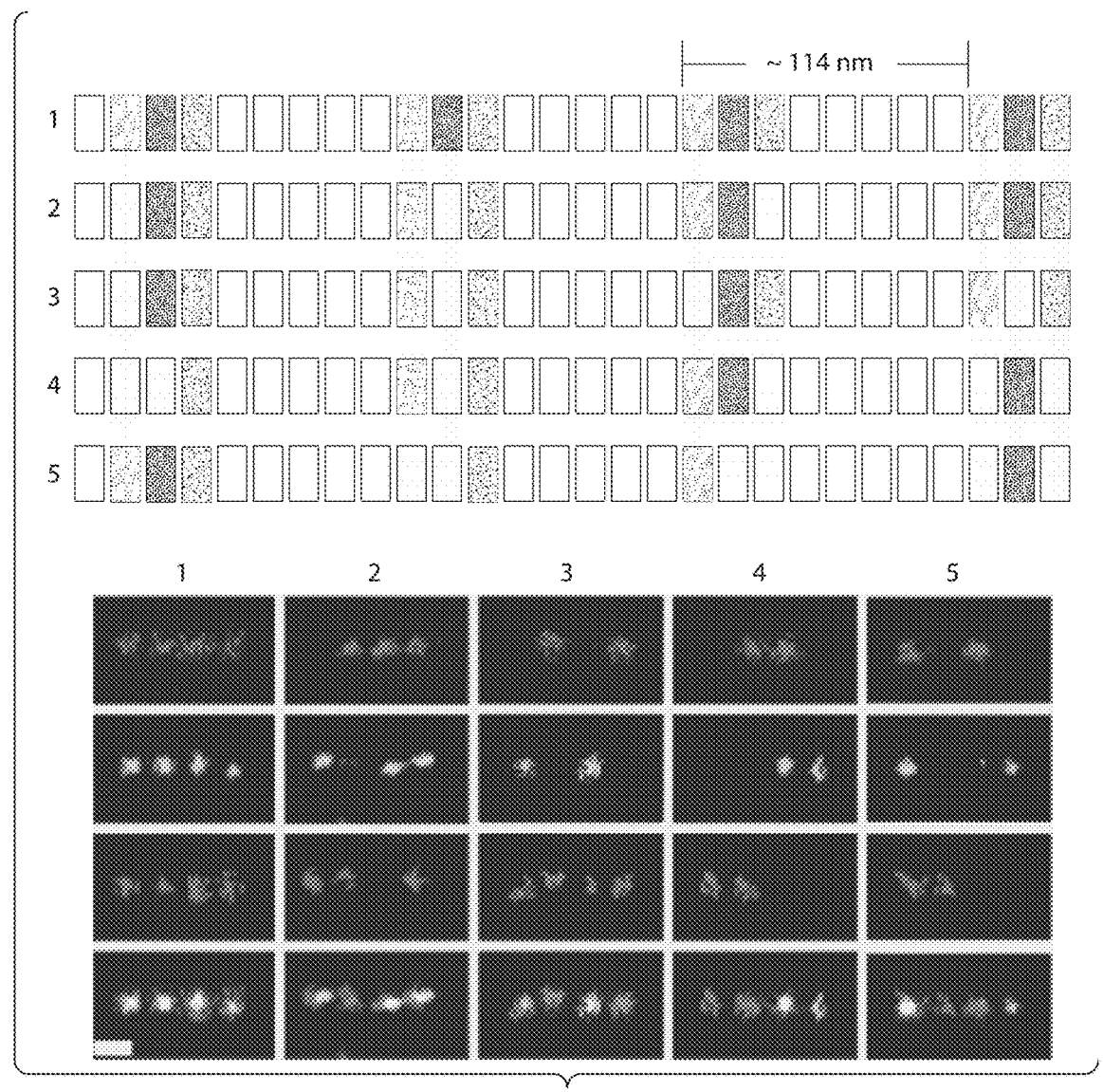
Figure 6C:
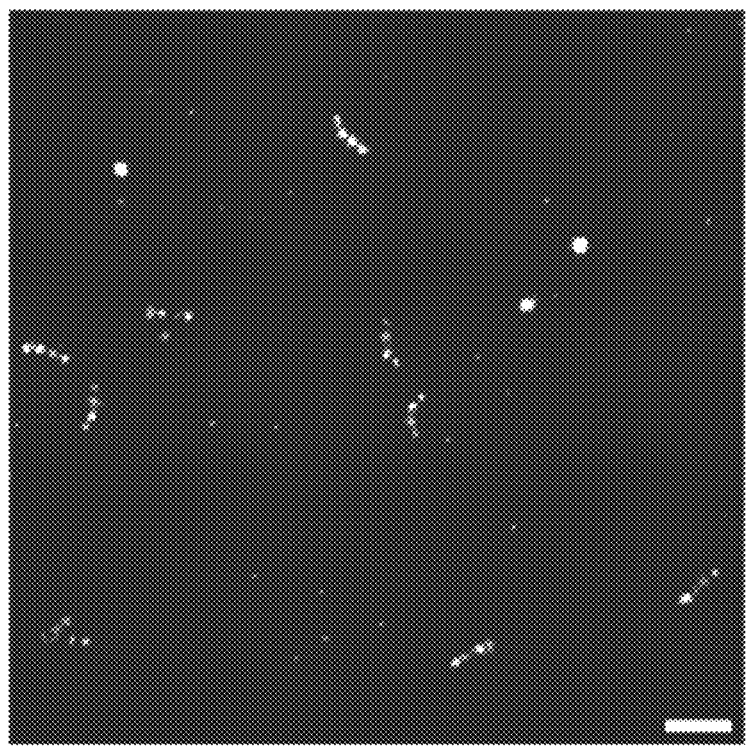

For this study, we extended the DNA-PAINT technique to three-color imaging using orthogonal imager strand sequences coupled to three spectrally distinct dyes (Atto488 for blue, Cy3b for green and Atto655 for red excitation). To demonstrate the feasibility of the three-color super-resolution barcode system, we designed a DNA nanotube monomer with 4 binding zones in a symmetric arrangement. The neighboring zones were separated by ~114 nm (i.e., well below the diffraction limit). Each binding zone consists of 18 staple strands, which can be extended to display three groups of orthogonal sequences (six per group) for the red, green or blue imager strands to bind. As a proof-of-principle experiment, we designed five different barcodes (FIG. 6A and top panel of B). The bottom panel of FIG. 6B shows the super-resolution reconstruction of the five barcodes for each channel separately as well as an overlay of all channels. FIG. 6C shows a larger area containing all five barcodes. The unique pattern of the barcodes in all three channels can be resolved. Some barcodes moved during the sequential imaging of all three color channels, but were still resolvable. Imaging could be improved by alternating excitation and faster image acquisition to prevent this effect. The transient, repetitive binding of imager strands to docking sequences on the nanotube not only creates the necessary "blinking" behavior for localization but also makes the imaging protocol more robust, as DNA-PAINT is not prone to photobleaching or incorrectly labeled strands. With the microscope setup we used, DNA-PAINT provides a resolution of ~46 nm (FWHM of a Gaussian fit to the reconstructed PSF) in the red, ~25 nm in the green and ~29 nm in the blue channel. The lower resolution in the red imaging channel is a result from weaker laser excitation power. When using a higher power TIRF system, a resolution of 24 nm, similar to the green and blue channel can be obtained. The obtainable resolution and imaging specificity suggests that 6 positions on one nanotube monomer could be robustly resolved while keeping the geometrical asymmetry of the barcode, which would lead to $6^7=279,936$ possible different barcodes. Furthermore the modularity of the nanotube design enables the customized reengineering of barcodes with inter-zone distances tailored to the resolving power of the used microscope, thus making it applicable for a wide range of microscope setups.

Example 6: In Situ Labeling

Figure 7A:
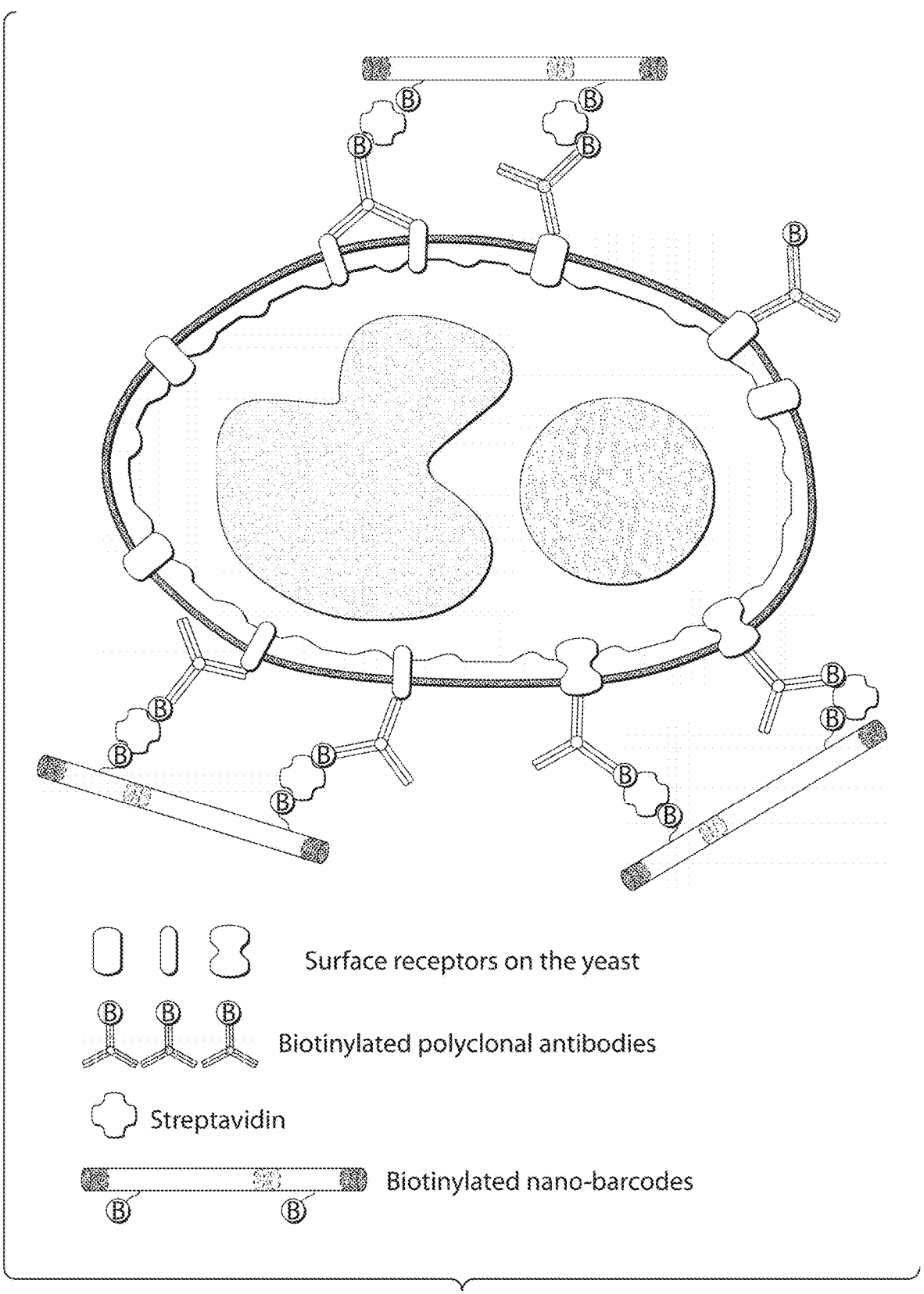
FIGS. 7A-7B. Tagging yeast cells with the GRG barcodes as in situ imaging probes.
Figure 7B:
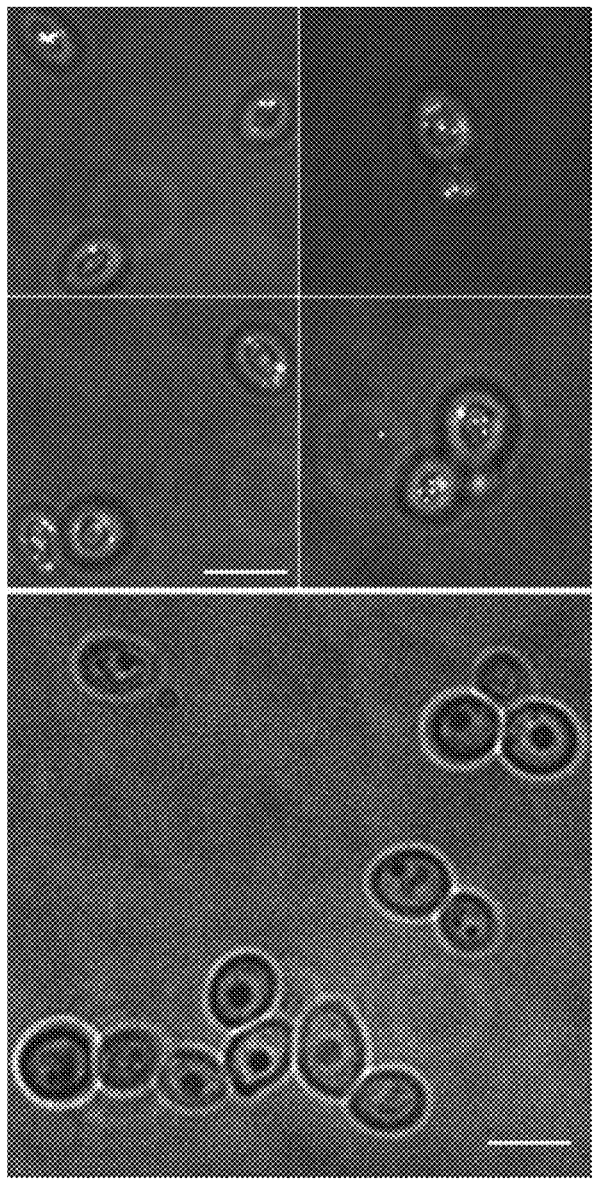

In a proof-of-principle experiment, the GRG barcode was used to tag wild-type *Candida albicans* yeast. The yeast cells were first mixed with a biotinylated polyclonal antibody specific to *C. albicans*, then coated with a layer of streptavidin, and finally incubated with biotinylated GRG barcodes (FIG. 7A). TIRF microscopy revealed the barcodes attached to the bottom surface of the yeast cells (FIG. 7B, top panel). While some of the nanotubes landed awkwardly on the uneven cell walls of the yeast cells, a number of GRG barcodes can be clearly visualized. In contrast, no barcode tagging was observed when non-biotinylated antibodies or barcodes were used to treat the yeasts (FIG. 7B, bottom panel), suggesting that little to no non-specific interaction existed between the barcode and the cell surface.

Example 7: Non-Linear Labeled Nanostructures

Figure 8A:
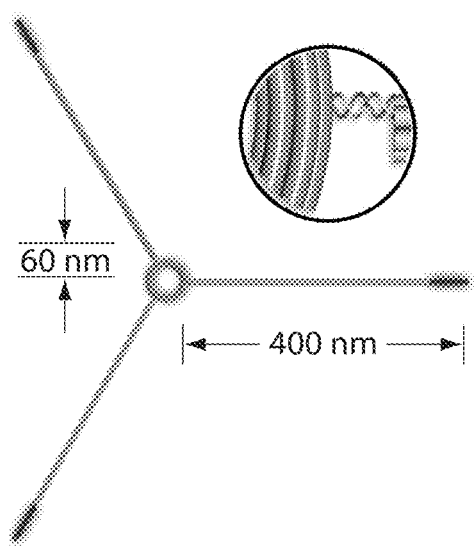
FIGS. 8A-8B. Fluorescent barcode with non-linear geometry.
Figure 8B:
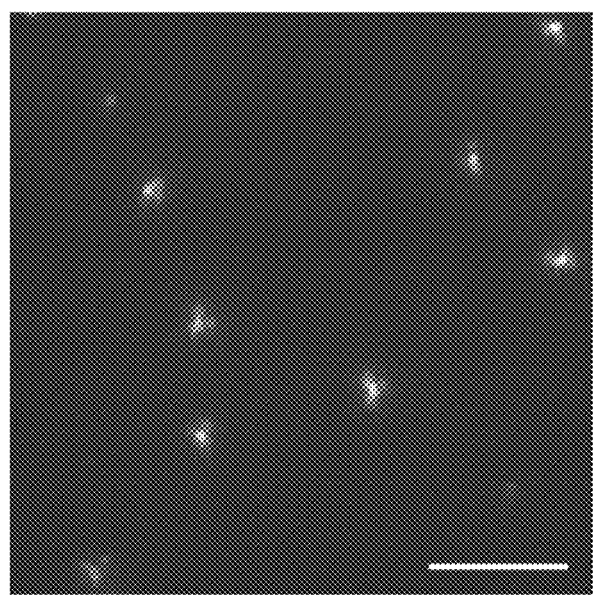

DNA nanostructures with non-linear geometry could be assembled to generate more sophisticated barcodes. FIG. 8 shows an example where three ~400 nm DNA tubes were linked to the outer edge of a ~60 nm DNA ring through hybridization between the staple extensions (FIG. 8A, inset). Fluorescently labeling the ring and the far end of the nanotubes generated a three-point-star-like structure clearly resolvable under fluorescence microscopy. TIRF microscopy and TEM studies (FIG. 8B) revealed that about 50% of successfully folded barcodes featured three nanotubes surrounding the ring with roughly 120° angle between each other as designed, while many other barcodes had significantly biased angles between neighboring nanotubes due to the semi-flexible double-stranded DNA linker between the ring and the nanotubes. It is conceivable that using similar design to connect three identical "satellite" linear barcodes to a central hub (here the three satellite barcodes may share the hub as a common fluorescently labeled zone), one can construct barcodes with triplicated encoding redundancy that feature outstanding reliability. In addition, more rigid linkers between the ring and the protrusions (e.g., multi-helix DNA with strand crossovers) could be employed to enforce better-defined barcode geometry.

REFERENCES

1 Han, M., Gao, X., Su, J. Z. & Nie, S. Quantum-dot-tagged microbeads for multiplexed optical coding of biomolecules. Nature biotechnology 19, 631-635, doi:10.1038/90228 (2001).
2 Xu, H. et al. Multiplexed SNP genotyping using the Qbead system: a quantum dot-encoded microsphere-based assay. Nucleic Acids Research 31, e43 (2003). 3 Li, Y., Cu, Y. T. H. & Luo, D. Multiplexed detection of pathogen DNA with
3 DNA-based fluorescence nanobarcodes. Nature biotechnology 23, 885-889, doi:10.1038/nbt1106 (2005).
4 Livet, J. et al. Transgenic strategies for combinatorial expression of fluorescent proteins in the nervous system. Nature 450, 56-62, doi:10.1038/nature06293 (2007).
5 Fournier Bidoz, S. et al. Facile and Rapid One-Step Mass Preparation of Quantum-Dot Barcodes. Angewandte Chemie International Edition 47, 5577-5581, doi:10.1002/anie.200800409 (2008).
6 Lin, C., Liu, Y. & Yan, H. Self-assembled combinatorial encoding nanoarrays for multiplexed biosensing. Nano letters 7, 507-512, doi:10.1021/nl062998n (2007).
7 Marcon, L. et al. 'On-the-fly' optical encoding of combinatorial peptide libraries for profiling of protease specificity. Molecular bioSystems 6, 225-233, doi:10.1039/b909087h (2010).
8 Nicewarner-Pena, S. R. Submicrometer Metallic Barcodes. Science 294, 137-141, doi:10.1126/science.294.5540.137 (2001).
9 Gudiksen, M. S., Lauhon, L. J., Wang, J., Smith, D. C. & Lieber, C. M. Growth of nanowire superlattice structures for nanoscale photonics and electronics. Nature 415, 617-620, doi:10.1038/415617a (2002).
10 Braeckmans, K. et al. Encoding microcarriers by spatial selective photobleaching. Nature materials 2, 169-173, doi:10.1038/nmat828 (2003).
11 Dejneka, M. J. et al. Rare earth-doped glass microbarcodes. Proceedings of the National Academy of Sciences of the U.S. of America 100, 389-393, doi:10.1073/pnas.0236044100 (2003).
12 Geiss, G. K. et al. Direct multiplexed measurement of gene expression with color-coded probe pairs. Nature biotechnology 26, 317-325, doi:10.1038/nbt1385 (2008).
13 Pregibon, D. C., Toner, M. & Doyle, P. S. Multifunctional encoded particles for high-throughput biomolecule analysis. Science 315, 1393-1396, doi:10.1126/science.1134929 (2007).
14 Xiao, M. et al. Direct determination of haplotypes from single DNA molecules. Nature methods 6, 199-201, doi:10.1038/nmeth.1301 (2009).

15 Li, X. et al. Controlled fabrication of fluorescent barcode nanorods. ACS nano 4, 4350-4360, doi:10.1021/nn9017137 (2010).
16 Levsky, J. M., Shenoy, S. M., Pezo, R. C. & Singer, R. H. Single-cell gene expression profiling. Science 297, 836-840, doi:10.1126/science.1072241 (2002).
17 Seeman, N. C. Nucleic acid junctions and lattices. Journal of Theoretical Biology 99, 237-247 (1982).
18 Aldaye, F. A., Palmer, A. L. & Sleiman, H. F. Assembling materials with DNA as the guide. Science 321, 1795-1799, doi:10.1126/science.1154533 (2008).
19 Lin, C., Liu, Y. & Yan, H. Designer DNA nanoarchitectures. Biochemistry 48, 1663-1674, doi:10.1021/bi802324w (2009).
20 Nangreave, J., Han, D., Liu, Y. & Yan, H. DNA origami: a history and current perspective. Current opinion in chemical biology 14, 608-615, doi:10.1016/j.cbpa.2010.06.182 (2010).
21 Shih, W. M. & Lin, C. Knitting complex weaves with DNA origami. Current opinion in structural biology 20, 276-282, doi:10.1016/j.sbi.2010.03.009 (2010).
22 Tørring, T., Voigt, N. V., Nangreave, J., Yan, H. & Gothelf, K. V. DNA origami: a quantum leap for self-assembly of complex structures. Chemical Society Reviews, doi:10.1039/c1cs15057j (2011).
23 Rothemund, P. W. K. Folding DNA to create nanoscale shapes and patterns. Nature 440, 297-302, doi:10.1038/nature04586 (2006).
24 Douglas, S. M. et al. Self-assembly of DNA into nanoscale three-dimensional shapes. Nature 459, 414-418, doi:10.1038/nature08016 (2009).
25 Dietz, H., Douglas, S. M. & Shih, W. M. Folding DNA into twisted and curved nanoscale shapes. Science 325, 725-730, doi:10.1126/science.1174251 (2009).
26 Ke, Y. et al. Multilayer DNA origami packed on a square lattice. Journal of the American Chemical Society 131, 15903-15908, doi:10.1021/ja906381y (2009).
27 Andersen, E. S. et al. Self-assembly of a nanoscale DNA box with a controllable lid. Nature 459, 73-76, doi:10.1038/nature07971 (2009).
28 Han, D., Pal, S., Liu, Y. & Yan, H. Folding and cutting DNA into reconfigurable topological nanostructures. Nature nanotechnology 5, 712-717, doi:10.1038/nnano.2010.193 (2010).
29 Liedl, T., Högberg, B., Tytell, J., Ingber, D. E. & Shih, W. M. Self-assembly of three-dimensional prestressed tensegrity structures from DNA. Nature nanotechnology 5, 520-524, doi:10.1038/nnano.2010.107 (2010).
30 Han, D. et al. DNA Origami with Complex Curvatures in Three-Dimensional Space. Science 332, 342-346, doi:10.1126/science.1202998 (2011).
31 Jungmann, R. et al. Single-Molecule Kinetics and Super-Resolution Microscopy by Fluorescence Imaging of Transient Binding on DNA Origami. Nano letters, doi:10.1021/nl103427w (2010).
32 Steinhauer, C., Jungmann, R., Sobey, T. L., Simmel, F. C. & Tinnefeld, P. DNA origami as a nanoscopic ruler for super-resolution microscopy. Angewandte Chemie (International ed in English) 48, 8870-8873, doi:10.1002/anie.200903308 (2009).
33 Lund, K. et al. Molecular robots guided by prescriptive landscapes. Nature 465, 206-210, doi:10.1038/nature09012 (2010).
34 Pal, S., Deng, Z., Ding, B., Yan, H. & Liu, Y. DNA-origami-directed self-assembly of discrete silver-nanoparticle architectures. Angewandte Chemie (International ed in English) 49, 2700-2704, doi:10.1002/anie.201000330 (2010).
35 Bui, H. et al. Programmable Periodicity of Quantum Dot Arrays with DNA Origami Nanotubes. Nano letters 10, 3367-3372, doi:10.1021/nl101079u (2010).
36 Liu, W., Zhong, H., Wang, R. & Seeman, N. C. Crystalline two-dimensional DNA-origami arrays. Angewandte Chemie (International ed in English) 50, 264-267, doi:10.1002/anie.201005911 (2011).
37 Woo, S. & Rothemund, P. W. K. Programmable molecular recognition based on the geometry of DNA nanostructures. Nature Chemistry 3, 620-627, doi:10.1038/nchem.1070 (2011).
38 Douglas, S. M., Chou, J. J. & Shih, W. M. DNA-nanotube-induced alignment of membrane proteins for NMR structure determination. Proceedings of the National Academy of Sciences of the U.S. of America 104, 6644-6648, doi:10.1073/pnas.0700930104 (2007).
39 Aitken, C. E., Marshall, R. A. & Puglisi, J. D. An oxygen scavenging system for improvement of dye stability in single-molecule fluorescence experiments. Biophysical journal 94, 1826-1835, doi:10.1529/biophysj.107.117689 (2008).
40 Hell, S. W. Far-field optical nanoscopy. Science 316, 1153-1158, doi:10.1126/science.1137395 (2007).
41 Hell, S. W. Microscopy and its focal switch. Nature methods 6, 24-32, doi:10.1038/nmeth.1291 (2009).
42 Huang, B., Babcock, H. & Zhuang, X. Breaking the diffraction barrier: super-resolution imaging of cells. Cell 143, 1047-1058, doi:10.1016/j.cell.2010.12.002 (2010).
43 Vogelsang, J. et al. Make them blink: probes for super-resolution microscopy. Chemphyschem 11, 2475-2490, doi:10.1002/cphc.201000189 (2010).
44 Walter, N. G., Huang, C. Y., Manzo, A. J. & Sobhy, M. A. Do-it-yourself guide: how to use the modern single-molecule toolkit. Nature Methods 5, 475-489, doi:10.1038/nmeth.1215 (2008).
45 Hell, S. W. & Wichmann, J. Breaking the Diffraction Resolution Limit by Stimulated-Emission-Stimulated-Emission-Depletion Fluorescence Microscopy. Opt Lett 19, 780-782 (1994).
46 Heilemann, M. et al. Subdiffraction-resolution fluorescence imaging with conventional fluorescent probes. Angew Chem Int Ed Engl 47, 6172-6176, doi:10.1002/anie.200802376 (2008).
47 Rust, M. J., Bates, M. & Zhuang, X. Sub-diffraction-limit imaging by stochastic optical reconstruction microscopy (STORM). Nat Methods 3, 793-795 (2006).
48 Betzig, E. et al. Imaging intracellular fluorescent proteins at nanometer resolution. Science 313, 1642-1645 (2006).
49 Steinhauer, C., Forthmann, C., Vogelsang, J. & Tinnefeld, P. Superresolution Microscopy on the Basis of Engineered Dark States. Journal of the American Chemical Society 130, 16840-16841, doi:Doi 10.1021/Ja806590m (2008).
50 Sharonov, A. & Hochstrasser, R. M. Wide-field subdiffraction imaging by accumulated binding of diffusing probes. Proceedings of the National Academy of Sciences of the U.S. of America 103, 18911-18916 (2006).
51 Yildiz, A. et al. Myosin V walks hand-over-hand: single fluorophore imaging with 1.5-nm localization. Science 300, 2061-2065, doi:10.1126/science.1084398 (2003).
52 Yildiz, A., Tomishige, M., Vale, R. D. & Selvin, P. R. Kinesin walks hand-over-hand. Science 303, 676-678, doi:10.1126/science.1093753 (2004).

53 Gautier, A. et al. An engineered protein tag for multi-protein labeling in living cells. Chem Biol 15, 128-136, doi:10.1016/j.chembiol.2008.01.007 (2008).
54 Jones, S. A., Shim, S. H., He, J. & Zhuang, X. Fast, three-dimensional super-resolution imaging of live cells. Nature methods 8, 499-508, doi:10.1038/nmeth.1605 (2011).
55 Keppler, A. et al. A general method for the covalent labeling of fusion proteins with small molecules in vivo. Nature biotechnology 21, 86-89, doi:10.1038/nbt765 (2003).
56 Klein, T. et al. Live-cell dSTORM with SNAP-tag fusion proteins. Nature methods 8, 7-9, doi:10.1038/nmeth0111-7b (2011).
57 Cunin, F. et al. Biomolecular screening with encoded porous-silicon photonic crystals. Nature materials 1, 39-41, doi:10.1038/nmat702 (2002).
58 Bellot, G., Mcclintock, M. A., Lin, C. & Shih, W. M. Recovery of intact DNA nanostructures after agarose gel-based separation. Nature methods 8, 192-194, doi:10.1038/nmeth0311-192 (2011).
59 Rajendran, A., Endo, M., Katsuda, Y., Hidaka, K. & Sugiyama, H. Photo-cross-linking-assisted thermal stability of DNA origami structures and its application for higher-temperature self-assembly. Journal of the American Chemical Society 133, 14488-14491, doi:10.1021/ja204546h (2011).

EQUIVALENTS

Those skilled in the art will recognize, or be able to ascertain using no more than routine experimentation, many equivalents of the specific embodiments of the subject matter described herein. Such equivalents are intended to be encompassed by the following claims.

All publications, patents, and patent applications cited in this specification are herein incorporated by reference to the same extent as if each individual publication or patent application was specifically and individually indicated to be incorporated by reference.

What is claimed is:

1. A method of detecting a target comprising:

contacting a sample with a nucleic acid barcode probe comprising a nucleic acid nanorod bound to a target-binding moiety, wherein the nucleic acid nanorod comprises a distinct barcode pattern formed by the position and color of at least two fluorescently-labeled regions that are separated from each other by a fixed distance of at least 200 nm; and determining whether the nucleic acid barcode probe binds to one or more components in the sample, wherein binding of the nucleic acid barcode probe to one or more components in the sample indicates presence of a target in the sample.

2. The method of claim 1, further comprising identifying the target based on the position and color of the fluorescently labeled regions of the nucleic acid barcode probe bound to one or more components of the sample.

3. The method of claim 1, wherein the at least two fluorescently labeled regions of the nucleic acid barcode probe comprise soluble, transiently binding fluorophore-bearing oligonucleotides.

4. The method of claim 1, wherein the at least two fluorescently labeled regions of the nucleic acid barcode probe comprise stably bound fluorophore-bearing oligonucleotides.

5. A method of detecting a target comprising contacting the target with a nucleic acid barcode probe that comprises a nucleic acid nanorod bound to a target-binding moiety, wherein the nucleic acid nanorod comprises a distinct barcode pattern formed by the position and color of at least two fluorescently-labeled regions that are separated from each other by a fixed distance of at least 200 nm;

separating the target from material that is not bound to the target; and detecting the presence of the nucleic acid barcode probe bound to the target.

6. The method of claim 5, further comprising identifying the target based on the position and color of the fluorescently labeled regions of the nucleic acid barcode probe bound to the target.

7. The method of claim 5, wherein the at least two fluorescently labeled regions of the nucleic acid barcode probe are labeled with soluble, transiently bound fluorophore-bearing oligonucleotides.

8. The method of claim 5, wherein the at least two fluorescently labeled regions of the nucleic acid barcode probe comprises stably bound fluorophore-bearing oligonucleotides.

9. The method of claim 1, wherein the nucleic acid nanorod is a DNA nanorod.

10. The method of claim 1, wherein at least two of the fluorescent labels are separated from each other by a structurally rigid region of the nanorod.

11. The method of claim 1, wherein the nucleic acid nanorod comprises a scaffold strand and a plurality of staple strands.

12. The method of claim 11, wherein the staple strands are labeled with a fluorophore, and the fluorophore-labeled staple strands comprise (a) a staple domain hybridized to the scaffold strand and (b) a handle domain.

13. The method of claim 12, wherein the handle domain is hybridized to a fluorophore-labeled oligonucleotide.

14. The method of claim 1, wherein the target-binding moiety is a single-stranded nucleic acid, or a protein or peptide.

15. The method of claim 14, wherein the protein is an antibody.

16. The method of claim 1, wherein the target is a target nucleic acid, a target protein or peptide, a target cell, or a combination thereof.

17. The method of claim 1, wherein binding of the nucleic acid barcode probe to one or more components in the sample is determined by fluorescent microscopy.

18. The method of claim 1, wherein the fluorophores are arranged in a geometric pattern.

19. The method of claim 1, wherein each of the fluorescently-labeled regions has a center that is located at least 200 nm from any other center of a fluorescently-labeled region on the probe.

20. The method of claim 5, wherein each of the fluorescently-labeled regions has a center that is located at least 200 nm from any other center of a fluorescently-labeled region on the probe.

* * * * *